US009018208B2

(12) United States Patent
Christos et al.

(10) Patent No.: US 9,018,208 B2
(45) Date of Patent: Apr. 28, 2015

(54) HETEROCYCLES AS POTASSIUM CHANNEL MODULATORS

(71) Applicant: Icagen Inc., Durham, NC (US)

(72) Inventors: Thomas Eugene Christos, Wake Forest, NC (US); George S. Amato, Cary, NC (US); Robert N. Atkinson, Raleigh, NC (US); Maria Graciela Barolli, Morrisville, NC (US); Lilli Ann Wolf-Gouveia, Bahama, NC (US); Mark J. Suto, Chapel Hill, NC (US)

(73) Assignee: Icagen Inc., Durham, NC (US)

( * ) Notice: Subject to any disclaimer, the term of this patent is extended or adjusted under 35 U.S.C. 154(b) by 56 days.

(21) Appl. No.: 13/756,759

(22) Filed: Feb. 1, 2013

(65) Prior Publication Data

US 2013/0143889 A1 Jun. 6, 2013

Related U.S. Application Data

(60) Division of application No. 12/706,574, filed on Feb. 16, 2010, now Pat. No. 8,431,608, which is a continuation-in-part of application No. 12/193,639, filed on Aug. 18, 2008, now Pat. No. 8,058,274, which is a continuation-in-part of application No. PCT/US2008/073519, filed on Aug. 18, 2008.

(60) Provisional application No. 61/078,241, filed on Jul. 3, 2008, provisional application No. 60/956,640, filed on Aug. 17, 2007.

(51) Int. Cl.
*C07D 487/04* (2006.01)
*A61K 31/5025* (2006.01)
*C07D 471/04* (2006.01)

(52) U.S. Cl.
CPC .......... *C07D 487/04* (2013.01); *A61K 31/5025* (2013.01); *C07D 471/04* (2013.01)

(58) Field of Classification Search
CPC .......................... A61K 31/5025; C07D 487/04
USPC .......................................... 514/248; 544/236
See application file for complete search history.

(56) References Cited

U.S. PATENT DOCUMENTS

| | | | |
|---|---|---|---|
| 3,701,780 | A | 10/1972 | Fisher |
| 7,105,534 | B2 | 9/2006 | Beatch et al. |
| 7,157,490 | B2 | 1/2007 | Colandrea et al. |
| 7,563,788 | B2 | 7/2009 | Sciotti et al. |
| 8,058,274 | B2 * | 11/2011 | Christos et al. ............... 514/248 |
| 2004/0082583 | A1 | 4/2004 | Cheung et al. |
| 2005/0250833 | A1 | 11/2005 | Attali et al. |
| 2007/0099899 | A1 | 5/2007 | Atwal et al. |
| 2007/0149508 | A1 | 6/2007 | Noronha et al. |
| 2009/0137595 | A1 | 5/2009 | Sakai et al. |
| 2009/0163489 | A1 | 6/2009 | Booker et al. |
| 2010/0029619 | A1 | 2/2010 | Uchikawa et al. |

FOREIGN PATENT DOCUMENTS

| | | |
|---|---|---|
| JP | 1977073896 | 12/1976 |
| JP | 198968375 | 3/1989 |
| JP | 2005505535 | 2/2005 |
| WO | 2006054652 | 5/2006 |
| WO | 2007095588 | 8/2007 |
| WO | 2008030579 | 3/2008 |
| WO | 2009026254 | 2/2009 |
| WO | 2009136663 | 11/2009 |

OTHER PUBLICATIONS

Compound (CAS RN 724696-41-7), entering STN database for public use on Aug. 9, 2004.*
Hamdouchi, Chafiq, et al., "Chemoselective Arylsulfenylation of 2-Aminoimidazo[1,2-a]pyridines by Phenyliodine (III) Bis(trifluoroacetate) (PIFA)", Synthesis, Jun. 1998, pp. 867-872, vol. 6.
Bochis, R., et al., "Substitued Imidazo[1,2-a]pyridine-2-carbamate Anthelmintics", Journal of Medicinal Chemistry, 1981, pp. 1518-1521, 24(12).
Hand, Samkula E., et al., "Teleamination of the Imidazo[1,2-a]pyridine System", Journal of Organic Chemistry, 1978, pp. 2900-2906, 43(14).
Ackerman, M.J. et al., "Mechanisms of Disease," The New England Journal of Medicine, May 29, 1997, pp. 1575-1587, 336(22).
Biervert, C. et al., "A Potassium Channel Mutation in Neonatal Human Epilepsy", Science, Jan. 16, 1998, pp. 403-406, vol. 279.
Blatz, A.I. et al., "Single apamin-blocked Ca-activated K+ channels of small conductance in cultured rat skeletal muscle," Nature, Oct. 23, 1986, pp. 718-720, vol. 323.
Butler, A. et al., "mSlo, a complex mouse gene encoding "Maxi" calcium-activated potassium channels," Science, Jul. 9, 1993, pp. 221-224, vol. 261.
Daniel, S., et al., "Screening for Potassium Channel Modulators by a High Through-Put 86—Rubidium Efflux in a 96-Well Microtiter Plate," Journal of Pharmacological Methods, 1991, pp. 185-193, vol. 25.
Hamil, O.P., et al., "Improved Patch-Clamp Techniques for High-Resolution Current Recording from Cells and Cell-Free Membrane Patches," Pflügers Archive, 1981, pp. 85-100, vol. 391.

(Continued)

*Primary Examiner* — Yong Chu
(74) *Attorney, Agent, or Firm* — Richard V. Zanzalari

(57) ABSTRACT

Compounds, compositions and methods are provided which are useful in the treatment of diseases through the modulation of potassium ion flux through voltage-dependent potassium channels. More particularly, the invention provides heterocycles, compositions and methods that are useful in the treatment of central or peripheral nervous system disorders (e.g., migraine, ataxia, Parkinson's disease, bipolar disorders, trigeminal neuralgia, spasticity, mood disorders, brain tumors, psychotic disorders, myokymia, seizures, epilepsy, seizure, retinal degeneration, hearing and vision loss, Alzheimer's disease, age-10 related memory loss, learning deficiencies, anxiety, neuronal degeneration and motor neuron diseases, maintaining bladder control or treating urinary incontinence) and as neuroprotective agents (e.g., to prevent stroke and the like) by modulating potassium channels associated with the onset or recurrence of the indicated conditions.

9 Claims, No Drawings

(56) References Cited

OTHER PUBLICATIONS

Heinemann, S.H., et al., "Functional characterization of Kv channel beta-subunits from rat brain," Journal of Physiology, 1996, pp. 625-633, vol. 493.3.
Holevinsky, K.O., et al., "ATP-sensitive K+ Channel Opener Acts as a Potent Cl- Channel Inhibitor in Vascular Smooth Muscle Cells," The Journal of Membrane Biology, 1994, pp. 59-70, vol. 137.
International Search Report mailed on Nov. 12, 2008, for International Application No. PCT/US08/73519 filed on Aug. 18, 2008, 2 pages.
Joiner, W.J., et al., "Formation of intermediate-conductance calcium-activated potassium channels by interaction of Slack and Slo subunits," Nature Neuroscience, Oct. 1998, pp. 462-469, 1(6).
Kananura, C., et al., "The new voltage gated potassium channel KCNQ5 and neonatal convulsions," NeuroReport, Jun. 26, 2000, pp. 2063-2067, 11(9).
Kim, S.H., et al., "An experimental model for peripheral neuropathy produced by segmental spinal nerve ligation in the rat," Pain, 1992, pp. 355-362, vol. 50.
Kubisch, C., et al., "KCNQ4, a Novel Potassium Channel Expressed in Sensory Outer Hair Cells, is Mutated in Dominant Deafness," Cell, Feb. 5, 1999, pp. 437-446, 96(3).
Leppert, M., et al., "Benign familial neonatal convulsions linked to genetic markers on chromosome 20," Nature, Feb. 16, 1989, pp. 647-648, vol. 337.
Relevant portion of International Search Report for related Application No. PCT/US2011/023444, mailed Apr. 14, 2011.
Main, M.J., et al., "Modulation of KCNQ2/3 Potassium Channels by the Novel Anticonvulsant Retigabine," Molecular Pharmacology, 2000, pp. 253-262, vol. 58.
Meera, P., et al., "Large conductance voltage- and calcium-dependent K+ channel, a distinct member of voltage-dependent ion channels with seven N-terminal transmembrane segments (S0-S6), an extracellular N terminus, and an intracellular (S9-S10) C terminus," Proceeding of National Academy of Science, USA, Dec. 1997, pp. 14066-14071, 94(25).
Mourad et al., "Synthesis of imidazo[1,2-b]pyridazines: Fenbendazole, oxifenbendazole analogs and related derivatives", Journal of Heterocyclic Chemistry, Oct./Nov. 1993, pp. 1365-1372, 30(5).
Mourad et al., "Methyl imidazo[1,2-b]pyridazine-2-carbamates and related compounds as potential antifilarial agents", Journal of Heterocyclic Chemistry, 1992, pp. 1583-1592, 29(6).
Park, Youngbae, "Ion selectivity and gating of small conductance Ca2+-activated K+ channels in cultured rat adrenal chromaffin cells," Journal of Physiology, 1994, pp. 555-570, 481(3).
Robbins, J., et al., "Kinetic and Pharmacological Properties of the M-Current in Rodent Neuroblastoma x Glioma Hybrid Cells," Journal of Physiology, 1992, pp. 159-185, vol. 451.
Sanguinetii, M.C., et al., "Coassembly of KvLQT1 and minK (IsK) proteins to form cardiac iKS potassium channel," Nature, Nov. 7, 1996, pp. 80-83, vol. 384.
Schreiber, M. et al., "Slo3, a Novel pH-sensitive K+ Channel from Mammalian Spermatocytes," The Journal of Biological Chemistry, Feb. 6, 1998, pp. 3509-3516, 273(6).
Schroeder, B.C., et al., "KCNQ5, a Novel Potassium Channel Broadly Expressed in Brain, Mediated M-type Currents," The Journal of Biological Chemistry, Aug. 4, 2000, pp. 24089-24095, 275(31).
Selyanko, A.A., et al., "Two Types of K+ Channel Subunit, Erg1 and KCNQ2/3, Contribute to the M-Like Current in a Mammalian Neuronal Cell," The Journal of Neuroscience, Sep. 15, 1999, pp. 7742-7756, 19(18).
Selyanko, A.A., et al., "Dominant-Negative Subunits Reveal Potassium Channel Families That Contribute to M-Like Potassium Currents," the Journal of Neuroscience, 2002, pp. RC212(1-5), vol. 22.
Shi, G., et al., "βSubunits Promote K+ Channel Surface Expression through Effects Early in Biosynthesis," Neuron, Apr. 1996, pp. 843-852, vol. 16.
Vestergaard-Bogind, B., et al., "Single-File Diffusion through the Ca2+-Activated K+ Channel of Human Red Cells," The Journal of Membrane Biology, 1985, pp. 67-75, vol. 88.
Wang, H-S., et al., "KCNQ2 and KCNQ3 Potassium Channel Subunits: Molecular Correlates of the M-Channel," Science, Dec. 4, 1998, pp. 1890-1893, vol. 282.
Wei, A. et al., "Eight Potassium Channel Families Revealed by the *C. elegans* Genome Project," Neuropharmacology, 1996, pp. 805-829, 35(7).
Wickenden, A., et al., "Characterization of KCNQ5/Q3 potassium channels expressed in mammalian cells," British Journal of Pharmacology, 2001, pp. 381-384, vol. 132.
Acero-Alarcon, A. et al., "Unusual Ring Closure Reaction of Amides with Pyrimidines: Novel Stereoselective Synthesis of Hexahydroimidazo[1,2-c]pyrimidines," Synthesis, 1999, pp. 2124-2130, vol. 12.
Database Registry (online) Chemical Abstracts Service, Columbus, OH, US; Nov. 11, 2007, XP002629766, Database accession No. 952958-52-0 [abstract].
Haswgawa, et al., "Discovery of Novel Benzimidazoles as Potent Inhibitors of TIE-2 and VEGFR-2 Tyrosine Kinase Receptors", Journal of Medicinal Chemistry, 2007, pp. 4453-4470, 50(18).

\* cited by examiner

HETEROCYCLES AS POTASSIUM CHANNEL MODULATORS

CROSS-REFERENCES TO RELATED APPLICATIONS

This application is a Divisional of U.S. patent application Ser. No. 12/706,574 filed Feb. 16, 2010, which is a Continuation-in-part of PCT Patent Application No. PCT/US2008/073519, filed Aug. 18, 2008, and is a Continuation-in-part of U.S. patent application Ser. No. 12/193,639 filed Aug. 18, 2008, each of which claims the benefit of U.S. Provisional Patent Application No. 61/078,241 filed Jul. 3, 2008 and U.S. Provisional Patent Application No. 60/956,640, filed Aug. 17, 2007, the disclosures of which are hereby incorporated by reference in their entirety and for all Purposes.

BACKGROUND OF THE INVENTION

Ion channels are cellular proteins that regulate the flow of ions, including calcium, potassium, sodium and chloride, into and out of cells. These channels are present in all human cells and affect such processes as nerve transmission, muscle contraction and cellular secretion. Among the ion channels, potassium channels are the most ubiquitous and diverse, being found in a variety of animal cells such as nervous, muscular, glandular, immune, reproductive, and epithelial tissue. These channels allow the flow of potassium in and/or out of the cell under certain conditions. For example, the outward flow of potassium ions upon opening of these channels makes the interior of the cell more negative, counteracting depolarizing voltages applied to the cell. These channels are regulated, e.g., by calcium sensitivity, voltage-gating, second messengers, extracellular ligands, and ATP-sensitivity.

Potassium channels are associated with a number of physiological processes, including regulation of heartbeat, dilation of arteries, release of insulin, excitability of nerve cells, and regulation of renal electrolyte transport. Potassium channels are made by alpha subunits that fall into at least 8 families, based on predicted structural and functional similarities (Wei et al., *Neuropharmacology* 35(7): 805-829 (1997)). Three of these families (Kv, eag-related, and KQT) share a common motif of six transmembrane domains and are primarily gated by voltage. Two other families, CNG and SK/IK, also contain this motif but are gated by cyclic nucleotides and calcium, respectively. The three other families of potassium channel alpha subunits have distinct patterns of transmembrane domains. Slo family potassium channels, or BK channels have seven transmembrane domains (Meera et al., *Proc. Natl. Acad. Sci. U.S.A.* 94(25): 14066-71 (1997)) and are gated by both voltage and calcium or pH (Schreiber et al., *J. Biol. Chem.* 273: 3509-16 (1998)). Another family, the inward rectifier potassium channels (Kir), belongs to a structural family containing two transmembrane domains, and an eighth functionally diverse family (TP, or "two-pore") contains two tandem repeats of this inward rectifier motif.

Potassium channels are typically formed by four alpha subunits, and can be homomeric (made of identical alpha subunits) or heteromeric (made of two or more distinct types of alpha subunits). In addition, potassium channels made from Kv, KQT and Slo or BK subunits have often been found to contain additional, structurally distinct auxiliary, or beta, subunits. These subunits do not form potassium channels themselves, but instead they act as auxiliary subunits to modify the functional properties of channels formed by alpha subunits. For example, the Kv beta subunits are cytoplasmic and are known to increase the surface expression of Kv channels and/or modify inactivation kinetics of the channel (Heinemann et al., *J. Physiol.* 493: 625-633 (1996); Shi et al., *Neuron* 16(4): 843-852 (1996)). In another example, the KQT family beta subunit, minK, primarily changes activation kinetics (Sanguinetti et al., *Nature* 384: 80-83 (1996)).

Slo or BK potassium channels are large conductance potassium channels found in a wide variety of tissues, both in the central nervous system and periphery. They play a key role in the regulation of processes such as neuronal integration, muscular contraction and hormone secretion. They may also be involved in processes such as lymphocyte differentiation and cell proliferation, spermatocyte differentiation and sperm motility. Three alpha subunits of the Slo family have been cloned, i.e., Slo1, Slo2, and Slo3 (Butler et al., *Science* 261: 221-224 (1993); Schreiber et al., *J. Biol. Chem.*, 273: 3509-16 (1998); and Joiner et al., *Nature Neurosci.* 1: 462-469 (1998)). These Slo family members have been shown to be voltage and/or calcium gated, and/or regulated by intracellular pH.

Certain members of the Kv family of potassium channels were recently renamed (see, Biervert, et al., *Science* 279: 403-406 (1998)). KvLQT1 was re-named KCNQ1, and the KvLQT1-related channels (KvLR1 and KvLR2) were renamed KCNQ2 and KCNQ3, respectively. More recently, additional members of the KCNQ subfamily were identified. For example, KCNQ4 was identified as a channel expressed in sensory outer hair cells (Kubisch, et al., *Cell* 96(3): 437-446 (1999)). KCNQ5 (Kananura et al., *Neuroreport* 11(9): 2063 (2000)), KCNQ 2/3 (Main et al., *Mol. Pharmacol.* 58: 253-62 (2000), KCNQ 3/5 (Wickenden et al., *Br. J. Pharma* 132: 381 (2001)) and KCNQ6 have also recently been described.

KCNQ2 and KCNQ3 have been shown to be nervous system-specific potassium channels associated with benign familial neonatal convulsions ("BFNC"), a class of idiopathic generalized epilepsy (see, Leppert, et al., *Nature* 337: 647-648 (1989)). These channels have been linked to M-current channels (see, Wang, et al., *Science* 282: 1890-1893 (1998)). The discovery and characterization of these channels and currents provides useful insights into how these voltage dependent (Kv) potassium channels function in different environments, and how they respond to various activation mechanisms. Such information has now led to the identification of modulators of KCNQ2 and KCNQ3 potassium channels or the M-current, and the use of such modulators as therapeutic agents.

SUMMARY OF THE INVENTION

This invention relates to the use of certain heterocycles as potassium channel modulators and to the treatment of diseases in which a potassium channel is implicated. Additionally, this invention relates to novel compounds that are useful as potassium channel modulators. In particular, the present invention provides heterocycles and pharmaceutically acceptable salts, hydrates or solvates thereof, which are useful in the treatment of diseases through the modulation of potassium ion flux through voltage-dependent potassium channels.

In one aspect, the present invention provides a compound of Formula (I):

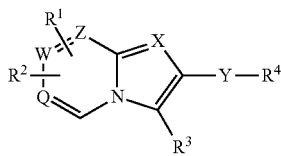

Formula (I)

or a pharmaceutically acceptable salt, solvate or complex thereof, wherein Q, W, Z are members independently selected from carbon and nitrogen; with the proviso that when Q is nitrogen, W and Z are carbon; with the further proviso that when W is nitrogen, Q and Z are carbon; with the further proviso that when Z is nitrogen, Q and W are carbon. X is a member selected from carbon and nitrogen. Y is a member selected from —$(CH_2)_n$—C(O)—$NR^5$—, —$(CH_2)_n$—$NR^5$—C(O)—, —$(CH_2)_n$—$CR^6R^7NR^5C(O)$—, —$(CH_2)_n$—$S(O)_2$—$NR^5$— and —$(CH_2)_n$—$NR^5$—$S(O)_2$—. The index n is an integer selected from 0, 1, 2, 3, 4, 5 and 6. $R^5$, $R^6$ and $R^7$ are members independently selected from H, substituted or unsubstituted $C_1$-$C_7$ alkyl group, substituted or unsubstituted aryl and substituted or unsubstituted arylalkyl. $R^1$ and $R^2$ are members independently selected from H, $C_1$-$C_7$ substituted or unsubstituted alkyl, CN, $CF_3$, $OCF_3$, $SCF_3$, halogen, thioalkyl, $S(O)R^8$, $S(O)_2R^8$, $C(O)R^8$, $C(O)_2R^8$, substituted or unsubstituted benzyl, substituted or unsubstituted phenyl and substituted or unsubstituted heteroaryl. $R^8$ is a member selected from H, substituted or unsubstituted $C_1$-$C_7$ alkyl, substituted or unsubstituted benzyl, substituted or unsubstituted phenyl and substituted or unsubstituted heteroaryl. $R^3$ is a member selected from the group consisting of $CF_3$, —$(CH_2)_mCF_3$, substituted or unsubstituted $C_1$-$C_9$ alkyl, substituted or unsubstituted aryl, substituted or unsubstituted heteroaryl and substituted or unsubstituted $C_3$-$C_8$ cycloalkyl. The index m is an integer selected from 0, 1, 2, 3, 4, 5 and 6. $R^4$ is a member selected from substituted or unsubstituted $C_1$-$C_9$ alkyl, substituted or unsubstituted aryl, substituted or unsubstituted heteroaryl, substituted or unsubstituted $C_3$-$C_9$ cyclo or bicyclo alkyl and —$(CH_2)_pCF_3$. The index p is an integer selected from 0, 1, 2, 3, 4, 5 and 6.

In another aspect, the present invention provides a compound of Formula (V)

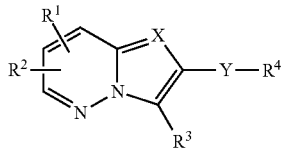

(V)

or a pharmaceutically acceptable salt, hydrate, solvate or complex thereof, wherein: X is Nitrogen; Y is a member selected from the group —$(CH_2)_n$—C(O)—$NR_5$—, —$(CH_2)_n$—$NR_5$—C(O)—, —$(CH_2)_n$—$CR_6R_7NR_5C(O)$—, —$(CH_2)_n$—$S(O)_2$—$NR_5$—, —$(CH_2)_n$—$NR_5$—$S(O)_2$—; wherein $R_5$, $R_6$ and $R_7$ are a member selected from —H, substituted or unsubstituted $C_1$-$C_7$ alkyl group and n is an integer from 0-6, substituted or unsubstituted aryl, substituted or unsubstituted alkyl aryl; $R_1$ and $R_2$ are independently —H, $C_1$-$C_7$ substituted or unsubstituted alkyl, CN, $CF_3$, $OCF_3$, $SCF_3$, halogen, thioalkyl, $S(O)R_8S(O)_2R_8$, $C(O)R_8$, $C(O)_2R_8$, optimally substituted benzyl, phenyl or heteroaryl; wherein $R_8$ is a member selected from the group consisting of —H and a substituted or unsubstituted $C_1$-$C_7$ alkyl, optimally substituted benzyl, phenyl or heteroaryl; group; $R_3$ is a member selected from the group consisting of $CF_3$, —$(CH_2)_nCF_3$, wherein n is an integer from 0-6, substituted or unsubstituted $C_1$-$C_8$ alkyl, substituted or unsubstituted aryl, substituted or unsubstituted heteroaryl, substituted or unsubstituted $C_3$-$C_8$ cycloalkyl; $R_4$ is a member selected from the group consisting of substituted or unsubstituted $C_1$-$C_9$ alkyl, substituted or unsubstituted aryl, substituted or unsubstituted heteroaryl, substituted or unsubstituted $C_3$-$C_9$ cyclo or bicyclo alkyl, or —$(CH_2)_nCF_3$, wherein n is an integer from 0-6.

In yet another aspect, the present invention provides a compound of Formula (IX):

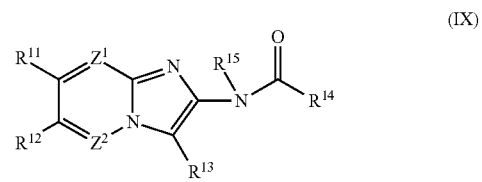

(IX)

or a pharmaceutically acceptable salt, hydrate or solvate thereof, $R^{11}$ and $R^{12}$ are each independently selected from the group consisting of —H, halogen, $C_{1-8}$haloalkyl, —CN, $C_{1-8}$alkyl, $C_{1-8}$alkoxy, aryloxy and aryl-$C_{1-8}$alkoxy;

$R^{13}$ is selected from the group consisting of —H, $C_{1-8}$alkyl, $C_{2-8}$alkenyl, aryl, $C_{3-8}$cycloalkyl, aryl-$C_{1-6}$alkyl, $C_{3-8}$cycloalkyl-$C_{1-8}$alkyl, heteroaryl and heteroaryl-$C_{1-6}$alkyl, wherein the aromatic portion of the $R^{13}$ group is optionally substituted with from 1-3 $R^a$ substituents, each $R^a$ is independently selected from the group consisting of halogen, $C_{1-8}$haloalkoxy, $C_{1-8}$alkoxy, $C_{1-8}$haloalkyl, —CN and $R^b$, wherein $R^b$ is $C_{1-8}$alkyl optionally substituted with from 1-2 substituents selected from halogen, —CN, —OH, $C_{1-8}$haloalkoxy or $C_{1-8}$alkoxy; or any two adjacent $R^a$ substituents together with the atoms to which they are attached form a 5- or 6-membered carbocyclic ring, optionally substituted with a $C_{1-8}$alkyl;

$R^{14}$ is selected from the group consisting of $C_{1-8}$alkyl, $C_{1-8}$haloalkyl, $C_{3-8}$cycloalkyl, $C_{3-8}$cycloalkyl-$C_{1-8}$alkyl, aryl, aryl-$C_{1-8}$alkyl, $C_{1-8}$alkoxy, aryl-$C_{1-8}$alkoxy, $C_{4-5}$heterocycloalkyl, $C_{4-5}$heterocycloalkyl-$C_{1-8}$alkyl, $R^c$, —$NHR^d$ and —$N(R^d)_2$, wherein $R^c$ is $C_{1-8}$alkyl substituted with from 1-2 members selected from —OH, —$CH_2N(R^d)_2$, —OC(O)$C_{1-8}$alkyl, —OC(O)aryl, $C_{1-8}$alkoxy or aryloxy and $R^d$ is $C_{1-8}$alkyl or aryl-$C_{1-8}$alkyl, wherein the aromatic portion of the $R^{14}$ group is optionally substituted with from 1-3 $R^e$ substituents independently selected from the group consisting of halogen, $C_{1-8}$haloalkyl, $C_{1-8}$alkyl, $C_{1-8}$alkoxy, —CN or haloalkoxy, —OH, —OC(O)O—$R^f$, —OC(O)$R^f$, —OC(O)$NHR^f$, —OC(O)N($R^f)_2$, —S(O)$R^f$, —S(O)$_2R^f$, —$SO_2NH_2$, —S(O)$_2NHR^f$, —S(O)$_2N(R^f)_2$, —NHS(O)$_2R^f$, —$NR^f$ S(O)$_2R^f$, —C(O)$NH_2$, —C(O)$NHR^f$, —C(O)N($R^f)_2$, —C(O)$R^f$, —C(O)H, wherein each $R^f$ is independently a $C_{1-8}$alkyl; and the cycloalkyl portion of the $R^{14}$ group is optionally substituted with from 1-3 substituents selected from halogen, $C_{1-8}$alkyl or optionally fused with a 5- or 6-membered aromatic ring having from 0-2 heteroatoms as ring members selected from N, O or S; $R^{15}$ is —H or —C(O)$C_{1-8}$alkyl;

$Z^1$ is =N— or =C($R^{16}$)— and $Z^2$ is =N— or =C($R^{17}$)—, wherein $R^{16}$ and $R^{17}$ are each independently —H, $C_{1-8}$alkyl, halogen, —CN, $C_{1-8}$haloalkyl, $C_{1-8}$haloalkoxy, —$OR^g$ or —$N(R^g)_2$, wherein $R^g$ is independently —H, $C_{1-8}$alkyl or aryl-$C_{1-8}$alkyl, with the proviso that $Z^1$ and $Z^2$ are not simultaneously =N—;

In Formula (IX), at each occurrence, "alkyl" by itself or as part of another substituent, is an unsubstituted, fully saturated, straight or branched chain hydrocarbon radical unless specified otherwise;

In Formula (IX), at each occurrence, "cycloalkyl" by itself or as part of another substituent is an unsubstituted, fully saturated, cyclic hydrocarbon radical unless specified otherwise; and In Formula (IX), at each occurrence, "aryl" by itself or as part of another substituent is a monovalent monocyclic, bicyclic or polycyclic polyunsaturated aromatic hydrocarbon radical. In some preferred embodiments, "aryl" by itself or as part of another substituent denotes a monovalent monocyclic, bicyclic or polycyclic polyunsaturated unsubstituted aromatic hydrocarbon radical unless otherwise specified and "heteroaryl" by itself or as part of another substituent denotes unsubstituted aryl groups (or rings) that contains from one to five heteroatoms selected from N, O, or S, wherein the nitrogen and sulfur atoms are optionally oxidized, and the nitrogen atom(s) are optionally quaternized unless otherwise specified.

In still another aspect, the present invention provides a method for increasing flow through voltage dependent potassium channels in a cell. The method includes contacting the cell with a compound as described herein. In some embodiments, the method includes contacting the cell with a compound of Formula I, V or IX in an amount sufficient to open the potassium channels.

In yet another aspect, the present invention provides a method for treating a central or peripheral nervous system disorder or condition through the modulation of a voltage-dependent potassium channel. The method includes administering to a subject in need of such treatment an effective amount of a compound of as described herein. In some embodiments, the method includes administering to a subject in need of such treatment an effective amount of a compound of Formula I, V or IX.

Other objects and advantages of the present invention will be apparent from the detailed description that follows.

DETAILED DESCRIPTION OF THE INVENTION AND THE PREFERRED EMBODIMENTS

Abbreviations and Definitions

The abbreviations used herein have their conventional meaning within the chemical and biological arts. For example: CHO, Chinese hamster ovary; EBSS, Earl's Balanced Salt Solution; KCNQ, potassium channel Q; KCNQ2, potassium channel Q2, hSK, $Ca^{2+}$ activated small conductance potassium channels; SDS, sodium dodecyl sulfate; $Et_3N$, triethylamine; MeOH, methanol; and DMSO, dimethylsulfoxide; DCM, dichloromethane; NBS, N-bromosuccinimide; NIS, N-iodosuccinimide; TsCl, toluenesulfonyl chloride, dppa, diphenylphosphonic azide; TFAA, trifluoro acetic acid; THF, tetrahydrofuran.

The term "pain" refers to all categories of pain, including pain that is described in terms of stimulus or nerve response, e.g., somatic pain (normal nerve response to a noxious stimulus) and neuropathic pain (abnormal response of a injured or altered sensory pathway, often without clear noxious input); pain that is categorized temporally, e.g., chronic pain and acute pain; pain that is categorized in terms of its severity, e.g., mild, moderate, or severe; and pain that is a symptom or a result of a disease state or syndrome, e.g., inflammatory pain, cancer pain, AIDS pain, arthropathy, migraine, trigeminal neuralgia, cardiac ischaemia, and diabetic neuropathy (see, e.g., Harrison's Principles of Internal Medicine, pp. 93-98 (Wilson et al., eds., 12th ed. 1991); Williams et al., *J. of Med. Chem.* 42: 1481-1485 (1999), herein each incorporated by reference in their entirety).

"Somatic" pain, as described above, refers to a normal nerve response to a noxious stimulus such as injury or illness, e.g., trauma, burn, infection, inflammation, or disease process such as cancer, and includes both cutaneous pain (e.g., skin, muscle or joint derived) and visceral pain (e.g., organ derived).

"Neuropathic" pain, as described above, refers to pain resulting from injury to or chronic changes in peripheral and/or central sensory pathways, where the pain often occurs or persists without an obvious noxious input.

"Acute pain", as described above, refers to pain which is marked by short duration or a sudden onset.

"Chronic pain", as described above, refers to pain which is marked by long duration or frequent recurrence.

"Inflammatory pain", as described above, refers to pain which is produced as a symptom or a result of inflammation or an immune system disorder.

"Visceral pain", as described above, refers to pain which is located in an internal organ.

"Biological medium," as used herein refers to both in vitro and in vivo biological milieus. Exemplary in vitro "biological media" include, but are not limited to, cell culture, tissue culture, homogenates, plasma and blood. In vivo applications are generally performed in mammals, preferably humans.

"Compound of the invention," as used herein refers to a compound described herein, pharmaceutically acceptable salts, hydrates or solvates thereof, e.g., compounds of Formulas I, II, III, IV, V, VI, VII, VIII, IX, IXa, IXa-1, IXa-2, IXa-3, IXa-5, IXa-6, IXa-7, IXb-1, IXb-2, IXb-3, IXb-3, IXb-4, IXb-5, IXc, IXc-1, IXc-2, IXd-1 and IXd-2.

"Modulating," as used herein, refers to the ability of a compound of the invention to activate and/or inhibit a potassium channel, preferably, a KCNQ potassium channel. In some preferred embodiments, a compound of the invention activates a potassium channel, preferably, a KCNQ potassium channel.

"Opening" and "activating" are used interchangeably herein to refer to the partial or full activation of a KCNQ channel by a compound of the invention, which leads to an increase in ion flux either into or out of a cell in which a KCNQ channel is found.

Where substituent groups are specified by their conventional chemical formulae, written from left to right, they equally encompass the chemically identical substituents which would result from writing the structure from right to left, e.g., —$CH_2O$— is intended to also recite —$OCH_2$—; —$NHS(O)_2$— is also intended to represent. —$S(O)_2HN$—, etc.

The term "alkyl," by itself or as part of another substituent, means, unless otherwise stated, a straight- or branched-chain, or cyclic hydrocarbon radical, or combination thereof, which may be fully saturated, mono- or polyunsaturated and can include mono-, di- and multivalent radicals, having the number of carbon atoms designated (i.e. $C_{1-8}$ or $C_1$-$C_8$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, pentadienyl), ethynyl, 1- and 3-propynyl, 3-butynyl, and the higher homologs and isomers. The term "alkyl," unless otherwise noted, also preferably include those derivatives of alkyl defined in more detail below, such as "heteroalkyl." Alkyl groups that are limited to hydrocarbon groups are termed "homoalkyl". The term "alkyl", as used herein refers to alkyl, alkenyl and alkynyl moieties, each of which can be mono-, di- or polyvalent species. Alkyl groups are preferably substituted, e.g., with one or more group referred to herein below as an "alkyl group substituent." In one embodiment, alkyl includes a straight or branched chain fully saturated aliphatic hydrocarbon radicals having the number of carbon atoms designated. For example, $C_{1-8}$alkyl refers to a hydrocarbon radical straight or branched having 1, 2, 3, 4, 5, 6, 7 or 8 carbon atoms and includes, but are not limited to, $C_{1-2}$alkyl, $C_{1-4}$ alkyl, $C_{2-6}$ alkyl, $C_{2-4}$ alkyl, $C_{1-6}$ alkyl, $C_{2-8}$alkyl, $C_{1-7}$alkyl, $C_{2-7}$alkyl and $C_{3-8}$ alkyl. In some preferred embodiments, at each occurrence, "alkyl" is by itself or as part of another substituent, is an unsubstituted, fully saturated, straight or branched chain hydrocarbon radical unless otherwise specified.

The term "alkenyl" by itself or as part of another substituent refers to a linear or branched monovalent hydrocarbon radical, which may be mono- or polyunsaturated, having the number of carbon atoms designated. For example, "$C_{2-8}$ alkenyl" means an alkenyl radical having from 2, 3, 4, 5, 6, 7 or 8 atoms that is derived by the removal of one hydrogen atom from a single carbon atom of a parent alkane. Examples include, but are not limited to vinyl, 2-propenyl i.e. —CH═C(H)(CH$_3$), —CH═C(CH$_3$)$_2$, —C(CH$_3$)═C(H)$_2$, —C(CH$_3$)═C(H)(CH$_3$), —C(CH$_2$CH$_3$)═CH$_2$, butadienyl e.g. 2-(butadienyl), pentadienyl e.g. 2,4-pentadienyl and 3-(1,4-pentadienyl), and hexadienyl, among others, and higher homologs and stereoisomers thereof.

The term "alkylene" by itself or as part of another substituent means a divalent radical derived from an alkane, as exemplified, but not limited, by —CH$_2$CH$_2$CH$_2$CH$_2$—, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms. In some preferred embodiments, "alkylene" by itself or as part of another substituent means a linear or branched saturated divalent unsubstituted hydrocarbon radical unless specified otherwise. For example, $C_{1-6}$alkylene is meant to include methylene, ethylene, propylene, 2-methylpropylene, pentylene, and the like.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom selected from the group consisting of O, N, Si and S, and wherein the nitrogen and sulfur atoms may optionally be oxidized and the nitrogen heteroatom may optionally be quaternized. The heteroatom(s) O, N and S and Si may be placed at any interior position of the heteroalkyl group or at the position at which the alkyl group is attached to the remainder of the molecule. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH═CH—O—CH$_3$, —Si(CH$_3$)$_3$, —CH$_2$—CH═N—OCH$_3$, and —CH═CH—N(CH$_3$)—CH$_3$. Up to two heteroatoms may be consecutive, such as, for example, —CH$_2$—NH—OCH$_3$ and —CH$_2$—O—Si(CH$_3$)$_3$. Similarly, the term "heteroalkylene" by itself or as part of another substituent means a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. In some preferred embodiments, at each occurrence in any formula of the invention, "cycloalkyl" by itself or as part of another substituent is an unsubstituted, fully saturated, cyclic hydrocarbon radical unless otherwise specified.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" or "$C_{1-4}$ haloalkyl" is mean to include, but is not be limited to, trifluoromethyl, 2,2,2-trifluoroethyl, 4-chlorobutyl, 3-bromopropyl, and the like.

The term "aryl" means, unless otherwise stated, a polyunsaturated, aromatic, hydrocarbon substituent which can be a single ring or multiple rings (preferably from 1 to 3 rings) which are fused together or linked covalently. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. In some preferred embodiments, "aryl" by itself or as part of another substituent denotes a monovalent monocyclic, bicyclic or polycyclic polyunsaturated aromatic hydrocarbon radical. In yet other preferred embodiments, "aryl" by itself or as part of another substituent denotes a monovalent monocyclic, bicyclic or polycyclic polyunsaturated unsubstituted aromatic hydrocarbon radical unless otherwise specified and "heteroaryl" refers to unsubstituted aryl groups (or rings) that contains from one to five heteroatoms selected from N, O, or S, wherein the nitrogen and sulfur atoms are optionally oxidized, and the nitrogen atom(s) are optionally quaternized unless otherwise specified.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—NR'R", —SR',-halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R")=NR'", —S(O)R', —S(O)$_2$R', —S(O)$_2$NR'R", —NRSO$_2$R', —CN and —NO$_2$ in a number ranging from zero to (2 m'+1), where m' is the total number of carbon atoms in such radical. R', R", R'" and R"" each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: halogen, —OR', =O, =NR', =N—OR', —NR'R", —SR',-halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R")=NR'", —S(O)R', —S(O)$_2$R', —S(O)$_2$NR'R", —NRSO$_2$R', —CN and —NO$_2$, —R', —N$_3$, —CH(Ph)$_2$, fluoro(C$_4$-C$_4$)alkoxy, and fluoro(C$_3$-C$_4$)alkyl, in a number ranging from zero to the total number of open valences on the aromatic ring system; and where R', R", R'" and R"" are preferably independently selected from hydrogen, (C$_1$-C$_8$)alkyl and heteroalkyl, unsubstituted aryl and heteroaryl, (unsubstituted aryl)-(C$_1$-C$_4$)alkyl, and (unsubstituted aryl)oxy-(C$_1$-C$_4$)alkyl. When a compound of the invention includes more than one R group, for example, each of the R groups is independently selected as are each R', R", R'" and R"" groups when more than one of these groups is present.

Two of the substituents on adjacent atoms of the aryl or heteroaryl ring may optionally be replaced with a substituent of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R'")$_d$—, where s and d are independently integers of from 0 to 3, and X is —O—, —NR'—, —S—, —S(O)—, —S(O)$_2$—, or —S(O)$_2$NR'—. The substituents R, R', R" and R'" are preferably independently selected from hydrogen or substituted or unsubstituted (C$_1$-C$_6$)alkyl.

As used herein, the term "heteroatom" is meant to include oxygen (O), nitrogen (N), sulfur (S) and silicon (Si).

As used herein, the term "aryloxy" means a radical —OR', where R' is an aryl as defined herein, e.g., phenoxy and the like.

As used herein, the term "carbocyclic ring" means a saturated, unsaturated or partially saturated, mono-, bicyclic or polycyclic ring (preferably 1-3 rings), which contains only carbon ring atoms (preferably 3-14 ring carbon atoms). The carbocyclic ring can be non-aromatic or aromatic ring. Exemplary carbocyclic rings include cyclopentane ring, cyclohexane ring, benzene ring, naphthalene ring, and the like.

As used herein, the term "tautomer" means compounds produced by the phenomenon wherein a proton of one atom of a molecule shifts to another atom. See, Jerry March, Advanced Organic Chemistry: Reactions, Mechanisms and Structures, Fourth Edition, John Wiley & Sons, pages 69-74 (1992). The tautomers also refer to one of two or more structural isomers that exist in equilibrium and are readily converted from one isomeric form to another. Examples of include keto-enol tautomers, such as acetone/propen-2-ol, imine-enamine tautomers and the like, ring-chain tautomers, such as glucose/2,3,4,5,6-pentahydroxy-hexanal and the like, the tautomeric forms of heteroaryl groups containing a —N=C(H)—NH— ring atom arrangement, such as pyrazoles, imidazoles, benzimidazoles, triazoles, and tetrazoles. The compounds described herein may have one or more tautomers and therefore include various isomers. All such isomeric forms of these compounds are expressly included in the present invention.

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, nrionohydrogenphosphoric, dihydrogenphosphoric, sulfuric, monohydrogensulfuric, hydriodic, or phosphorous acids and the like, as well as the salts derived from relatively, nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science*, 1977, 66, 1-19). Certain specific compounds of the present invention contain both basic and acidic functionalities that allow the compounds to be converted into either base or acid addition salts.

When the compound prepared by a method of the invention is a pharmacological agent, the salt is preferably a pharmaceutically acceptable salt. Examples of pharmaceutically acceptable salts are presented hereinabove, and are generally known in the art. See, for example, Wermuth, C., PHARMACEUTICAL SALTS: PROPERTIES, SELECTION AND USE—A HANDBOOK, Verlag Helvetica Chimica Acta (2002).

The neutral forms of the compounds are preferably regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds, which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. "Hydrate" refers to a complex formed by combination of water molecules with molecules or ions of the solute. "Solvate" refers to a complex formed by combination of solvent molecules with molecules or ions of the solute. The solvent can be an organic compound, an inorganic compound, or a mixture of both. Solvate is meant to include hydrate. Some examples of solvents include, but are not limited to, methanol, N,N-dimethylformamide, tetrahydrofuran, dimethylsulfoxide, and water. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are encompassed within the scope of the present invention. These isomers can be resolved or asymmetrically synthesized using conventional methods to render the isomers "optically pure", i.e., substantially free of its other isomers. If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diasteromers thus formed by fractional crystallization or chromatographic means well known in the art, and subsequent recovery of the pure enantiomers.

The compounds of the present invention may also contain unnatural proportions of atomic isotopes at one or more of the atoms that constitute such compounds. For example, the compounds may be radiolabelled with radioactive isotopes, such as for example tritium ($^3H$), iodine-125 ($^{125}I$) or carbon-14 ($^{14}C$). All isotopic variations of the compounds of the present invention, whether radioactive or not, are intended to be encompassed within the scope of the present invention.

The symbol $\xi$ denotes a point of attachment of a moiety to the remainder of a molecule.

DESCRIPTION OF THE EMBODIMENTS

I. Modulators of Voltage-Dependent Potassium Channels

In one aspect, the present invention provides compounds of the formula (I):

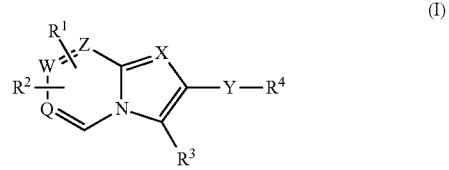

(I)

or a pharmaceutically acceptable salt hydrate, solvate or complex thereof wherein Q, W, Z are members independently selected from carbon and nitrogen, with the proviso that when Q is nitrogen, W and Z are carbon; with the further proviso that when W is nitrogen, Q and Z are carbon; with the further proviso that when Z is nitrogen, Q and W are carbon; X is a member selected from carbon and nitrogen; Y is a member selected from —$(CH_2)_n$—C(O)—$NR^5$—, —$(CH_2)_n$—$NR^5$—C(O)—, —$(CH_2)_n$—$CR^6R^7NR^5C(O)$—, —$(CH_2)_n$—$S(O)_2$—$NR^5$— and —$(CH_2)_n$—$NR^5$—$S(O)_2$—, wherein n is an integer selected from 0, 1, 2, 3, 4, 5 and 6; $R^5$, $R^6$ and $R^7$ are members independently selected from H, substituted or unsubstituted $C_1$-$C_7$ alkyl group, substituted or unsubstituted aryl and substituted or unsubstituted arylalkyl; $R^1$ and $R^2$ are members independently selected from H, $C_1$-$C_7$ substituted or unsubstituted alkyl, CN, $CF_3$, $OCF_3$, $SCF_3$, halogen, thioalkyl, $S(O)R^8$, $S(O)_2R^8$, $C(O)R^8$, $C(O)_2R^8$, substituted or unsubstituted benzyl, substituted or unsubstituted phenyl and substituted or unsubstituted heteroaryl, wherein $R^8$ is a member selected from H, substituted or unsubstituted $C_1$-$C_7$ alkyl, substituted or unsubstituted benzyl, substituted or unsubstituted phenyl and substituted or unsubstituted heteroaryl; $R^3$ is a member selected from the group consisting of $CF_3$, —$(CH_2)_mCF_3$, substituted or unsubstituted $C_1$-$C_9$ alkyl; substituted or unsubstituted aryl, substituted or unsubstituted heteroaryl and substituted or unsubstituted $C_3$-$C_8$ cycloalkyl, wherein m is an integer selected from 0, 1, 2, 3, 4, 5 and 6; $R^4$ is a member selected from substituted or unsubstituted $C_1$-$C_9$ alkyl, substituted or unsubstituted aryl, substituted or unsubstituted heteroaryl, substituted or unsubstituted $C_3$-$C_9$ cyclo or bicyclo alkyl and —$(CH_2)_pCF_3$, wherein p is an integer selected from 0, 1, 2, 3, 4, 5 and 6.

In some embodiments, the compounds of Formula (I) have Formula (II):

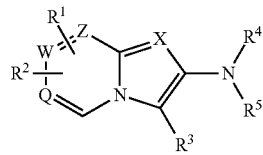

(II)

wherein Q, W, Z are members independently selected from carbon or nitrogen, with the proviso that when Q is nitrogen, W and Z are carbon; with the further proviso that when W is nitrogen, Q and Z are carbon; with the further proviso that when Z is nitrogen, Q and W are carbon; X is a member selected from carbon and nitrogen; $R^1$ and $R^2$ are members independently selected from H, $C_1$-$C_7$ substituted or unsubstituted alkyl, CN, $CF_3$, $OCF_3$, $SCF_3$, halogen, thioalkyl, $S(O)R^9$, $S(O)_2R^9$, $C(O)R^9$, $C(O)_2R^9$, substituted or unsubstituted benzyl, substituted or unsubstituted phenyl and substituted or unsubstituted heteroaryl, wherein $R^9$ is a member selected from H and substituted or unsubstituted $C_1$-$C_7$ alkyl; $R^3$ is a member selected from $CF_3$, —$(CH_2)_mCF_3$, substituted or unsubstituted $C_1$-$C_9$ alkyl, substituted or unsubstituted aryl, substituted or unsubstituted heteroaryl, substituted or unsubstituted $C_3$-$C_9$ cycloalkyl and substituted or unsubstituted $C_3$-$C_9$ bicycloalkyl; wherein m is an integer selected from 0, 1, 2, 3, 4, 5 and 6; $R^4$ is a member selected from the group consisting of H, substituted or unsubstituted $C_1$-$C_8$ alkyl, substituted or unsubstituted aryl, substituted or unsubstituted heteroaryl, substituted or unsubstituted $C_3$-$C_8$ cycloalkyl, $S(O)_2R^{10}$ and —$(CH_2)_pCF_3$, wherein p is an integer selected from 0, 1, 2, 3, 4, 5 and 6; $R^{10}$ is a member selected from substituted or unsubstituted $C_1$-$C_8$ alkyl, —$(CH_2)_t$-substituted or unsubstituted aryl, —$(CH_2)_t$-substituted or unsubstituted heteroaryl, —$(CH_2)_t$-substituted or unsubstituted $C_3$-$C_9$ cycloalkyl and —$(CH_2)_t$-substituted or unsubstituted $C_3$-$C_9$ bicycloalkyl, wherein t is an integer selected from 0, 1, 2, 3, 4, 5 and 6; $R^5$ is a member selected from substituted or unsubstituted —(CO)—$C_1$-$C_9$ alkyl, substituted or unsubstituted —(CO)—$C_1$-$C_9$ alkyl, —$(CH_2)_s$—substituted or unsubstituted aryl, —(CO)—$(CH_2)_s$-substituted or unsubstituted aryl, —(CO)—$(CH_2)_s$-substituted or unsubstituted heteroaryl, —(CO)—$(CH_2)_s$-substituted or unsubstituted heteroaryl and —(CO)—$(CH_2)_s$-substituted or unsubstituted $C_3$-$C_9$ cycloalkyl, wherein s is an integer selected from 0, 1, 2, 3, 4, 5 and 6.

In a first group of embodiments of the compounds having Formula (II), Q, W and Z are carbon and are substituted or unsubstituted.

Within the first group of embodiments or Formula (II), the present invention provides a second group of embodiments of compounds, in which Q, W and Z are carbon and each are independently substituted by one or more groups selected from halogen, nitrile, substituted or unsubstituted $C_1$-$C_4$ alkyl, trifluoromethyl and trifluoromethoxy.

Within the first, second group of embodiments or Formula (II), the invention provides a third group of embodiments of compounds, having Formula (III):

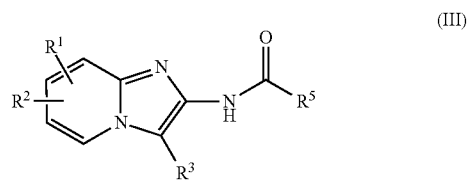

(III)

wherein $R^1$ and $R^2$ are members independently selected from H, halogen, CN, $CF_3$ and $OCF_3$; $R^3$ is a member selected from —$CH_3$, —$CH_2CH_3$, —$CH=CH_2$—, —$CH_2$cyclopropyl, cyclopropyl, —$CH_2CF_3$ and substituted or unsubstituted phenyl; $R^5$ is a member selected from substituted or unsubstituted $C_1$-$C_9$ alkyl, substituted or unsubstituted —O—$C_1$-$C_9$ alkyl, —$(CH_2)_s$-substituted or unsubstituted aryl, —O—$(CH_2)_s$-substituted or unsubstituted aryl, —$(CH_2)_s$-substituted or unsubstituted heteroaryl, —O—$(CH_2)_s$-substituted or unsubstituted heteroaryl, —$(CH_2)_s$-substituted or unsubstituted $C_3$-$C_9$ cycloalkyl and —O—$(CH_2)_s$-substituted or unsubstituted $C_3$-$C_9$ cycloalkyl, wherein s is an integer selected from 0, 1, 2, 3, 4, 5 and 6.

Within the first, second or third group of embodiments or Formulas (II) or (III), the invention provides a fourth group of embodiments of the compounds, having formula (IV):

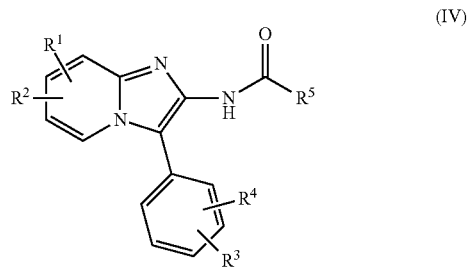

(IV)

wherein $R^1$ and $R^2$ are members independently selected from —$CF_3$ and halogen; $R^3$ and $R^4$ are members independently selected from H, —$CF_3$ and halogen; $R^5$ is a member selected from substituted or unsubstituted $C_1$-$C_9$ alkyl, substituted or unsubstituted —O—$C_1$-$C_9$ alkyl, —$(CH_2)_s$-substituted or unsubstituted aryl, —O—$(CH_2)_s$-substituted or unsubstituted aryl, —$(CH_2)_s$-substituted or unsubstituted heteroaryl, —O—$(CH_2)_s$-substituted or unsubstituted heteroaryl, —$(CH_2)_s$-substituted or unsubstituted $C_3$-$C_9$ cycloalkyl and —O—$(CH_2)_s$-substituted or unsubstituted $C_3$-$C_9$ cycloalkyl, wherein s is an integer selected from 0, 1, 2, 3, 4, 5 and 6.

In some embodiments, the present invention provides a compound of Formula (V)

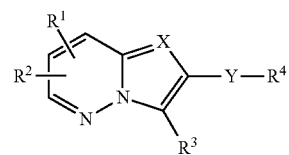

(V)

or a pharmaceutically acceptable salt, hydrate, solvate or complex thereof, wherein: X is Nitrogen; Y is a member selected from the group —$(CH_2)_n$—C(O)—$NR_5$—, —(CH$_2$)$_n$—NR$_5$—C(O)—, —(CH$_2$)$_n$—CR$_6$R$_7$NR$_5$C(O)—, —(CH$_2$)$_n$—S(O)$_2$—NR$_5$—, —(CH$_2$)$_n$—NR$_5$—S(O)$_2$—; wherein R$_5$, R$_6$ and R$_7$ are a member selected from H, substituted or unsubstituted C$_1$-C$_7$ alkyl group and n is an integer from 0-6, substituted or unsubstituted aryl, substituted or unsubstituted alkyl aryl; R$_1$ and R$_2$ are independently H, C$_1$-C$_7$ substituted or unsubstituted alkyl, CN, CF$_3$, OCF$_3$, SCF$_3$, halogen, thioalkyl, S(O)R$_8$S(O)$_2$R$_8$, C(O)R$_8$, C(O)$_2$R$_8$, optimally substituted benzyl, phenyl or heteroaryl; wherein R$_8$ is a member selected from the group consisting of —H and a substituted or unsubstituted C$_1$-C$_7$ alkyl, optimally substituted benzyl, phenyl or heteroaryl; group; R$_3$ is a member selected from the group consisting of CF$_3$, (CH$_2$)$_n$CF$_3$, wherein n is an integer from 0-6, substituted or unsubstituted C$_1$-C$_8$ alkyl, substituted or unsubstituted aryl, substituted or unsubstituted heteroaryl, substituted or unsubstituted C$_3$-C$_8$ cycloalkyl; R$_4$ is a member selected from the group consisting of substituted or unsubstituted C$_1$-C$_9$ alkyl, substituted or unsubstituted aryl, substituted or unsubstituted heteroaryl, substituted or unsubstituted C$_3$-C$_9$ cyclo or bicyclo alkyl, or (CH$_2$)$_n$CF$_3$, wherein n is an integer from 0-6.

Within Formula (V), the invention provides a first group of embodiments of compounds, having Formula (VI):

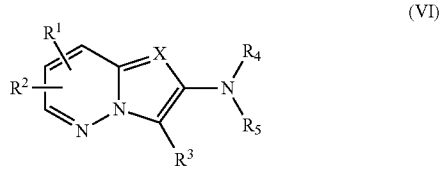

(VI)

In which: R$_1$ and R$_2$ are independently —H, C$_1$-C$_7$ substituted or unsubstituted alkyl, CN, CF$_3$, OCF$_3$, SCF$_3$, halogen, thioalkyl, S(O)R$_9$S(O)$_2$R$_9$, C(O)R$_9$, C(O)$_2$R$_9$, optimally substituted benzyl, phenyl or heteroaryl; wherein R$_9$ is a member selected from substituted or unsubstituted C$_1$-C$_7$ alkyl group; R$_3$ is a member selected from the group consisting of CF$_3$, —(CH$_2$)$_n$CF$_3$, wherein n is an integer from 0-6, substituted or unsubstituted C$_1$-C$_9$ alkyl, substituted or unsubstituted aryl, substituted or unsubstituted heteroaryl, substituted or unsubstituted C$_3$-C$_9$ cyclo or bicycloalkyl; R$_4$ is a member selected from the group consisting of H, substituted or unsubstituted C$_1$-C$_8$ alkyl, substituted or unsubstituted aryl, substituted or unsubstituted heteroaryl, substituted or unsubstituted C$_3$-C$_8$ cycloalkyl, S(O)$_2$R$_{10}$ or —(CH$_2$)$_n$CF$_3$ wherein n is an integer from 0-6 and R$_{10}$ is a member selected from substituted or unsubstituted C$_1$-C$_8$ alkyl, —(CH$_2$)$_n$-substituted or unsubstituted aryl, —(CH$_2$)$_n$-substituted or unsubstituted heteroaryl, —(CH$_2$)$_n$-substituted or unsubstituted C$_3$-C$_9$ cyclo or bicycloalkyl; R$_5$ is a member selected from substituted or unsubstituted —(CO)—C$_1$-C$_9$ alkyl, substituted or unsubstituted —(CO)—C$_1$-C$_9$ alkyl, —(CH$_2$)$_n$-substituted or unsubstituted aryl, —(CO)—(CH$_2$)$_n$-substituted or unsubstituted aryl, —(CO)—(CH$_2$)$_n$-substituted or unsubstituted heteroaryl, —(CO)—(CH$_2$)$_n$-substituted or unsubstituted heteroaryl, —(CO)—(CH$_2$)$_n$-substituted or unsubstituted C$_3$-C$_9$ cycloalkyl.

Within the compounds having Formulas (V) or (VI), the invention provides a second group of embodiments of compounds, in which R$_1$ and R$_2$ are groups selected from halogen, nitrile, substituted or unsubstituted C$_1$-C$_4$ alkyl, trifluoromethyl and trifluoromethoxy.

Within the compounds having Formulas (V) or (VI) or the second group of embodiments, the invention provides a third group of embodiments of compounds, having Formula (VII):

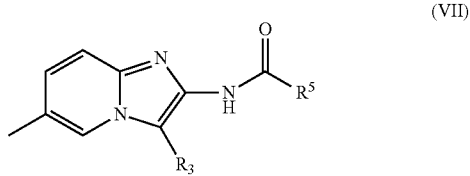

(VII)

In which R$_3$ is a member selected from —CH$_3$, —CH$_2$CH$_3$, —CH═CH$_2$—CH$_2$cyclopropyl, cyclopropyl or —CH$_2$CF$_3$; substituted or unsubstituted phenyl; R$_5$ is a member selected from substituted or unsubstituted C$_1$-C$_9$ alkyl, substituted or unsubstituted —O—C$_1$-C$_9$ alkyl, —(CH$_2$)$_n$-substituted or unsubstituted aryl, —O—(CH$_2$)$_n$-substituted or unsubstituted aryl, —(CH$_2$)$_n$-substituted or unsubstituted heteroaryl, —O—(CH$_2$)$_n$-substituted or unsubstituted heteroaryl, —(CH$_2$)$_n$-substituted or unsubstituted C$_3$-C$_9$ cycloalkyl, —O—(CH$_2$)$_n$-substituted or unsubstituted C$_3$-C$_9$ cycloalkyl.

Within the compounds having Formulas (V), (VI) or (VII) or the second group of embodiments, the invention provides a fourth group of embodiments of compounds, having the Formula (VIII)

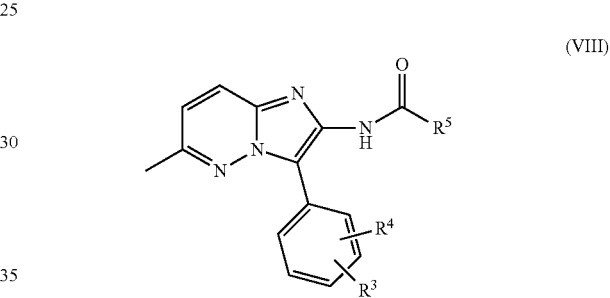

(VIII)

In which R$_3$ and R$_4$ are independently —H, —CF$_3$, —OCF$_3$ or halogen; R$_5$ is a member selected from substituted or unsubstituted C$_1$-C$_9$ alkyl, substituted or unsubstituted —O—C$_1$-C$_9$ alkyl, —(CH$_2$)$_n$-substituted or unsubstituted aryl, —O—(CH$_2$)$_n$-substituted or unsubstituted aryl, —(CH$_2$)$_n$-substituted or unsubstituted heteroaryl, —O—(CH$_2$)$_n$-substituted or unsubstituted heteroaryl, —(CH$_2$)$_n$-substituted or unsubstituted C$_3$-C$_9$ cycloalkyl, —O—(CH$_2$)$_n$-substituted or unsubstituted C$_3$-C$_9$ cycloalkyl.

In one group of embodiments, the present invention provide a compound of Formula (IX):

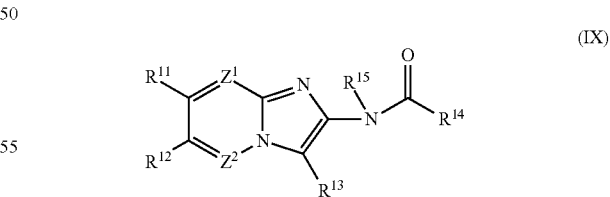

(IX)

or a pharmaceutically acceptable salt, hydrate or solvate thereof. In one instance, R$^{15}$ is —H.

In Formula (IX), R$^{11}$ and R$^{12}$ are each independently selected from the group consisting of —H, halogen, C$_{1-8}$haloalkyl, —CN, C$_{1-8}$alkyl, C$_{1-8}$alkoxy, aryloxy an—d aryl-C$_{1-8}$alkoxy. In one group of embodiments of compounds having Formula (IX), R$^{11}$ is —H, —CH$_3$, —CF$_3$, —CN, —OCH$_3$, —Cl, PhO—, Ph-CH$_2$CH$_2$O— or PhCH$_2$O—. In another group of embodiments of compounds having Formula (IX), $R^{11}$ is —H, —CH$_3$, —CF$_3$, —CN, —OCH$_3$, or —Cl. In yet another group embodiments of compounds having formula (IX), $R^{12}$ is —H, —F, —Cl, —Br, —CN, —CH$_3$, —CF$_3$, PhO—, Ph-CH$_2$CH$_2$O— or PhCH$_2$O—. In still another embodiments of compounds having Formula (IX), $R^{12}$ is —H, —F, —Cl, —Br, —CN, —CH$_3$, —CF$_3$, or —OCH$_3$. In some embodiments of compounds having Formula (IX), $R^{11}$ is —H, —CH$_3$, —CF$_3$, —CN, —OCH$_3$, —Cl, PhO—, Ph-CH$_2$CH$_2$O— or PhCH$_2$O— and $R^{12}$ is —H, —F, —Cl, —Br, —CN, —CH$_3$, —CF$_3$, —OCH$_3$, PhO—, Ph-CH$_2$CH$_2$O— or PhCH$_2$O—. In certain instances, $R^{12}$ is —H. In other instances, $R^{11}$ and $R^{12}$ are —H.

In Formula (IX), $R^{13}$ is selected from the group consisting of —H, C$_{1-8}$alkyl, C$_{2-8}$alkenyl, aryl, C$_{3-8}$cycloalkyl, aryl-C$_{1-6}$alkyl, C$_{3-8}$cycloalkyl-C$_{1-8}$alkyl, heteroaryl and heteroaryl-C$_{1-6}$alkyl, wherein the aromatic portion of the $R^{13}$ group is optionally substituted with from 1-3 R$^a$ substituents, each R$^a$ is independently selected from the group consisting of halogen, C$_{1-8}$haloalkoxy, C$_{1-8}$alkoxy, C$_{1-8}$haloalkyl, —CN and R$^b$, wherein R$^b$ is C$_{1-8}$alkyl optionally substituted with from 1-2 substituents selected from halogen, —CN, —OH, C$_{1-8}$haloalkoxy or C$_{1-8}$alkoxy; or any two adjacent R$^a$ substituents together with the atoms to which they are attached form a 5- or 6-membered carbocyclic ring, optionally substituted with a C$_{1-8}$alkyl.

In one group of embodiments of compounds having Formula (IX), $R^{13}$ is selected from the group consisting of —H, C$_{2-8}$alkenyl, aryl, C$_{3-8}$cycloalkyl, aryl-C$_{1-6}$alkyl, C$_{3-8}$cycloalkyl-C$_{1-8}$alkyl and 5- or 6-membered heteroaryl having from 1-3 heteroatoms as ring members selected from N, O or S, wherein the aryl or heteroaryl moiety of the $R^{13}$ group is optionally substituted with from 1-3 R$^a$ substituents, each R$^a$ is independently selected from the group consisting of halogen, —OCF$_3$, C$_{1-8}$alkoxy, —CF$_3$, —CN, hydroxy-C$_{1-8}$alkyl, C$_{1-8}$alkoxy-C$_{1-8}$alkyl, C$_{1-8}$haloalkyl, cyano-C$_{1-8}$alkyl, C$_{1-8}$haloalkoxy-C$_{1-8}$alkyl; or optionally any two adjacent R$^a$ substituents together with the atoms to which they are attached form a 5- or 6-membered carbocyclic ring, optionally substituted with a C$_{1-8}$alkyl. In certain instances, the carbocyclic ring is a benzene ring, a cyclopentane or cyclohexane ring.

In another group of embodiments of compounds having Formula (IX), $R^{13}$ is selected from the group consisting of: i) —H, halogen, C$_{1-8}$alkyl, C$_{2-8}$alkenyl, C$_{3-8}$cycloalkyl, C$_{3-8}$cycloalkyl-C$_{1-8}$alkyl; ii) phenyl, benzyl, 2-pyridyl, 3-pyridyl, 4-pyridyl, 2-pyrizinyl, 3-pyridazinyl, 4-pyridazinyl, 2-pyrimidinyl or 1,3,5-triazin-2-yl, each of which is optionally substituted with from 1-3 substituents independently selected from —F, Br, Cl, I, —CH$_3$, C$_{1-8}$alkyl, isopropyl, —CF$_3$, —CN, —C(CH$_3$)$_2$CN, —OCF$_3$, C$_{1-4}$alkoxy or —CHF$_2$; and iii) 2-thiazolyl, 4-thiazolyl, 5-thiazolyl, 2-benzothiazolyl, 3-pyrazolyl, 4-pyrazolyl, 5-pyrazolyl, each of which is optionally substituted with a C$_{1-8}$alkyl.

In yet another group of embodiments of compounds having Formula (IX), $R^{13}$ is $R^{13}$ is selected from the group consisting of —H, Cl, Br, —I, —CH$_3$, vinyl, phenyl, 2-fluorophenyl, 3-fluorophenyl, 4-fluorophenyl, 2,4-difluorophenyl, 2,3-difluorophenyl, 2,5-difluorophenyl, 2,6-difluorophenyl, 2-trifluoromethylphenyl, 3-trifluoromethylphenyl, 4-trifluoromethylphenyl, 2-chlorophenyl, 3-chlorophenyl, 4-chlorophenyl, 2-trifluoromethylphenyl, 3-trifluoromethylphenyl, 4-trifluoromethylphenyl, 2-trifluoromethoxyphenyl, 3-trifluoromethoxyphenyl, 4-trifluoromethoxyphenyl, 2-pyridyl, 3-pyridyl, 4-pyridyl, cyclopropyl, 2,2-dimethylpropyl, 2-fluorobenzyl, 3-fluorobenzyl, 4-fluorobenzyl, 3-(2-cyanopropan-2-yl)phenyl, 4-(2-cyanopropan-2-yl)phenyl, 6-fluoro-3-pyridyl, 2-fluoro-3-pyridyl, 4-fluoro-3-pyridyl, 5-fluoro-3-pyridyl, 6-cyano-3-pyridyl, 2-cyano-3-pyridyl, 4-cyano-3-pyridyl, 5-cyano-3-pyridyl, 2-cyanophenyl, 3-cyanophenyl, 4-cyanophenyl, 6-fluoro-2-pyridyl, 3-fluoro-2-pyridyl, 4-fluoro-2-pyridyl, 5-fluoro-2-pyridyl, 6-trifluoromethyl-2-pyridyl, 3-trifluoromethyl-2-pyridyl, 4-trifluoromethyl-2-pyridyl, 5-trifluoromethyl-2-pyridyl, 3-difluoromethyl-4-fluorophenyl, 3-difluoromethyl-5-fluorophenyl, 3-fluoro-4-difluoromethylphenyl, 3-fluoro-4-trifluoromethoxyphenyl, 3-fluoro-5-trifluoromethoxyphenyl, 3-fluoro-4-cyanophenyl, 3-fluoro-5-cyanoyphenyl, 3-fluoro-4-trifluoromethylphenyl, 3-fluoro-5-trifluoromethylphenyl, 3-trifluoromethyl-4-fluorophenyl, 3-trifluoromethyl-4-methoxyphenyl, 3-trifluoromethyl-5-methoxyphenyl, 3-methoxy-4-trifluoromethylphenyl, 3-fluoro-4-methylphenyl, 3-fluoro-5-methylphenyl, 3-methyl-4-fluorophenyl, 4-trifluoromethyl-3-pyridyl, 5-trifluoromethyl-3-pyridyl, 6-trifluoromethyl-3-pyridyl, 5-methyl-2-pyridyl, 3-methyl-2-pyridyl, 4-methyl-2-pyridyl, 6-methyl-2-pyridyl, benzothiazol-2-yl, 3,4-difluorophenyl, 3-5-difluorophenyl, 2-pyrimidinyl, 3-methyl-4-fluorophenyl, 3-methyl-5-fluorophenyl, 3-fluoro-4-methylphenyl, 3,5-difluoro-4-methylphenyl, 3-methyl-4-chlorophenyl, 3-methyl-5-chlorophenyl, 3-chloro-4-methylphenyl, 3-chloro-2-pyridyl, 4-chloro-2-pyridyl, 5-chloro-2-pyridyl, 6-chloro-2-pyridyl, 3-methoxy-2-pyridyl, 4-methoxy-2-pyridyl, 5-methoxy-2-pyridyl, 6-methoxy-2-pyridyl, 1-isopropyl-4-pyrazolyl, cyclohexylmethyl, cyclohexyl, 3-methyl-1-butyl, cyclopentyl, 2-thiazolyl, 4-thiazolyl, 5-thiazolyl, 2-methyl-4-thiazolyl, 5-methyl-2-thiazolyl and 4-methyl-2-thiazolyl.

In a preferred group of embodiments of compounds having Formula (IX), $R^{13}$ is C$_{1-8}$alkyl, C$_{3-8}$cycloalkyl or C$_{3-8}$cycloalkyl-C$_{1-4}$alkyl. In certain instances, $R^{13}$ is 2-methylbutyl, 2,2-dimethylpropyl, cyclopropylmethyl, cyclobutylmethyl, cyclopentylmethyl, cyclohexylmethyl, cyclopropyl, cyclobutyl, cyclopentyl, cyclohexyl, t-butyl or isobutyl. In other instances, $R^{13}$ is 2-methylbutyl, 2,2-dimethylpropyl, cyclopropylmethyl, cyclobutylmethyl, cyclopentylmethyl, cyclohexylmethyl, cyclopropyl, cyclobutyl, cyclopentyl, or t-butyl.

In Formula (IX), $R^{14}$ is selected from the group consisting of C$_{1-8}$alkyl, C$_{1-8}$haloalkyl, C$_{3-8}$cycloalkyl, C$_{3-8}$cycloalkyl-C$_{1-8}$alkyl, aryl, aryl-C$_{1-8}$alkyl, C$_{1-8}$alkoxy, aryl-C$_{1-8}$alkoxy, C$_{4-5}$heterocycloalkyl, C$_{4-5}$heterocycloalkyl-C$_{1-8}$alkyl, R$^c$, —NHR$^d$ and —N(R$^d$)$_2$, wherein R$^c$ is C$_{1-8}$alkyl substituted with from 1-2 members selected from —OH, —OC(O)C$_{1-8}$alkyl, —CH$_2$N(R$^d$)$_2$, —OC(O)aryl, C$_{1-8}$alkoxy or aryloxy and R$^d$ is C$_{1-8}$alkyl or aryl-C$_{1-8}$alkyl, wherein the aromatic portion of the R$^{14}$ group is optionally substituted with from 1-3 R$^e$ substituents independently selected from the group consisting of halogen, C$_{1-8}$haloalkyl, C$_{1-8}$alkyl, C$_{1-8}$alkoxy, —CN or haloalkoxy, —OH, —OC(O)O—R$^f$, —OC(O)R$^f$, —OC(O)NHR$^f$, —OC(O)N(R$^f$)$_2$, —S(O)R$^f$, —S(O)$_2$R$^f$, —SO$_2$NH$_2$, —S(O)$_2$NHR$^f$, —S(O)$_2$N(R$^f$)$_2$, —NHS(O)$_2$R$^f$, —NR$^f$S(O)$_2$R$^f$, —C(O)NH$_2$, —C(O)NHR$^f$, —C(O)N(R$^f$)$_2$, —C(O)R$^f$, —C(O)H, wherein each R$^f$ is independently a C$_{1-8}$alkyl; and the cycloalkyl portion of the R$^{14}$ group is optionally substituted with from 1-3 substituents selected from halogen, C$_{1-8}$alkyl or optionally fused with a 5- or 6-membered aromatic ring having from 0-2 heteroatoms as ring members selected from N, O or S.

In one group of embodiments of the compounds having Formula (IX), $R^{14}$ is selected from the group consisting of C$_{1-8}$alkyl, C$_{1-8}$haloalkyl, C$_{3-8}$cycloalkyl, C$_{3-8}$cycloalkyl-C$_{1-8}$alkyl, aryl-C$_{1-8}$alkyl, C$_{1-8}$alkoxy, aryl-C$_{1-8}$alkoxy, C$_{4-5}$heterocycloalkyl, C$_{4-5}$heterocycloalkyl-C$_{1-8}$alkyl, hydroxyl-C$_{1-8}$alkyl, C$_{1-8}$alkyl-C(O)O—C$_{1-8}$alkyl, aryl-C(O)O—C$_{1-8}$alkyl, C$_{1-8}$alkoxy-C$_{1-8}$alkyl or aryloxy-C$_{1-8}$alkyl, ($R^d$)$_2$NCH$_2$—C$_{1-8}$alkyl, —NHR$^d$ and —N(R$^d$)$_2$, wherein R$^d$ is C$_{1-8}$alkyl or aryl-C$_{1-8}$alkyl; wherein the aromatic portion of the R$^{14}$ group is optionally substituted with from 1-3 substituents selected from the group consisting of halogen, C$_{1-8}$haloalkyl, C$_{1-8}$alkyl, C$_{1-8}$alkoxy, —CN or haloalkoxy and the cycloalkyl portion of the R$^{14}$ group is optionally substituted with from 1-3 substituents selected from halogen, C$_{1-8}$alkyl or optionally fused with a 5- or 6-membered aromatic ring having from 0-2 heteroatoms as ring members selected from N, O or S.

In another group of embodiments of the compounds having Formula (IX), R$^{14}$ is selected from the group consisting of C$_{1-8}$alkyl, C$_{1-8}$haloalkyl, C$_{1-8}$alkoxy, C$_{4-5}$heterocycloalkyl, C$_{4-5}$heterocycloalkyl-C$_{1-8}$alkyl, hydroxyl-C$_{1-8}$alkyl, C$_{1-8}$alkyl-C(O)O—C$_{1-8}$alkyl, C$_{1-8}$alkoxy-C$_{1-8}$alkyl, —NH(C$_{1-8}$alkyl) and —N(C$_{1-8}$alkyl)$_2$, phenyl, phenyl-C$_{1-8}$alkyl, phenyl-C$_{1-8}$alkoxy, phenyl-C(O)O—C$_{1-8}$alkyl, phenoxy-C$_{1-8}$alkyl or (phenyl-C$_{1-8}$alkyl)NH—, C$_{3-8}$cycloalkyl and C$_{3-8}$cycloalkyl-C$_{1-8}$alkyl, wherein each phenyl moiety is optionally substituted with from 1-3 members independently selected from halogen, —CF$_3$, —CN, —C$_{1-8}$alkyl or —C$_{1-8}$alkoxy; and each cycloalkyl moiety is optionally substituted with 1-2 substituents selected from halogen and C$_{1-8}$alkyl or optionally fused with a phenyl ring. In certain instances, R$^{14}$ is selected from the group consisting of —CH$_3$, —CF$_3$, 4-fluorophenyl, 3,4-difluorophenyl, benzyl, 2-fluorobenzyl, 3-fluorobenzyl, 4-fluorobenzyl, 2,2-dimethylpropyl, 2,2,2-trifluoroethyl, 3,3,3-trifluoropropyl, cyclopentylmethyl, Ph(CH$_3$)CH$_2$—, cyclopropylmethyl, cyclohexylmethyl, 2-methoxybenzyl, 3-methoxybenzyl, 4-methoxybenzyl, PhCH$_2$CH$_2$—, 2-trifluoromethylbenzyl, 3-trifluoromethylbenzyl, 4-trifluoromethylbenzyl, 2-cyanobenzyl, 3-cyanobenzyl, 4-cyanobenzyl, 3,4-difluorobenzyl, 3,5-difluorobenzyl, 3,6-difluorobenzyl, 2,6-difluorobenzyl, 2,4,4-trimethylpentyl, 2-fluoro-6-chloro-benzyl, 2-fluoro-3-chloro-benzyl, 2-fluoro-4-chloro-benzyl, 2-fluoro-5-chloro-benzyl, 3-fluoro-4-chlorobenzyl, 3-fluoro-5-chlorobenzyl, 3-fluoro-6-chlorobenzyl, 3,4-dichlorobenzyl, 3,5-dichlorobenzyl, 3,6-dichlorobenzyl, 2,6-dichlorobenzyl, 2-methylbenzyl, 3-methylbenzyl, 4-methylbenzyl, 2-chlorobenzyl, 3-chlorobenzyl, 4-chlorobenzyl, 2-methyl-3,3,3-trifluoropropyl, benzyloxy, 2-methylbutyl, CN—CH$_2$CH$_2$CH$_2$—, (CH$_3$)$_2$CHCH(CH$_3$)—, 3,3-dimethylbutyl, cyclopropylethyl, 4,4,4-trifluorobutyl, (bicyclo[2.2.1]heptan-2-yl)methyl, (1-methylcyclohexyl)methyl, (1-methylcyclopentyl)methyl, (CH$_3$)$_3$CCH(OH)—, cyclobutylmethyl, CH$_3$C(O)OCH$_2$C(CH$_3$)$_2$CH$_2$—, (OH)CH$_2$C(CH$_3$)$_2$CH$_2$—, 1,1-difluoro-2,2-dimethylpropyl, t-butoxymethyl, t-butoxyethyl, 2-(4-fluorophenyl)ethylamino, 4-fluorobenzylamino, t-butylamino, 2-cyano-2-methylpropyl, cyclopentylethyl, Ph-O—CH$_2$—, Ph-O—CH(CH$_3$)—, 4-phenoxybenzyl, PhCH$_2$OCH$_2$—, 2-tetrahydropyranyl, 3,4-dichlorophenoxymethyl, 3,5-dichlorophenoxymethyl, 3,6-dichlorophenoxymethyl, 2,3-dichlorophenoxymethyl, 2,4-dichlorophenoxymethyl, 2,5-dichlorophenoxymethyl, 2,6-dichlorophenoxymethyl, 2-fluorophenoxyethyl, 3-fluorophenoxyethyl, 4-fluorophenoxyethyl, (tetrahydropyran-4-yl)methyl, 3,3-dimethylbutyl, 2-trifluoromethoxybenzyl, 3-trifluoromethoxybenzyl, 4-trifluoromethoxybenzyl, cyclopropyl, cyclobutyl, cyclopentyl, cyclohexyl, cyclooctyl, cycloheptyl, 2-indanyl, 1-indanyl, isobutyl, 3,3-difluorocyclopentylmethyl, 4,4-difluorocyclohexyl, 2,2-difluorocyclopropyl, (R)—CF$_3$CH(CH$_3$)CH$_2$—, (S)—CF$_3$CH(CH$_3$)CH$_2$—, CH$_3$C(O)OCH(t-butyl)-, HOCH(t-butyl)-, 2-tetrahydrofuranyl,

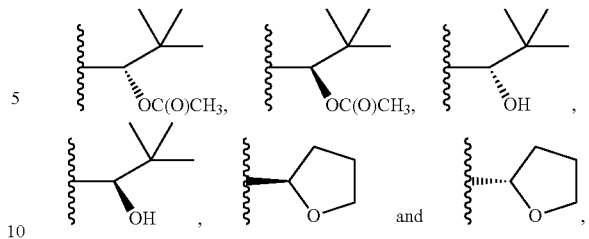

wherein the wavy line indicates the point of attachment to the rest of the molecule.

In a preferred group of embodiments of the compounds having Formula (IX), R$^{14}$ is aryl-C$_{1-4}$alkyl, C$_{1-6}$alkyl, C$_{3-8}$cycloalkyl, C$_{3-8}$cycloalkyl-C$_{1-4}$alkyl, aryl or C$_{4-5}$cycloalkyl, wherein the aryl moiety is substituted with from 1-2 substituents selected from —F, —CF$_3$ or —OCF$_3$ and the alkyl portion of the R$^{14}$ is optionally substituted with from 1-2 substituents selected from —F or —CF$_3$. In certain instances, R$^{14}$ is selected from the group consisting of 3,4-difluorobenzyl, cyclobutyl, —CH(s-OH)-t-Bu, —CH$_2$CH(CF$_3$)CH$_3$, (R)—CH$_2$CH(CF$_3$)CH$_3$, (S)—CH$_2$CH(CF$_3$)CH$_3$, —CH$_2$CH(CF$_3$)CH$_3$, cyclohexylmethyl, —CH(CH$_3$)CH(CH$_3$)$_2$, 4-fluorobenzyl, 3-fluorobenzyl, cyclobutylmethyl, —CH$_2$CH$_2$-t-Bu, 4-fluorophenyl, 3,4-difluorophenyl, —CH(CH$_3$)-t-Bu, (R)-2-tetrahydrofuranyl, —CH$_2$CH(CH$_3$)CF$_3$, cyclopentyl, —CH$_2$CH$_2$CF$_3$, 3,3-difluorocyclopentylmethyl, 4,4-difluorocyclohexyl and 2,2-difluorocyclopropyl.

In another preferred group of embodiments, R$^{13}$ is 2-methylbutyl, 2,2-dimethylpropyl, cyclopropylmethyl, cyclobutylmethyl, cyclopentylmethyl, cyclohexylmethyl or isobutyl and R$^{14}$ is selected from the group consisting of 3,4-difluorobenzyl, cyclobutyl, —CH(s-OH)-t-Bu, —CH$_2$-t-Bu, —CH$_2$CH(CF$_3$)CH$_3$, (R)—CH$_2$CH(CF$_3$)CH$_3$, (S)—CH$_2$CH(CF$_3$)CH$_3$, —CH$_2$CH(CF$_3$)CH$_3$, cyclohexylmethyl, —CH(CH$_3$)CH(CH$_3$)$_2$, 4-fluorobenzyl, 3-fluorobenzyl, cyclobutylmethyl, —C$_{1-12}$CH$_2$-t-Bu, 4-fluorophenyl, 3,4-difluorophenyl, —CH(CH$_3$)-t-Bu, (R)-2-tetrahydrofuranyl, —CH$_2$CH(C$_{1-13}$)CF$_3$, cyclopentyl, —CH$_2$CH$_2$CF$_3$, 3,3-difluorocyclopentylmethyl, 4,4-difluorocyclohexyl and 2,2-difluorocyclopropyl.

In formula (IX), Z$^1$ is =N— or =C(R$^{16}$)— and Z$^2$ is =N— or =C(R$^{17}$)—, wherein R$^{16}$ and R$^{17}$ are each independently —H, C$_{1-8}$alkyl, halogen, —CN, C$_{1-8}$haloalkyl, C$_{1-8}$haloalkoxy, —OR$^g$ or —N(R$^g$)$_2$, wherein R$^g$ is independently —H, C$_{1-8}$alkyl or aryl-C$_{1-8}$alkyl, with the proviso that Z$^1$ and Z$^2$ are not simultaneously =N—. In one group of embodiments, R$^{16}$ is selected from —H, C$_{1-8}$alkyl, C$_{1-8}$haloalkyl, C$_{1-8}$haloalkoxy, halogen, —OH, C$_{1-8}$alkoxy or aryl-C$_{1-6}$alkoxy. In certain instances, R$^{16}$ is selected from —H, —F, —CF$_3$, —OCF$_3$, —CH$_3$, —N(CH$_3$)(CH$_2$Ph), —OH, C$_{1-4}$alkoxy or benzyloxy. In another group of embodiments, R$^{17}$ is selected from —H, C$_{1-8}$alkyl, C$_{1-8}$haloalkyl, C$_{1-8}$haloalkoxy, halogen, -OH, C$_{1-8}$alkoxy or aryl-C$_{1-6}$alkoxy. In certain instances, R$^{17}$ is selected from —H, —F, —CF$_3$, —OCF$_3$, —CH$_3$, —N(CH$_3$)(CH$_2$Ph), —OH, C$_{1-4}$alkoxy or benzyloxy. In one embodiment, R$^{16}$ and R$^{17}$ are —H.

In one embodiment, R$^{11}$ and R$^{16}$ are —H. In another embodiment, R$^{11}$ and R$^{17}$ are —H. In a preferred embodiments, R$^{11}$, R$^{16}$ and R$^{17}$ are —H.

In Formula (IX), R$^{15}$ is R$^{15}$ is —H, —C$_{1-8}$alkyl or —C(O)C$_{1-8}$alkyl. In some embodiments, R$^{15}$ is —H.

In the above embodiments of compounds having Formula (IX), at each occurrence, "alkyl" by itself or as part of another substituent, is an unsubstituted, fully saturated, straight or branched chain hydrocarbon radical unless specified otherwise; at each occurrence, "cycloalkyl" by itself or as part of another substituent is an unsubstituted, fully saturated, cyclic hydrocarbon radical unless specified otherwise; and at each occurrence, "aryl" by itself or as part of another substituent is a monovalent monocyclic, bicyclic or polycyclic polyunsaturated aromatic hydrocarbon radical. In some preferred embodiments, "aryl" by itself or as part of another substituent denotes a monovalent monocyclic, bicyclic or polycyclic polyunsaturated unsubstituted aromatic hydrocarbon radical unless otherwise specified and "heteroaryl" by itself or as part of another substituent denotes unsubstituted aryl groups (or rings) that contains from one to five heteroatoms selected from N, O, or S, wherein the nitrogen and sulfur atoms are optionally oxidized, and the nitrogen atom(s) are optionally quaternized unless otherwise specified.

Subformula of Formula (IX)

In one group of embodiments, the compounds of Formula IX, or pharmaceutically acceptable salts, hydrates or solvates thereof, have a subformula (IXa):

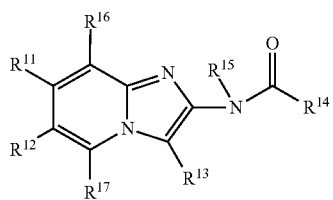

IXa wherein the substituents, $R^{11}$, $R^{12}$, $R^{13}$, $R^{14}$, $R^{15}$, $R^{16}$ and $R^{17}$ are as defined above in Formula (IX). In certain instances, wherein $R^{16}$ and $R^{17}$ are each independently —H, $C_{1-8}$alkyl, halogen, —CN, $C_{1-8}$haloalkyl, $C_{1-8}$haloalkoxy, —OR$^g$ or —N(R$^g$)$_2$, wherein R$^g$ is independently —H, $C_{1-8}$alkyl or aryl-$C_{1-8}$alkyl. In other instances, $R^{15}$ is —H. In yet other instances, $R^{11}$ is —H, —CH$_3$, —CF$_3$, —OCH$_3$, —Cl, PhO— or PhCH$_2$O— and $R^{12}$ is —H, —F, —Cl, —Br, —CN, —CH$_3$, —CF$_3$, PhO—, PhCH$_2$O— or —OCH$_3$. In certain instances, $R^{15}$ is —H. In other instances, $R^{13}$ is preferably 2-methylbutyl, 2,2-dimethylpropyl, cyclopropylmethyl, cyclobutylmethyl, cyclopentylmethyl, cyclohexylmethyl, cyclopropyl, cyclobutyl, cyclopentyl, cyclohexyl, isobutyl or t-butyl.

In a second group of embodiments, the compounds of Formula IX, or pharmaceutically acceptable salts, hydrates or solvates thereof, have a subformula (IXa-1):

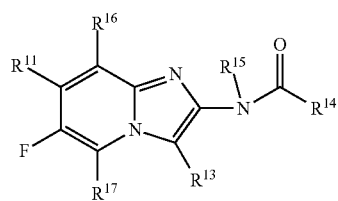

IXa-1 wherein the substituents, $R^{11}$, $R^{13}$, $R^{14}$, $R^{15}$, $R^{16}$ and $R^{17}$ are as defined above in Formula (IX). In certain instances, $R^{15}$ is —H. In certain instances, $R^{13}$ is preferably 2-methylbutyl, 2,2-dimethylpropyl, cyclopropylmethyl, cyclobutylmethyl, cyclopentylmethyl, cyclohexylmethyl, cyclopropyl, cyclobutyl, cyclopentyl, cyclohexyl, isobutyl or t-butyl.

In a third group of embodiments, the compounds of Formula IX, or pharmaceutically acceptable salts, hydrates or solvates thereof, have a subformula (IXa-2):

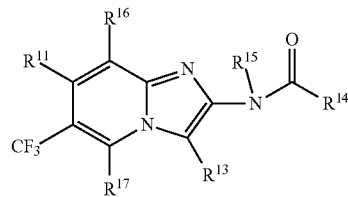

IXa-2 wherein the substituents, $R^{11}$, $R^{13}$, $R^{14}$, $R^{15}$, $R^{16}$ and $R^{17}$ are as defined above in Formula (IX). In certain instances, $R^{15}$ is —H. In certain instances, $R^{13}$ is preferably 2-methylbutyl, 2,2-dimethylpropyl, cyclopropylmethyl, cyclobutylmethyl, cyclopentylmethyl, cyclohexylmethyl, cyclopropyl, cyclobutyl, cyclopentyl, cyclohexyl, isobutyl or t-butyl.

In a fourth group of embodiments, the compounds of Formula IX, or pharmaceutically acceptable salts, hydrates or solvates thereof, have a subformula (IXa-3):

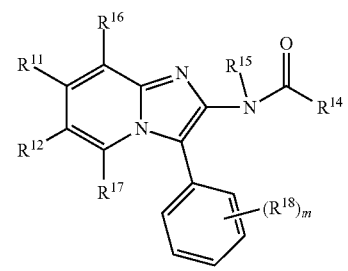

IXa-3 wherein $R^{18}$ is selected from the group consisting of halogen, $C_{1-8}$haloalkoxy, $C_{1-8}$alkoxy, $C_{1-8}$haloalkyl, —CN and R$^b$. The subscript m is an integer of 0-3. The substituents, $R^{11}$, $R^{12}$, $R^{14}$, $R^{15}$, $R^{16}$ and $R^{17}$ are as defined above in Formula (IX). In certain instances, $R^{15}$ is —H.

In a fifth group of embodiments, the compounds of Formula IX, or pharmaceutically acceptable salts, hydrates or solvates thereof, have a subformula (IXa-4):

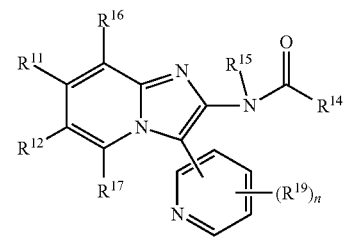

IXa-4 wherein $R^{19}$ is selected from the group consisting of halogen, $C_{1-8}$haloalkoxy, $C_{1-8}$alkoxy, $C_{1-8}$haloalkyl, —CN and R$^b$. The subscript n is an integer of 0-3. The substituents, $R^{11}$, $R^{12}$, $R^{14}$, $R^{15}$, $R^{16}$ and $R^{17}$ are as defined above in Formula (IX). In certain instances, $R^{15}$ is —H.

In a sixth group of embodiments, the compounds of Formula IX, or pharmaceutically acceptable salts, hydrates or solvates thereof, have a subformula (IXa-5):

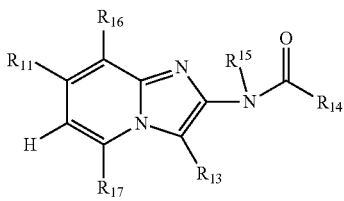

IXa-5 wherein the substituents, $R^{11}$, $R^{13}$, $R^{14}$, $R^{15}$, $R^{16}$ and $R^{17}$ are as defined above in Formula (IX). In certain instances, $R^{15}$ is —H. In certain instances, $R^{13}$ is preferably 2-methylbutyl, 2,2-dimethylpropyl, cyclopropylmethyl, cyclobutylmethyl, cyclopentylmethyl, cyclohexylmethyl, cyclopropyl, cyclobutyl, cyclopentyl, cyclohexyl, isobutyl or t-butyl In a seventh group of embodiments, the compounds of Formula IX, or pharmaceutically acceptable salts, hydrates or solvates thereof, have a subformula (IXa-6):

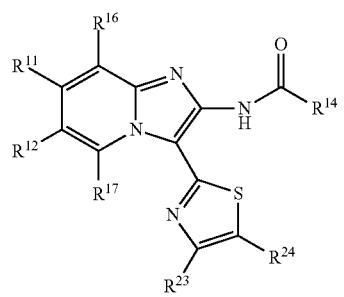

IXa-6 wherein $R^{23}$ and $R^{24}$ are each independently —H, $C_{1-8}$alkyl, halogen, $C_{1-8}$haloalkyl, —CN, —NH$_2$, —NHC$_{1-8}$alkyl, —N(C$_{1-8}$alkyl)$_2$ or $R^e$; or $R^{23}$ and $R^{24}$ are taken together with the atoms to which they are attached to form a 6-membered fused ring. In certain instances, the fused ring is a benzene ring or a pyridine ring. In other instances, $R^{23}$ and $R^{24}$ are —H. Other substituents, $R^{11}$, $R^{12}$, $R^{13}$, $R^{14}$, $R^{16}$ and $R^{17}$ are as defined above in Formula (IX).

In certain instances of the above second to the seventh groups of embodiments, $R^{11}$ is —H, —CH$_3$, —CF$_3$, —OCH$_3$, —Cl, PhO— or PhCH$_2$O— and $R^{12}$ is —H, —F, —Br, —CN, —CH$_3$, —CF$_3$, PhO—, PhCH$_2$O— or —OCH$_3$. In other instances, $R^{11}$, $R^{16}$ and $R^{17}$ are —H.

In an eighth group of embodiments, the compounds of Formula (IX), or pharmaceutically acceptable salts, hydrates or solvates thereof, have a subformula (IXa-7):

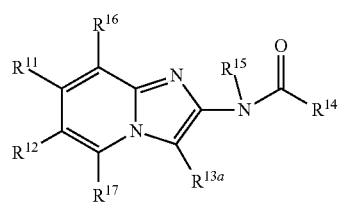

IXa-7 wherein $R^{13a}$ is selected from 2-methylbutyl, 2,2-dimethylpropyl, cyclopropylmethyl, cyclobutylmethyl, cyclopentylmethyl, cyclohexylmethyl, cyclopropyl, cyclobutyl, cyclopentyl, cyclohexyl, isobutyl or t-butyl and $R^{11}$, $R^{12}$, $R^{14}$, $R^{15}$, $R^{16}$ and $R^{17}$ are as defined above in Formula (IX). In certain instances, $R^{13a}$ is cyclopropyl, cyclobutyl, cyclopentyl, or 2,2-dimethylpropyl.

In a ninth group of embodiments, the compounds of Formula IX, or pharmaceutically acceptable salts, hydrates or solvates thereof, have a subformula (IXb):

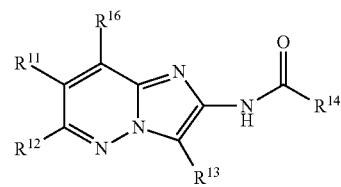

IXb wherein substituents $R^{11}$, $R^{12}$, $R^{13}$, $R^{14}$ and $R^{16}$ are as defined above in Formula (IX). In certain instances, $R^{11}$ is —H and $R^{12}$ is —Cl, —CH$_3$ or —CF$_3$. In other instances, $R^{11}$ and $R^{16}$ are —H. In yet other instances, $R^{13}$ is 2-trifluoromethylphenyl, 3-trifluoromethylphenyl, 4-trifluoromethylphenyl, 2-trifluoromethoxyphenyl, 2-trifluoromethoxyphenyl, 2-trifluoromethoxyphenyl, 2,2-dimethylpropyl, cyclopropylmethyl, cyclopropyl, 2-thiazolyl, benzothiazol-2-yl, 6-trifluoromethyl-2-pyridyl, 3-trifluoromethyl-2-pyridyl, 4-trifluoromethyl-2-pyridyl or 5-trifluoromethyl-2-pyridyl. In certain instances, $R^{13}$ is preferably 2-methyl butyl, 2,2-dimethylpropyl, cyclopropylmethyl, cyclobutylmethyl, cyclopentylmethyl, cyclohexylmethyl, cyclopropyl, cyclobutyl, cyclopentyl, cyclohexyl, isobutyl or t-butyl.

In a tenth group of embodiments, the compounds of Formula IX, or pharmaceutically acceptable salts, hydrates or solvates thereof, have a subformula (IXb-1):

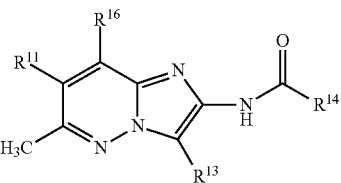

IXb-1 wherein substituents $R^{11}$, $R^{13}$, $R^{14}$ and $R^{16}$ are as defined above in Formula (IX). In certain instances, $R^{11}$ is —H. In other instances, $R^{11}$ and $R^{16}$ are —H. In yet other instances, $R^{13}$ is 2-trifluoromethylphenyl, 3-trifluoromethylphenyl, 4-trifluoromethylphenyl, 2-trifluoromethoxyphenyl, 2-trifluoromethoxyphenyl, 2-trifluoromethoxyphenyl, 2,2-dimethylpropyl, cyclopropyl methyl, cyclopropyl, 2-thiazolyl, benzothiazol-2-yl, 6-trifluoromethyl-2-pyridyl, 3-trifluoromethyl-2-pyridyl, 4-trifluoromethyl-2-pyridyl or 5-trifluoromethyl-2-pyridyl. In certain instances, $R^{13}$ is preferably 2-methylbutyl, 2,2-dimethylpropyl, cyclopropylmethyl, cyclobutylmethyl, cyclopentylmethyl, cyclohexylmethyl, cyclopropyl, cyclobutyl, cyclopentyl, cyclohexyl, isobutyl or t-butyl.

In an eleventh group of embodiments, the compounds of Formula IX, or pharmaceutically acceptable salts, hydrates or solvates thereof, have a subformula (IXb-2):

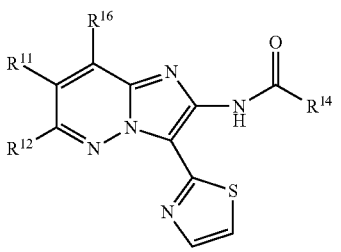

IXb-2 wherein substituents $R^{11}$, $R^{12}$, $R^{14}$ and $R^{16}$ are as defined above in Formula (IX). In certain instances, $R^{11}$ is —H. In other instances, $R^{11}$ and $R^{16}$ are —H.

In a twelfth group of embodiments, the compounds of Formula IX, or pharmaceutically acceptable salts, hydrates or solvates thereof, have a subformula (IXb-3):

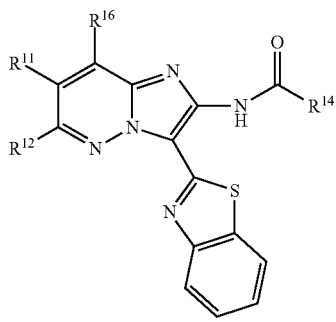

IXb-3 wherein substituents $R^{11}$, $R^{12}$, $R^{14}$ and $R^{16}$ are as defined above in Formula (IX). In certain instances, $R^{11}$ is —H. In other instances, $R^{11}$ and $R^{16}$ are —H.

In a thirteenth group of embodiments, the compounds of Formula IX, or pharmaceutically acceptable salts, hydrates or solvates thereof, have a subformula (IXb-4):

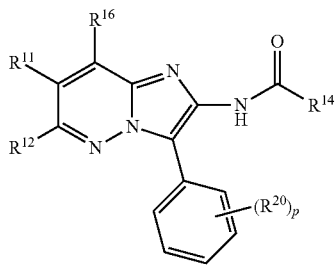

IXb-4 wherein substituents $R^{11}$, $R^{12}$, $R^{14}$ and $R^{16}$ are as defined above in Formula (IX). In certain instances, $R^{11}$ is —H. In other instances, $R^{11}$ and $R^{16}$ are —H. The subscript p is an integer of 0-3; and $R^{20}$ is independently selected from the group consisting of halogen, $C_{1-8}$haloalkoxy, $C_{1-8}$alkoxy, $C_{1-8}$haloalkyl, —CN and $R^b$. In certain instances, p is 1 or 2 and $R^{20}$ is independently selected from —F, —Cl, —CF$_3$, —OCF$_3$, —CN, or —CH$_3$.

In a fourteenth group of embodiments, the compounds of Formula IX, or pharmaceutically acceptable salts, hydrates or solvates thereof, have a subformula (IXb-5):

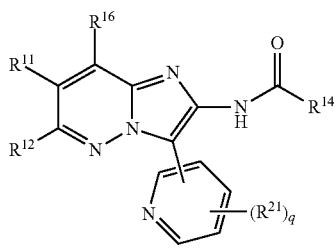

IXb-5 wherein substituents $R^{11}$, $R^{12}$, $R^{14}$ and $R^{16}$ are as defined above in Formula (IX). In certain instances, $R^{11}$ is —H. In other instances, $R^{11}$ and $R^{16}$ are —H. The subscript q is an integer of 0-3; and $R^{21}$ is independently selected from the group consisting of halogen, $C_{1-8}$haloalkoxy, $C_{1-8}$alkoxy, $C_{1-8}$haloalkyl, —CN and $R^b$. In certain instances, q is 1 or 2 and $R^{21}$ is independently selected from —F, —Cl, —CF$_3$, —OCF$_3$, —CN or —CH$_3$. In some instances, the pyridyl group is 2-pyridyl, 3-pyridyl or 4-pyridyl.

In certain instances of the above ninth to the fourteenth groups of embodiments, $R^{14}$ is selected from the group consisting of 3,4-difluorobenzyl, cyclobutyl, —CH(s-OH)-t-Bu, —CH$_2$-t-Bu, —CH$_2$CH(CF$_3$)CH$_3$, (R)—CH$_2$CH(CF$_3$)CH$_3$, (S)—CH$_2$CH(CF$_3$)CH$_3$, —CH$_2$CH(CF$_3$)CH$_3$, cyclohexylmethyl, —CH(CH$_3$)CH(CH$_3$)$_2$, 4-fluorobenzyl, 3-fluorobenzyl, cyclobutylmethyl, —CH$_2$CH$_2$-t-Bu, 4-fluorophenyl, 3,4-difluorophenyl, —CH(CH$_3$)-t-Bu, (R)-2-tetrahydrofuranyl, —CH$_2$CH(CH$_3$)CF$_3$, cyclopentyl, —CH$_2$CH$_2$CF$_3$, 3,3-difluorocyclopentylmethyl, 4,4-difluorocyclohexyl and 2,2-difluorocyclopropyl.

In the fifteenth group of embodiments, the compounds of Formula IX, or pharmaceutically acceptable salts, hydrates or solvates thereof, have a subformula (IXc):

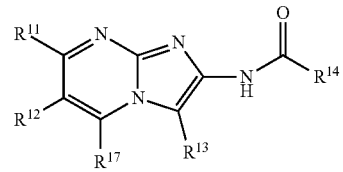

IXc wherein substituents $R^{11}$, $R^{12}$, $R^{13}$, $R^{14}$ and $R^{17}$ are as defined above in Formula (IX). In certain instances, $R^{11}$ and $R^{17}$ are —H. In certain instances, $R^{13}$ is preferably 2-methylbutyl, 2,2-dimethylpropyl, cyclopropylmethyl, cyclobutylmethyl, cyclopentylmethyl, cyclohexylmethyl, cyclopropyl, cyclobutyl, cyclopentyl, cyclohexyl, isobutyl or t-butyl.

In the sixteenth group of embodiments, the compounds of Formula IX, or pharmaceutically acceptable salts, hydrates or solvates thereof, have a subformula (IXc-1):

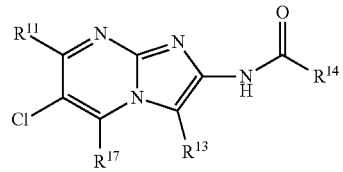

IXc-1 wherein substituents $R^{11}$, $R^{13}$, $R^{14}$ and $R^{17}$ are as defined above in Formula (IX). In certain instances, $R^{11}$ and $R^{17}$ are —H. In certain instances, $R^{13}$ is preferably 2-methylbutyl, 2,2-dimethylpropyl, cyclopropylmethyl, cyclobutylmethyl, cyclopentylmethyl, cyclohexylmethyl, cyclopropyl, cyclobutyl, cyclopentyl, cyclohexyl, isobutyl or t-butyl.

In a seventeenth group of embodiments, the compounds of Formula IX, or pharmaceutically acceptable salts, hydrates or solvates thereof, have a subformula (IXc-2):

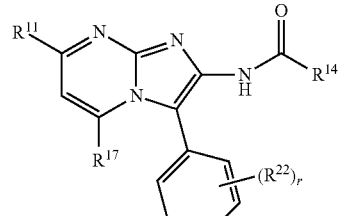

IXc-2 wherein the substituents $R^{11}$, $R^{13}$, $R^{14}$ and $R^{17}$ are as defined above in Formula (IX). The subscript r is an integer of 0-3;

and $R^{22}$ is selected from halogen, $C_{1-8}$haloalkoxy, $C_{1-8}$alkoxy, $C_{1-8}$haloalkyl, —CN or $R^b$. In certain instances, $R^{11}$ and $R^{17}$ are —H.

In an eighteenth group of embodiments, the compounds of Formula IX, or pharmaceutically acceptable salts, hydrates or solvates thereof, have a subformula (IXd-1):

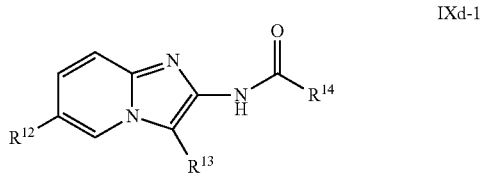

IXd-1 wherein the substituents $R^{12}$, $R^{13}$ and $R^{14}$ are as defined above in Formula (IX). In certain instances, $R^{12}$ is $C_{1-8}$haloalkyl or halogen. Preferably, $R^{12}$ is $CF_3$ or F. In some embodiments, $R^{13}$ is preferably $C_{3-8}$cycloalkyl, $C_{1-8}$alkyl, $C_{3-8}$cycloalkyl-$C_{1-6}$alkyl, or a heteroaryl optionally substituted with a $C_{1-4}$haloalkyl. More preferably, $R^{13}$ is cyclopropyl, cyclobutyl, cyclopentyl, cyclohexyl, 1-methylcyclopentyl, methylcyclopentylmethyl, cyclohexylmethyl, 4-trifluoromethyl-2-pyridyl, 2,2-dimethylpropyl or 3-methyl-1-butyl. In some embodiments, $R^{14}$ is $C_{1-8}$haloalkyl, aryl or $C_{3-8}$cycloalkyl-$C_{1-6}$alkyl, wherein the aromatic portion of the $R^{14}$ group is optionally substituted with from 1-2 halogens and the cycloalkyl portion of the $R^{14}$ is optionally substituted with a $C_{1-4}$alkyl. Preferably, $R^{14}$ is $CF_3(CH_3)_2CCH_2$—, $CF_3(CH_3)_2C$—, 3,4-difluorophenyl or 1-methylcyclopentylmethyl.

In a nineteenth group of embodiments, the compounds of Formula IX, or pharmaceutically acceptable salts, hydrates or solvates thereof, have a subformula (IXd-2):

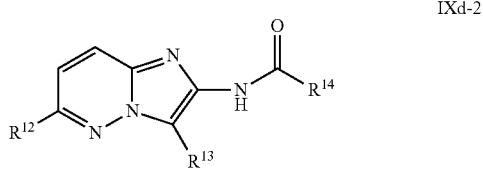

IXd-2 wherein the substituents $R^{13}$ and $R^{14}$ are as defined above in Formula (IX). In certain instances, $R^{12}$ is $C_{1-8}$haloalkyl or halogen. Preferably, $R^{12}$ is $CF_3$ or F. In some embodiments, $R^{13}$ is preferably $C_{3-8}$cycloalkyl, $C_{1-8}$alkyl, $C_{3-8}$cycloalkyl-$C_{1-6}$alkyl, or a heteroaryl optionally substituted with a $C_{1-4}$haloalkyl. More preferably, $R^{13}$ is cyclopropyl, cyclobutyl, cyclopentyl, cyclohexyl, 1-methylcyclopentyl, 1-methylcyclopentylmethyl, cyclohexylmethyl, 4-trifluoromethyl-2-pyridyl, 2,2-dimethylpropyl or 3-methyl-1-butyl. In some embodiments, $R^{14}$ is $C_{1-8}$haloalkyl, aryl or $C_{3-8}$cycloalkyl-$C_{1-6}$alkyl, wherein the aromatic portion of the $R^{14}$ group is optionally substituted with from 1-2 halogens and the cycloalkyl portion of the $R^{14}$ is optionally substituted with a $C_{1-4}$alkyl. Preferably, $R^{14}$ is $CF_3(CH_3)_2CCH_2$—, $CF_3(CH_3)_2C$—, 3,4-difluorophenyl or 1-methylcyclopentylmethyl.

In the above embodiments of the compounds having subformulas IXa, IXa-1, IXa-2, IXa-3, IXa-4, IXa-5, IXa-6, IXa-7, IXb-1, IXb-2, IXb-3, IXb-3, IXb-4, IXb-5, IXc, IXc-1, IXc-2, IXd-1 and IXd-2, at each occurrence, "alkyl" by itself or as part of another substituent, is an unsubstituted, fully saturated, straight or branched chain hydrocarbon radical unless otherwise specified; at each occurrence, "cycloalkyl" by itself or as part of another substituent is an unsubstituted, fully saturated, cyclic hydrocarbon radical unless specified otherwise; and at each occurrence, "aryl" by itself or as part of another substituent is a monovalent monocyclic, bicyclic or polycyclic polyunsaturated aromatic hydrocarbon radical. In some preferred embodiments, "aryl" by itself or as part of another substituent denotes a monovalent monocyclic, bicyclic or polycyclic polyunsaturated unsubstituted aromatic hydrocarbon radical unless otherwise specified and "heteroaryl" by itself or as part of another substituent denotes unsubstituted aryl groups (or rings) that contains from one to five heteroatoms selected from N, O, or S, wherein the nitrogen and sulfur atoms are optionally oxidized, and the nitrogen atom(s) are optionally quaternized unless otherwise specified.

In yet other aspects, also within the scope of the present invention are compounds of the invention that are poly- or multi-valent species, including, for example, species such as dimers, trimers, tetramers and higher homologs of the compounds of the invention or reactive analogues thereof. The poly- and multi-valent species can be assembled from a single species or more than one species of the invention. For example, a dimeric construct can be "homo-dimeric" or "heterodimeric." Moreover, poly- and multi-valent constructs in which a compound of the invention or a reactive analogue thereof, can be attached to an oligomeric or polymeric framework (e.g., polylysine, dextran, hydroxyethyl starch and the like) are within the scope of the present invention. The framework is preferably polyfunctional (i.e. having an array of reactive sites for attaching compounds of the invention). Moreover, the framework can be derivatized with a single species of the invention or more than one species of the invention.

In still other aspects, moreover, the present invention includes compounds within a motif described herein, which are functionalized to afford compounds having water-solubility that is enhanced relative to analogous compounds that are not similarly functionalized. Thus, in these other aspects, any of the substituents set forth herein can be replaced with analogous radicals that have enhanced water solubility. For example, it is within the scope of the invention to, for example, replace a hydroxyl group with a diol, or an amine with a quaternary amine, hydroxy amine or similar more water-soluble moiety. In a preferred embodiment, additional water solubility is imparted by substitution at a site not essential for the activity towards the ion channel of the compounds set forth herein with a moiety that enhances the water solubility of the parent compounds. Methods of enhancing the water-solubility of organic compounds are known in the art. Such methods include, but are not limited to, functionalizing an organic nucleus with a permanently charged moiety, e.g., quaternary ammonium, or a group that is charged at a physiologically relevant pH, e.g. carboxylic acid, amine. Other methods include, appending to the organic nucleus hydroxyl- or amine-containing groups, e.g. alcohols, polyols, polyethers, and the like. Representative examples include, but are not limited to, polylysine, polyethyleneimine, poly(ethyleneglycol) and poly(propyleneglycol). Suitable functionalization chemistries and strategies for these compounds are known in the art. See, for example, Dunn, R. L., et al., Eds. *Polymeric Drugs and Drug Delivery Systems*, ACS Symposium Series Vol. 469, American Chemical Society, Washington, D.C. 1991.

II. Preparation of the Compounds

Compounds of the present invention can be prepared using readily available starting materials or known intermediates. The synthetic schemes set forth below provide exemplary synthetic pathways for the preparation of compounds of the invention.

As shown in the Schemes and Examples below, there are a variety of synthetic routes by which a skilled artisan can prepare compounds and intermediates of the present invention. Other routes or modification of the routes presented below would be readily apparent to a skilled artisan and within the scope of the present invention. Schemes 1, 2 and 3 illustrate three general synthetic approaches for compounds as described herein, for example, compounds of Formulas I, II, III, IV, V, VI, VII, VIII, IX, IXa, IXa-1, IXa-2, IXa-3, IXa-4, IXa-5, IXa-6, IXa-7, IXb-1, IXb-2, IXb-3, IXb-3, IXb-4, IXb-5, IXc, IXc-1, IXc-2, IXd-1 and IXd-2 and compounds set forth in Examples 1-6 and Tables 1-6. These compounds can be prepared according the procedures set forth in reaction Schemes 1-3 and synthetic methods 1-6. In Schemes 1 and 2, L is a leaving group, such as —Cl, —Br, —I or tosylate; R' and R'' are non-interfering substituents; X is a halo group; and $R^{13}Q$ is an organoborane or an organozinc compound, wherein Q can be —B(OH)$_2$, —B(OR')$_2$, —ZnX or other suitable agents. Other substituents are as defined above in Formula (IX).

In Scheme 1, the starting material (aa) is either commercially available or can be readily prepared according the literature procedures. The fused imidazole ring in the key intermediate (ee) can be prepared by cyclization of intermediate (cc) in the presence of trifluoro acetic acid. Intermediate (cc) can be prepared by reacting compound (aa) with TsCl to form compound (bb), which is further reacted with a substituted amide, L-CH$_2$C(O)NH$_2$. The precursor compound (gg) can be prepared by either directly reacting with $R^{13}X$ in the presence of a palladium complex or converting to intermediates (ff) and (dd), which are further reacted with $R^{13}Q$/palladium complex and iodoalkane/BuLi, respectively. Subsequent hydrolysis of precursor compound (gg) produces compound (hh), which is further reacted with an acyl chloride, Cl—C(O)R$^{14}$ to yield compound (IX).

Alternatively, as shown in Scheme 2, the fused imidazole ring in key intermediate (ee') can be prepared by reacting compound (aa) with compound (jj) under a reflux condition. Subsequent transformations of intermediate (ee') to compound (nn) are similar to those described in Scheme 1. The formation of precursor compound (oo) is accomplished by

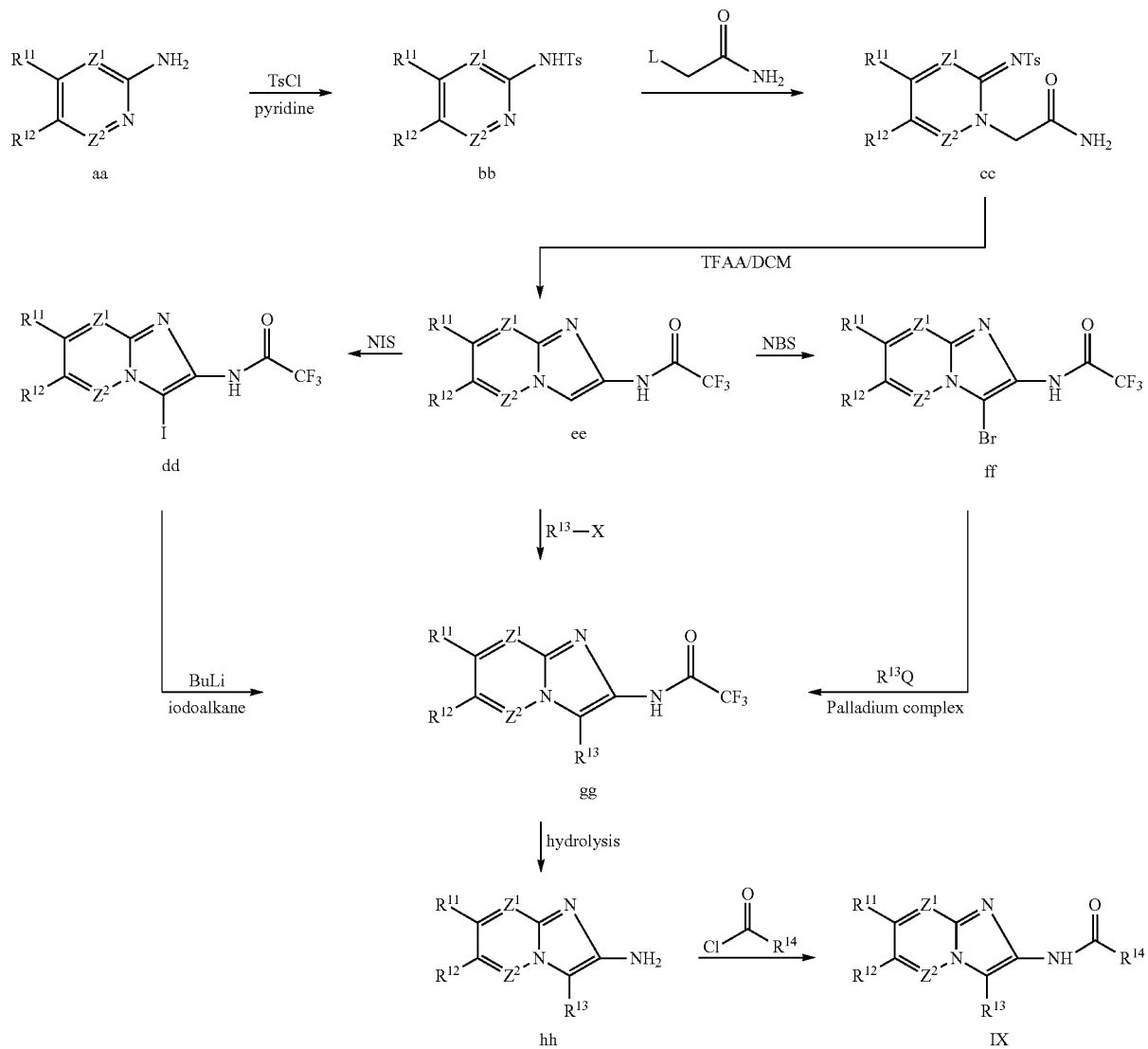

hydrolyzing compound (nn) and reacting with diphenylphosphonic azide. Subsequent hydrolysis of precursor compound (oo) yields compound (hh), which is reacted with ClC(O)R$^{14}$ to produce compound (IX).

445. The 4,4,4-trifluoro-3,3-dimethylbutanoic acid was prepared as shown in Example 7 and used to prepare compounds 431, 432, 433, 434, 436, 437, 438, 439, 440, 441, 442, 443 and 444.

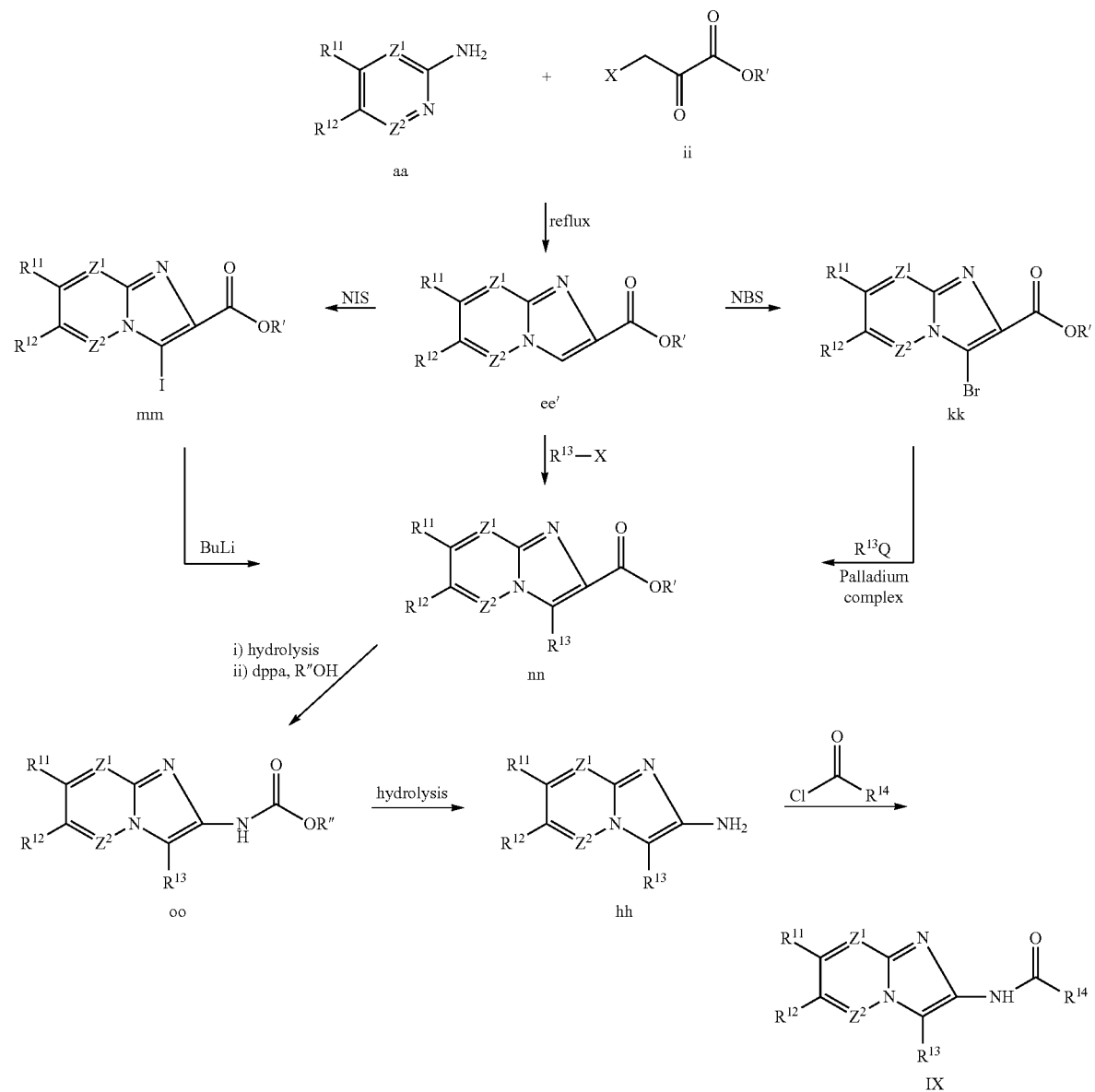

Scheme 3 outlines another synthetic route to the compounds of the present invention. The starting materials for the synthesis consist of commercially available pyridines ($Z^2$=C) and pyridazines ($Z^2$=N). Various derivatives at R$^{13}$ can be made by using commercially available alkyl zinc bromides (i.e. cycloproplyl zinc bromide, cyclobutyl zinc bromide, cyclopentyl zinc bromide). The changes at R$^{14}$ result from the use of different carboxylic acids to generate the acid chlorides. Examples of commercially available carboxylic acids are 3,3,3-trifluororo-2,2-dimethylpropionic acid, 1-(1,1,1-trifluoro-2-methylpropan-2-yl)cyclopropanecarboxylic acid, 3,4-diflorobenzoic acid. The 2-(1-methylcyclopentyl) acetic acid was prepared as described and used for compound

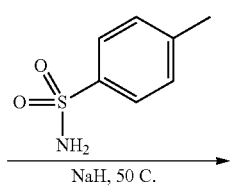

$Z^2$ = C or N
R$^{12}$ = F, CF3, Cl, CH3

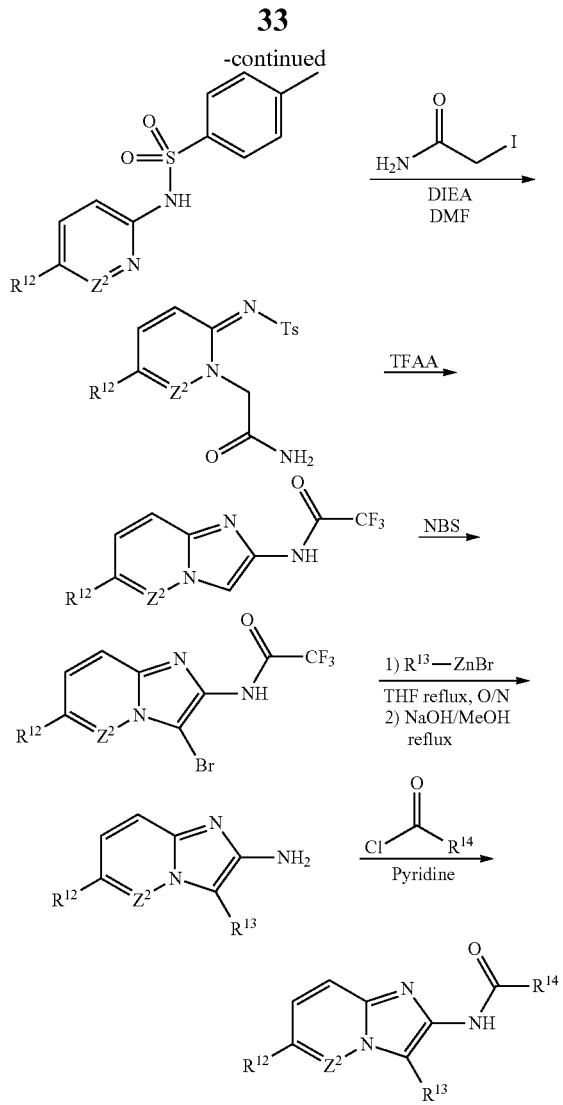

Accordingly, in a first set of embodiments, the present invention provides a compound of Formula (IX):

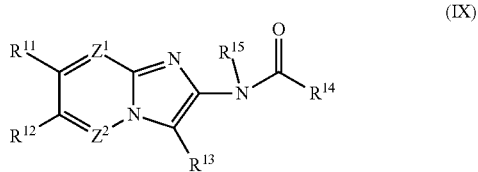

(IX)

or a pharmaceutically acceptable salt, hydrate or solvate thereof, $R^{11}$ and $R^{12}$ are each independently selected from the group consisting of —H, halogen, $C_{1-8}$haloalkyl, —CN, $C_{1-8}$alkyl, $C_{1-8}$alkoxy, aryloxy and aryl-$C_{1-8}$alkoxy;

$R^{13}$ is selected from the group consisting of —H, $C_{1-8}$alkyl, $C_{2-8}$alkenyl, aryl, $C_{3-8}$cycloalkyl, aryl-$C_{1-6}$alkyl, $C_{3-8}$cycloalkyl-$C_{1-8}$alkyl, heteroaryl and heteroaryl-$C_{1-6}$alkyl, wherein the aromatic portion of the $R^{13}$ group is optionally substituted with from 1-3 $R^a$ substituents, each $R^a$ is independently selected from the group consisting of halogen, $C_{1-8}$haloalkoxy, $C_{1-8}$alkoxy, $C_{1-8}$haloalkyl, —CN and $R^b$, wherein $R^b$ is $C_{1-8}$alkyl optionally substituted with from 1-2 substituents selected from halogen, —CN, —OH, $C_{1-8}$haloalkoxy or $C_{1-8}$alkoxy; or any two adjacent $R^a$ substituents together with the atoms to which they are attached form a 5- or 6-membered carbocyclic ring, optionally substituted with a $C_{1-8}$alkyl;

$R^{14}$ is selected from the group consisting of $C_{1-8}$alkyl, $C_{1-8}$haloalkyl, $C_{3-8}$cycloalkyl, $C_{3-8}$cycloalkyl-$C_{1-8}$alkyl, aryl, aryl-$C_{1-8}$alkyl, $C_{1-8}$alkoxy, aryl-$C_{1-8}$alkoxy, $C_{5-6}$heterocycloalkyl, $C_{5-6}$heterocycloalkyl-$C_{1-8}$alkyl, $R^c$, —NHR$^d$ and —N(R$^d$)$_2$, wherein $R^c$ is $C_{1-8}$alkyl substituted with from 1-2 members selected from —OH, CH$_2$N(R$^d$)$_2$, —OC(O)$C_{1-8}$alkyl, —OC(O)aryl, $C_{1-8}$alkoxy or aryloxy and R$^d$ is $C_{1-8}$alkyl or aryl-$C_{1-8}$alkyl, wherein the aromatic portion of the $R^{14}$ group is optionally substituted with from 1-3 $R^e$ substituents independently selected from the group consisting of halogen, $C_{1-8}$haloalkyl, $C_{1-8}$alkyl, $C_{1-8}$alkoxy, —CN or haloalkoxy, —OH, —OC(O)O—R$^f$, —OC(O)R$^f$, —OC(O)NHR$^f$, —OC(O)N(R$^f$)$_2$, —S(O)R$^f$, —S(O)$_2$R$^f$, —SO$_2$NH$_2$, —S(O)$_2$NHR$^f$, —S(O)$_2$N(R$^f$)$_2$, —NHS(O)$_2$R$^f$, —NR$^f$S(O)$_2$R$^f$, —C(O)NH$_2$, —C(O)NHR$^f$, —C(O)N(R$^f$)$_2$, —C(O)R$^f$, —C(O)H, wherein each R$^f$ is independently a $C_{1-8}$alkyl; and the cycloalkyl portion of the $R^{14}$ group is optionally substituted with from 1-3 substituents selected from halogen, $C_{1-8}$alkyl or optionally fused with a 5- or 6-membered aromatic ring having from 0-2 heteroatoms as ring members selected from N, O or S;

$R^{15}$ is —H or —C(O)$C_{1-8}$alkyl;

$Z^1$ is =N— or =C(R$^{16}$)— and $Z^2$ is =N— or =C(R$^{17}$)—, wherein $R^{16}$ and $R^{17}$ are each independently —H, $C_{1-8}$alkyl, halogen, —CN, $C_{1-8}$haloalkyl, $C_{1-8}$haloalkoxy, —OR$^g$ or —N(R$^g$)$_2$, wherein $R^g$ is independently —H, $C_{1-8}$alkyl or aryl-$C_{1-8}$alkyl, with the proviso that $Z^1$ and $Z^2$ are not simultaneously =N—;

at each occurrence, "alkyl" by itself or as part of another substituent, is an unsubstituted, fully saturated, straight or branched chain hydrocarbon radical unless specified otherwise; at each occurrence, "cycloalkyl" by itself or as part of another substituent is an unsubstituted, fully saturated, cyclic hydrocarbon radical unless specified otherwise; and at each occurrence, "aryl" by itself or as part of another substituent is a monovalent monocyclic, bicyclic or polycyclic polyunsaturated unsubstituted aromatic hydrocarbon radical. In some preferred embodiments, "aryl" by itself or as part of another substituent denotes a monovalent monocyclic, bicyclic or polycyclic polyunsaturated unsubstituted aromatic hydrocarbon radical unless otherwise specified and "heteroaryl" by itself or as part of another substituent denotes unsubstituted aryl groups (or rings) that contains from one to five heteroatoms selected from N, O, or S, wherein the nitrogen and sulfur atoms are optionally oxidized, and the nitrogen atom(s) are optionally quaternized unless otherwise specified In a second set of embodiments, the invention provides compounds of the first set, wherein $R^{15}$ is —H.

In a third set of embodiments, the invention provides compounds of the first set, wherein the compounds have Formula (IXa):

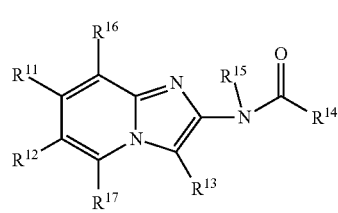

IXa wherein $R^{16}$ and $R^{17}$ are each independently —H, $C_{1-8}$alkyl, halogen, —CN, $C_{1-8}$haloalkyl, $C_{1-8}$haloalkoxy, —OR$^g$ or —N(R$^g$)$_2$, wherein $R^g$ is independently —H, $C_{1-8}$alkyl or aryl-$C_{1-8}$alkyl.

In a fourth set of embodiments, the invention provides compounds of the third set, wherein $R^{15}$ is —H.

In a fifth set of embodiments, the invention provides compounds of the first set or the third set, wherein the compounds have a formula selected from the group consisting of:

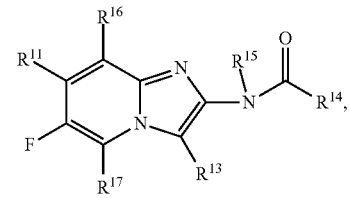
IXa-1

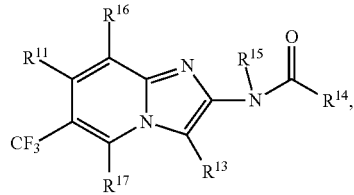
IXa-2

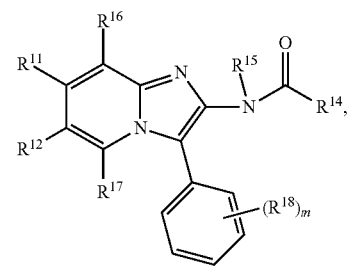
IXa-3

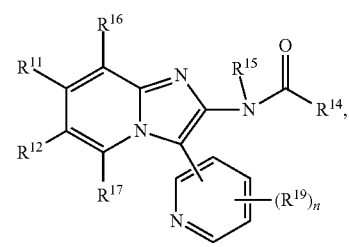
IXa-4

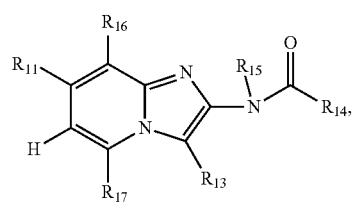
IXa-5

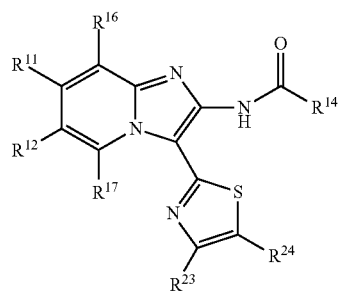
IXa-6
and

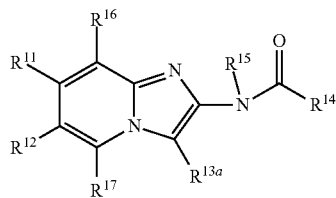
IXa-7 wherein $R^{16}$ and $R^{17}$ are each independently —H, $C_{1-8}$alkyl, halogen, CN, $C_{1-8}$haloalkyl, $C_{1-8}$haloalkoxy, —$OR^g$ or —$N(R^g)_2$, wherein $R^g$ is independently —H, $C_{1-8}$alkyl or aryl-$C_{1-8}$alkyl; the subscripts m and n are each independently an integer of 0-3; $R^{13a}$ is selected from the group consisting of cyclopropyl, cyclobutyl, cyclopentyl cyclohexyl and 2,2-dimethylpropyl; $R^{18}$ and $R^{19}$ are each independently selected from the group consisting of halogen, $C_{1-8}$haloalkoxy, $C_{1-8}$alkoxy, $C_{1-8}$haloalkyl, —CN and $R^b$; and $R^{23}$ and $R^{24}$ are each independently —H, $C_{1-8}$alkyl, halogen, $C_{1-8}$haloalkyl, —CN, —$NH_2$, —$NHC_{1-8}$alkyl, —$N(C_{1-8}$alkyl$)_2$ or $R^e$.

In a sixth set of embodiments, the invention provides compounds of the fifth set, wherein $R^{15}$ is —H.

In a seventh set of embodiments, the invention provides compounds of the first set, wherein the compounds have Formula (IXb):

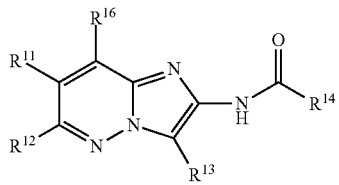
IXb

In an eighth set of embodiments, the invention provides compounds of the first set or the seventh set, wherein the compounds have a Formula selected from:

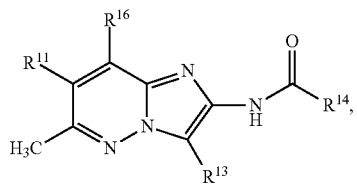
IXb-1

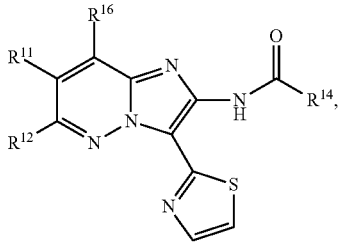
IXb-2

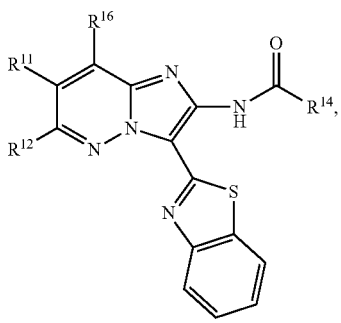
IXb-3

-continued

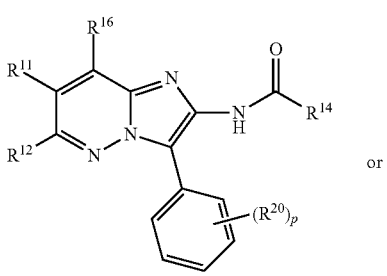
IXb-4

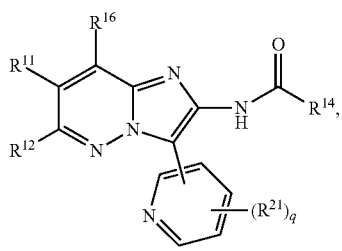
IXb-5 wherein the subscripts p and q are each independently an integer of 0-3; and $R^{20}$ and $R^{21}$ are each independently selected from the group consisting of halogen, $C_{1-8}$haloalkoxy, $C_{1-8}$alkoxy, $C_{1-8}$haloalkyl, —CN and $R^b$.

In a ninth set of embodiments, the invention provides compounds of the first set, wherein the compounds have Formula (IXc):

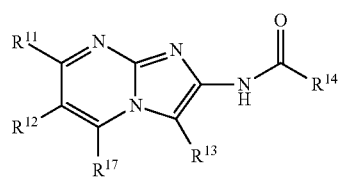
IXc

In a 10th set of embodiments, the invention provides compounds of the first set or the ninth set, wherein the subscript r is an integer of 0-3; and $R^{22}$ is selected from halogen, $C_{1-8}$haloalkoxy, $C_{1-8}$alkoxy, $C_{1-8}$haloalkyl, —CN or $R^b$.

In an 11th set of embodiments, the invention provides compounds of the first set, wherein the compounds have the Formula:

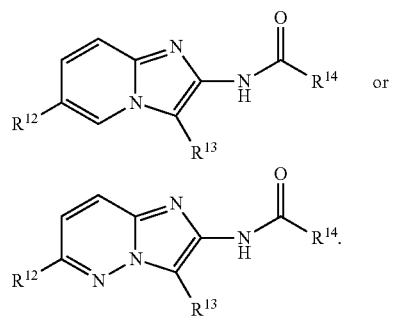

In a 12th set of embodiments, the invention provides compounds of any of sets 1-9 and 11, wherein $R^{12}$ is F or $CF_3$.

In a 13th set of embodiments, the invention provides compounds of any of sets 1-12, wherein $R^{13}$ is cyclopropyl, cyclobutyl, cyclopentyl, cyclohexyl, 1-methyl cyclopentyl, 1-methyl cyclopentylmethyl, cyclohexylmethyl, 4-trifluoromethyl-2-pyridyl, 2,2-dimethylpropyl or 3-methyl-1-butyl.

In a 14th set of embodiments, the invention provides compounds of any of sets 1-13, wherein $R^{14}$ is $CF_3(CH_3)_2CCH_2$—, $CF_3(CH_3)_2C$—, 3,4-difluorophenyl or 1-methylcyclopentylmethyl.

In an 15th set of embodiments, the invention provides compounds of any one of sets 1, 2, 3, 4, 5, 6, 7, 8, 9 and 10, wherein $R^{11}$ is —H, —$CH_3$, —$CF_3$, —CN, —$OCH_3$, —Cl, PhO—, Ph-$CH_2CH_2$O— or $PhCH_2$O—.

In a 16th set of embodiments, the invention provides compounds of any one of sets 1, 2, 3, 4, 5, 6, 7, 8, 9, and 15, wherein $R^{12}$ is —H, —F, —Cl, —Br, —CN, —$CH_3$, —$CF_3$, —$OCH_3$, PhO—, Ph-$CH_2CH_2$O— or $PhCH_2$O—.

In a 17th set of embodiments, the invention provides compounds of any one of sets 1, 2, 3, 4, 5, and 6, wherein $R^{11}$ is —H, —$CH_3$, —$CF_3$, —$OCH_3$, —Cl, PhO— or $PhCH_2$O— and $R^{12}$ is —H, —F, —Cl, —Br, —CN, —$CH_3$, —$CF_3$, PhO—, $PhCH_2$O— or —$OCH_3$.

In a 18th set of embodiments, the invention provides compounds of any of sets 1, 2, 3, 4, 5, 6, 7, 8, and 9, wherein $R^{11}$ is —H and $R^{12}$ is —Cl, —$CH_3$ or —$CF_3$.

In a 19th set of embodiments, the invention provides compounds of any of sets 1, 2, 3, 4, 5, 6, 7, 8, 15, 16, 17, and 18, wherein $R^{16}$ is selected from —H, $C_{1-8}$alkyl, $C_{1-8}$haloalkyl, $C_{1-8}$haloalkoxy, halogen, —OH, $C_{1-8}$alkoxy or aryl-$C_{1-6}$alkoxy.

In a 20th set of embodiments, the invention provides compounds of any of sets 1, 2, 3, 4, 5, 6, 9, 10, 15, 16, 17, 18, and 19 wherein $R^{17}$ is selected from —H, $C_{1-8}$alkyl, $C_{1-8}$haloalkyl, $C_{1-8}$haloalkoxy, halogen, —OH, $C_{1-8}$alkoxy or aryl-$C_{1-6}$alkoxy.

In a 21st set of embodiments, the invention provides compounds of any of sets 1, 2, 3, 4, 5, 6, 7, 8, 15, 16, 17, 18, 19 and 20, wherein $R^{16}$ is selected from —H, —F, —$CF_3$, —$OCF_3$, —$CH_3$, —$N(CH_3)(CH_2Ph)$, —OH, $C_{1-4}$alkoxy or benzyloxy.

In a 22nd set of embodiments, the invention provides compounds of any of sets 1, 2, 3, 4, 5, 6, 9, 10, 15, 16, 17, 18, 19, 20 and 21, wherein $R^{17}$ is selected from —H, —F, —$CF_3$, —$OCF_3$, —$CH_3$, —$N(CH_3)(CH_2Ph)$, —OH, $C_{1-4}$alkoxy or benzyloxy.

In a 23rd set of embodiments, the invention provides compounds of any of sets 1, 2, 3, 4, 5, 6, 7, 8, 9, 10, 15, 16, 17, 18, 19, 20, 21 and 22, wherein $R^{16}$ and $R^{17}$ are —H.

In a 24th set of embodiments, the invention provides compounds of any of sets 1-23, wherein $R^{13}$ is selected from the group consisting of —H, $C_{1-8}$alkyl, $C_{2-8}$alkenyl, aryl, $C_{3-8}$cycloalkyl, aryl-$C_{1-6}$alkyl, $C_{3-8}$cycloalkyl-$C_{1-8}$alkyl and 5- or 6-membered heteroaryl having from 1-3 heteroatoms as ring members selected from N, O or S, wherein the aryl or heteroaryl moiety of the $R^{13}$ group is optionally substituted with from 1-3 $R^a$ substituents, each $R^a$ is independently selected from the group consisting of halogen, —$OCF_3$, $C_{1-8}$alkoxy, —$CF_3$, —CN, hydroxy-$C_{1-8}$alkyl, $C_{1-8}$alkoxy-$C_{1-8}$alkyl, $C_{1-8}$haloalkyl, cyano-$C_{1-8}$alkyl, $C_{1-8}$haloalkoxy-$C_{1-8}$alkyl; or optionally any two adjacent $R^a$ substituents together with the atoms to which they are attached form a 5- or 6-membered carbocyclic ring, optionally substituted with a $C_{1-8}$alkyl.

In a 25th set of embodiments, the invention provides compounds of any of sets 1-24, wherein $R^{13}$ is selected from the group consisting of: i) —H, halogen, $C_{1-8}$alkyl, $C_{2-8}$alkenyl, $C_{3-8}$cycloalkyl, $C_{3-8}$cycloalkyl-$C_{1-8}$alkyl; ii) phenyl, benzyl, 2-pyridyl, 3-pyridyl, 4-pyridyl, 2-pyrizinyl, 3-pyridazinyl, 4-pyridazinyl, 2-pyrimidinyl or 1,3,5-triazin-2-yl, each of which is optionally substituted with from 1-3 substituents independently selected from —F, Br, Cl, I, —$CH_3$, $C_{1-8}$alkyl, isopropyl, —CF₃, —CN, —C(CH₃)₂CN, —OCF₃, C₁₋₈alkoxy or —CHF₂; and iii) 2-thiazolyl, 4-thiozoly, 5-thiazolyl, 2-benzothiazolyl, 3-pyrazolyl, 4-pyrazolyl, 5-pyrazolyl, each of which is optionally substituted with a C₁₋₈alkyl.

In a 26th set of embodiments, the invention provides compounds of any of sets 1-25, wherein R¹³ is selected from the group consisting of —H, Cl, Br, —I, —CH₃, vinyl, phenyl, 2-fluorophenyl, 3-fluorophenyl, 4-fluorophenyl, 2,4-difluorophenyl, 2,3-difluorophenyl, 2,5-difluorophenyl, 2,6-difluorophenyl, 2-trifluoromethylphenyl, 3-trifluoromethylphenyl, 4-trifluoromethylphenyl, 2-chlorophenyl, 3-chlorophenyl, 4-chlorophenyl, 2-trifluoromethylphenyl, 3-trifluoromethylphenyl, 4-trifluoromethylphenyl, 2-trifluoromethoxyphenyl, 3-trifluoromethoxyphenyl, 4-trifluoromethoxyphenyl, 2-pyridyl, 3-pyridyl, 4-pyridyl, cyclopropyl, 2,2-dimethylpropyl, 2-fluorobenzyl, 3-fluorobenzyl, 4-fluorobenzyl, 3-(2-cyanopropan-2-yl)phenyl, 4-(2-cyanopropan-2-yl)phenyl, 6-fluoro-3-pyridyl, 2-fluoro-3-pyridyl, 4-fluoro-3-pyridyl, 5-fluoro-3-pyridyl, 6-cyano-3-pyridyl, 2-cyano-3-pyridyl, 4-cyano-3-pyridyl, 5-cyano-3-pyridyl, 2-cyanophenyl, 3-cyanophenyl, 4-cyanophenyl, 6-fluoro-2-pyridyl, 3-fluoro-2-pyridyl, 4-fluoro-2-pyridyl, 5-fluoro-2-pyridyl, 6-trifluoromethyl-2-pyridyl, 3-trifluoromethyl-2-pyridyl, 4-trifluoromethyl-2-pyridyl, 5-trifluoromethyl-2-pyridyl, 3-difluoromethyl-4-fluorophenyl, 3-difluoromethyl-5-fluorophenyl, 3-fluoro-4-difluoromethylphenyl, 3-fluoro-4-trifluoromethoxyphenyl, 3-fluoro-5-trifluoromethoxyphenyl, 3-fluoro-4-cyanophenyl, 3-fluoro-5-cyanoyphenyl, 3-fluoro-4-trifluoromethylphenyl, 3-fluoro-5-trifluoromethylphenyl, 3-trifluoromethyl-4-fluorophenyl, 3-trifluoromethyl-4-methoxyphenyl, 3-trifluoromethyl-5-methoxyphenyl, 3-methoxy-4-trifluoromethylphenyl, 3-fluoro-4-methylphenyl, 3-fluoro-5-methylphenyl, 3-methyl-4-fluorophenyl, 4-trifluoromethyl-3-pyridyl, 5-trifluoromethyl-3-pyridyl, 6-trifluoromethyl-3-pyridyl, 5-methyl-2-pyridyl, 3-methyl-2-pyridyl, 4-methyl-2-pyridyl, 6-methyl-2-pyridyl, benzothiazol-2-yl, 3,4-difluorophenyl, 3-5-difluorophenyl, 2-pyrimidinyl, 3-methyl-4-fluorophenyl, 3-methyl-5-fluorophenyl, 3-fluoro-4-methylphenyl, 3,5-difluoro-4-methylphenyl, 3-methyl-4-chlorophenyl, 3-methyl-5-chlorophenyl, 3-chloro-4-methylphenyl, 3-chloro-2-pyridyl, 4-chloro-2-pyridyl, 5-chloro-2-pyridyl, 6-chloro-2-pyridyl, 3-methoxy-2-pyridyl, 4-methoxy-2-pyridyl, 5-methoxy-2-pyridyl, 6-methoxy-2-pyridyl, 1-isopropyl-4-pyrazolyl, cyclohexylmethyl, cyclohexyl, 3-methyl-1-butyl, cyclopentyl, 2-thiazolyl, 4-thiazolyl, 5-thiazolyl, 2-methyl-4-thiazolyl, 5-methyl-2-thiazolyl, 4-methyl-2-thiazolyl, cyclopropyl, cyclobutyl, cyclopentyl, cyclohexyl, cyclopropylmethyl, cyclobutylmethyl, cyclopentylmethyl and cyclohexylmethyl.

In a 27th set of embodiments, the invention provides compounds of any of sets 1-26, wherein R¹³ is 2-trifluoromethylphenyl, 3-trifluoromethylphenyl, 4-trifluoromethylphenyl, 2-trifluoromethoxyphenyl, 2-trifluoromethoxyphenyl, 2-trifluoromethoxyphenyl, 2,2-dimethylpropyl, cyclopropylmethyl, cyclopropyl, 2-thiazolyl, benzothiazol-2-yl, 6-trifluoromethyl-2-pyridyl, 3-trifluoromethyl-2-pyridyl, 4-trifluoromethyl-2-pyridyl or 5-trifluoromethyl-2-pyridyl.

In a 28th set of embodiments, the invention provides compounds of any of sets 1-27, wherein R¹³ is 2-trifluoromethylphenyl, 3-trifluoromethylphenyl, 4-trifluoromethylphenyl, 2-trifluoromethoxyphenyl, 3-trifluoromethoxyphenyl, 4-trifluoromethoxyphenyl, 2-chlorophenyl, 3-chlorophenyl or 4-chlorophenyl.

In a 29th set of embodiments, the invention provides compounds of any of sets 1-28, wherein R¹³ is C₁₋₈alkyl, C₃₋₈cycloalkyl, C₃₋₈cycloalkyl-C₁₋₄alkyl, or pyridyl substituted with trifluoromethyl.

In a 30th set of embodiments, the invention provides compounds of any of sets 1-29, wherein R¹³ is selected from the group consisting of 2-methylbutyl, 2,2-dimethylpropyl, cyclopropylmethyl, cyclobutylmethyl, cyclopentylmethyl, cyclohexylmethyl, isobutyl, 3-methylbutyl and 4-trifluoromethyl-2-pyridyl.

In a 31st set of embodiments, the invention provides compounds of any of sets 1-30, wherein R¹⁴ is selected from the group consisting of C₁₋₈alkyl, C₁₋₈haloalkyl, C₃₋₈cycloalkyl, C₃₋₈cycloalkyl-C₁₋₈alkyl, aryl-C₁₋₈alkyl, C₁₋₈alkoxy, aryl-C₁₋₈alkoxy, C₅₋₆heterocycloalkyl, C₅₋₆heterocycloalkyl-C₁₋₈alkyl, hydroxyl-C₁₋₈alkyl, C₁₋₈alkyl-C(O)O—C₁₋₈alkyl, aryl-C(O)O—C₁₋₈alkyl, C₁₋₈alkoxy-C₁₋₈alkyl or aryloxy-C₁₋₈alkyl, —NHR^d and —N(R^d)₂, wherein R^d is C₁₋₈alkyl or aryl-C₁₋₈alkyl; wherein the aromatic portion of the R¹⁴ group is optionally substituted with from 1-3 substituents selected from the group consisting of halogen, C₁₋₈haloalkyl, C₁₋₈alkyl, C₁₋₈alkoxy, —CN or haloalkoxy and the cycloalkyl portion of the R¹⁴ group is optionally substituted with from 1-3 substituents selected from halogen, C₁₋₈alkyl or optionally fused with a 5- or 6-membered aromatic ring having from 0-2 heteroatoms as ring members selected from N, O or S.

In a 32nd set of embodiments, the invention provides compounds of any of sets 1-31, R¹⁴ is selected from the group consisting of C₁₋₈alkyl, C₁₋₈haloalkyl, C₁₋₈alkoxy, C₅₋₆heterocycloalkyl, C₄₋₅heterocycloalkyl-C₁₋₈alkyl, hydroxyl-C₁₋₈alkyl, C₁₋₈alkyl-C(O)O—C₁₋₈ alkyl, C₁₋₈alkoxy-C₁₋₈ alkyl, —NH(C₁₋₈alkyl) and —N(C₁₋₈alkyl)₂, phenyl, phenyl-C₁₋₈alkyl, phenyl-C₁₋₈alkoxy, phenyl-C(O)O—C₁₋₈alkyl, phenoxy-C₁₋₈alkyl or (phenyl-C₁₋₈alkyl)NH—, C₃₋₈cycloalkyl and C₃₋₈cycloalkyl-C₁₋₈alkyl, wherein each phenyl moiety is optionally substituted with from 1-3 members independently selected from halogen, —CF₃, —CN, —C₁₋₈alkyl or —C₁₋₈alkoxy; and each cycloalkyl moiety is optionally substituted with 1-2 substituents selected from halogen and C₁₋₈alkyl or optionally fused with a phenyl ring.

In a 33th set of embodiments, the invention provides compounds of any of sets 1-32, wherein R¹⁴ is selected from the group consisting of —CH₃, —CF₃, 4-fluorophenyl, 3,4-difluorophenyl, benzyl, 2-fluorobenzyl, 3-fluorobenzyl, 4-fluorobenzyl, 2,2-dimethylpropyl, 2,2,2-trifluoroethyl, 3,3,3-trifluoropropyl, CF₃(CH₃)₂CCH₂—, CF₃(CH₃)₂C—, cyclopentylmethyl, Ph(CH₃)CH₂—, cyclopropylmethyl, cyclohexylmethyl, 2-methoxybenzyl, 3-methoxybenzyl, 4-methoxybenzyl, PhCH₂CH₂—, 2-trifluoromethylbenzyl, 3-trifluoromethylbenzyl, 4-trifluoromethylbenzyl, 2-cyanobenzyl, 3-cyanobenzyl, 4-cyanobenzyl, 3,4-difluorobenzyl, 3,5-difluorobenzyl, 3,6-difluorobenzyl, 2,6-difluorobenzyl, 2,4,4-trimethylpentyl, 2-fluoro-6-chloro-benzyl, 2-fluoro-3-chloro-benzyl, 2-fluoro-4-chloro-benzyl, 2-fluoro-5-chloro-benzyl, 3-fluoro-4-chlorobenzyl, 3-fluoro-5-chlorobenzyl, 3-fluoro-6-chlorobenzyl, 3,4-dichlorobenzyl, 3,5-dichlorobenzyl, 3,6-dichlorobenzyl, 2,6-dichlorobenzyl, 2-methylbenzyl, 3-methylbenzyl, 4-methylbenzyl, 2-chlorobenzyl, 3-chlorobenzyl, 4-chlorobenzyl, 2-methyl-3,3,3-trifluoropropyl, benzyloxy, 2-methylbutyl, CN—CH₂CH₂CH₂—, (CH₃)₂CHCH(CH₃)—, dimethylbutyl, cyclopropylethyl, 4,4,4-trifluorobutyl, (bicyclo[2.2.1]heptan-2-yl)methyl, (1-methylcyclohexyl)methyl, (1-methylcyclopentyl)methyl, (CH₃)₃CCH(OH)—, cyclobutylmethyl, CH₃C(O)OCH₂C(CH₃)₂CH₂—, (OH)CH₂C(CH₃)₂CH₂—, 1,1-difluoro-2,2-dimethylpropyl, t-butoxymethyl, t-butoxyethyl, 2-(4-fluorophenyl)ethylamino, 4-fluorobenzylamino, t-butylamino, 2-cyano-2-methylpropyl, cyclopentylethyl, Ph-O—CH(CH$_3$)—, 4-phenoxybenzyl, PhCH$_2$OCH$_2$—, 2-tetrahydropyranyl, 3,4-dichlorophenoxymethyl, 3,5-dichlorophenoxymethyl, 3,6-dichlorophenoxymethyl, 2,3-dichlorophenoxymethyl, 2,4-dichlorophenoxymethyl, 2,5-dichlorophenoxymethyl, 2,6-dichlorophenoxymethyl, 2-fluorophenoxyethyl, 3-fluorophenoxyethyl, 4-fluorophenoxyethyl, (tetrahydropyran-4-yl)methyl, 3,3-dimethylbutyl, 2-trifluoromethoxybenzyl, 3-trifluoromethoxybenzyl, 4-trifluoromethoxybenzyl, cyclopropyl, cyclobutyl, cyclopentyl, cyclohexyl, cyclooctyl, cycloheptyl, 2-indanyl, 1-indanyl, isobutyl, 3,3-difluorocyclopentylmethyl, 4,4-difluorocyclohexyl, 2,2-difluorocyclopropyl, (R)—CF$_3$CH(CH$_3$)CH$_2$—, (S)—CF$_3$CH(CH$_3$)CH$_2$—, CH$_3$C(O)OCH(t-butyl)-, HOCH(t-butyl)-, 2-tetrahydrofuranyl,

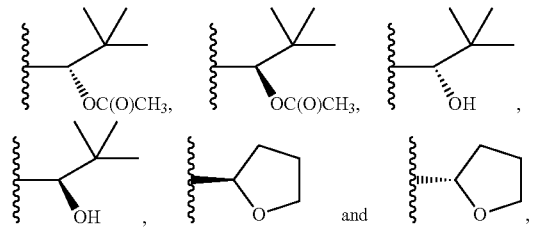

wherein the wavy line indicates the point of attachment to the rest of the molecule.

In a 34th set of embodiments, the invention provides compounds of any of sets 1-33, wherein R$^{14}$ is selected from the group consisting of 3,4-difluorobenzyl, cyclobutyl, —CH(s-OH)-t-Bu, —CH$_2$-t-Bu, —CH$_2$CH(CF$_3$)CH$_3$, (R)—CH$_2$CH(CF$_3$)CH$_3$, (S)—CH$_2$CH(CF$_3$)CH$_3$, —CH$_2$CH(CF$_3$)CH$_3$, cyclohexylmethyl, —CH(CH$_3$)CH(CH$_3$)$_2$, 4-fluorobenzyl, 3-fluorobenzyl, cyclobutylmethyl, —CH$_2$CH$_2$-t-Bu, 4-fluorophenyl, 3,4-difluorophenyl, —CH(CH$_3$)-t-Bu, (R)-2-tetrahydrofuranyl, —CH$_2$CH(CH$_3$)CF$_3$, CF$_3$(CH$_3$)$_2$CCH$_2$—, CF$_3$(CH$_3$)$_2$C—, 1-methylcyclopentylmethyl, cyclopentyl, —CH$_2$CH$_2$CF$_3$, 3,3-difluorocyclopentylmethyl, 4,4-difluorocyclohexyl and 2,2-difluorocyclopropyl.

In a 35th set of embodiments, the invention provides compounds of any of sets 1-34, wherein R$^{11}$, R$^{16}$ and R$^{17}$ are —H.

In a 36th set of embodiments, the invention provides compounds of any of sets 1-35, wherein R$^{11}$ and R$^{16}$ are —H.

In a 37th set of embodiments, the invention provides compounds of any of sets 1-36, wherein R$^{11}$ and R$^{17}$ are —H.

In another aspect, the invention provides a pharmaceutical composition including/comprising: a compound of any one of the above sets (i.e., sets 1 to 33) and a pharmaceutically acceptable excipient.

In the sets 1-33 embodiments above, at each occurrence, "alkyl" by itself or as part of another substituent, is an unsubstituted, fully saturated, straight or branched chain hydrocarbon radical unless specified otherwise; at each occurrence, "cycloalkyl" by itself or as part of another substituent is an unsubstituted, fully saturated, cyclic hydrocarbon radical unless specified otherwise; and at each occurrence, "aryl" by itself or as part of another substituent is a monovalent monocyclic, bicyclic or polycyclic polyunsaturated aromatic hydrocarbon radical. In some preferred embodiments, "aryl" by itself or as part of another substituent denotes a monovalent monocyclic, bicyclic or polycyclic polyunsaturated unsubstituted aromatic hydrocarbon radical unless otherwise specified and "heteroaryl" by itself or as part of another substituent denotes unsubstituted aryl groups (or rings) that contains from one to five heteroatoms selected from N, O, or S, wherein the nitrogen and sulfur atoms are optionally oxidized, and the nitrogen atom(s) are optionally quaternized unless otherwise specified.

In another aspect, the invention provides a method of modulating activity of a potassium ion channel in a subject, said method comprising/including: administering to said subject in need thereof an effective amount of a compound of any of sets 1-33 to modulate the activity of a potassium channel.

In a further aspect, the invention provides a method of increasing ion flow through voltage dependent potassium channels in a cell, said method comprising/including: contacting the cell with a compound of any of sets 1-33 in an amount sufficient to modulate the potassium ion channels.

In another aspect, the present invention provides a method of treating, preventing, inhibiting or ameliorating a central or peripheral nervous system disorder or condition through modulation of a potassium ion channel, said method comprising/including: administering to a subject in need of such treatment an effective amount of a compound of any of sets 1-33. In some embodiments, the disorder or condition is selected from the group consisting of migraine, ataxia, Parkinson's disease, bipolar disorders, trigeminal neuralgia, spasticity, mood disorders, brain tumors, psychotic disorders, myokymia, seizures, epilepsy, stroke, hearing and vision loss, Alzheimer's disease, age-related memory loss, learning deficiencies, anxiety, motor neuron diseases and urinary incontinence In yet another aspect, the present invention provides a method of treating a member selected from epilepsy, retinal degeneration, pain, anxiety, neuronal degeneration and bipolar disorder through modulation of a voltage-dependent potassium channel, said method comprising administering to a subject in need of such treatment, an effective amount of a compound of any of sets 1-33. In some embodiments, the condition or disorder is selected from epilepsy, seizure, retinal degeneration, pain, anxiety, neuronal degeneration, hearing loss and bipolar disorder. In certain instances, the pain is a member selected from neuropathic pain, diabetic pain, somatic pain, cutaneous pain, visceral pain, inflammatory pain, cancer pain, migraine pain, or musculoskeletal pain. In one instance, the condition or disorder is epilepsy or seizures. In another instance, the condition or disorder is hearing loss. In yet other instance, the condition or disorder is pain or anxiety. In still other instance, condition or disorder is neuronal degeneration. In another instance, the condition or disorder is retinal degeneration.

III. Assays for Modulators of KCNQ Channels

Assays for determining the ability of a compound of the invention to open a potassium ion channel are generally known in the art. One of skill in the art is able to determine an appropriate assay for investigating the activity of a selected compound of the invention towards a particular ion channel. For simplicity, portions of the following discussion focuses on KCNQ2 as a representative example, however, the discussion is equally applicable to other potassium ion channels.

KCNQ monomers as well as KCNQ alleles and polymorphic variants are subunits of potassium channels. The activity of a potassium channel comprising KCNQ subunits can be assessed using a variety of in vitro and in vivo assays, e.g., measuring current, measuring membrane potential, measuring ion flux, e.g., potassium or rubidium, measuring potassium concentration, measuring second messengers and transcription levels, using potassium-dependent yeast growth assays, and using e.g., voltage-sensitive dyes, radioactive tracers, and patch-clamp electrophysiology.

Furthermore, such assays can be used to test for activators of channels comprising KCNQ. As discussed elsewhere herein, activators (openers) of a potassium channel are useful for treating various disorders attributable to potassium channels. Such modulators are also useful for investigation of the channel diversity provided by KCNQ and the regulation/modulation of potassium channel activity provided by KCNQ.

Putative modulators of the potassium channels of the present invention, such as compounds of any of Formulas I, II, III, IV, V, VI, VII, VIII, IX, IXa, IXa-1, IXa-2, IXa-3, IXa-4, IXa-5, IXa-6, IXa-7, IXb-1, IXb-2, IXb-3, IXb-3, IXb-4, IXb-5, IXc, IXc-1, IXc-2, IXd-1 and IXd-2 or a compound of any of sets 1-33 are tested using biologically active KCNQ, either recombinant or naturally occurring, or by using native cells, like cells from the nervous system expressing the M-current. KCNQ can be isolated, co-expressed or expressed in a cell, or expressed in a membrane derived from a cell. In such assays, KCNQ2 is expressed alone to form a homomeric potassium channel or is co-expressed with a second subunit (e.g., another KCNQ family member, preferably KCNQ3) so as to form a heteromeric potassium channel. Modulation is tested using one of the in vitro or in vivo assays described above. Samples or assays that are treated with a potential potassium channel activator are compared to control samples without the test compound, to examine the extent of modulation. Control samples (untreated with activators) are assigned a relative potassium channel activity value of 100. Activation of channels comprising KCNQ2 is achieved when the potassium channel activity value relative to the control is 110%, more preferably 130%, more preferably 170% higher. Compounds that increase the flux of ions will cause a detectable increase in the ion current density by increasing the probability of a channel comprising KCNQ2 being open, by decreasing the probability of it being closed, by increasing conductance through the channel, and/or increasing the number or expression of channels.

The activity of the compounds of the invention can also be represented by EC50. In some embodiments, the compounds of the invention have an EC50 in a potassium ion channel assay of from about 5 nM to about 10 µM. In other embodiments, the compounds have an EC50 from about 5 nM to about 3 µM. In yet other embodiments, the compounds have an EC50 from about 5 nM to about 0.5 µM.

Changes in ion flux may be assessed by determining changes in polarization (i.e., electrical potential) of the cell or membrane expressing the potassium channel comprising, for example, KCNQ2, KCNQ2/3 or the M-current. A preferred means to determine changes in cellular polarization is by measuring changes in current or voltage with the voltage-clamp and patch-clamp techniques, using the "cell-attached" mode, the "inside-out" mode, the "outside-out" mode, the "perforated cell" mode, the "one or two electrode" mode, or the "whole cell" mode (see, e.g., Ackerman et al., *New Engl. J. Med.* 336:1575-1595 (1997)). Whole cell currents are conveniently determined using the standard methodology (see, e.g., Hamil et al., *Pflugers. Archiv.* 391:85 (1981). Other known assays include: radiolabeled rubidium flux assays and fluorescence assays using voltage-sensitive dyes (see, e.g., Vestergarrd-Bogind et al., *J. Membrane Biol.* 88:67-75 (1988); Daniel et al., *J. Pharmacol. Meth.* 25:185-193 (1991); Holevinsky et al., *J. Membrane Biology* 137:59-70 (1994)). Assays for compounds capable of increasing potassium flux through M-current channels found in native cells or through the channel proteins comprising KCNQ2 or heteromultimers of KCNQ subunits can be performed by application of the compounds to a bath solution in contact with and comprising cells having a channel of interest (see, e.g., Blatz et al., *Nature* 323:718-720 (1986); Park, *J. Physiol.* 481:555-570 (1994)). Generally, the compounds to be tested are present in the range from 1 pM to 100 mM.

The effects of the test compounds upon the function of the channels can be measured by changes in the electrical currents or ionic flux or by the consequences of changes in currents and flux. Changes in electrical current or ionic flux are measured by either increases or decreases in flux of ions such as potassium or rubidium ions. The cations can be measured in a variety of standard ways. They can be measured directly by concentration changes of the ions or indirectly by membrane potential or by radio-labeling of the ions. Consequences of the test compound on ion flux can be quite varied. Accordingly, any suitable physiological change can be used to assess the influence of a test compound on the channels of this invention. The effects of a test compound can be measured by a toxin binding assay. When the functional consequences are determined using intact cells or animals, one can also measure a variety of effects such as transmitter release (e.g., dopamine), hormone release (e.g., insulin), transcriptional changes to both known and uncharacterized genetic markers (e.g., northern blots), cell volume changes (e.g., in red blood cells), immunoresponses (e.g., T cell activation), changes in cell metabolism such as cell growth or pH changes, and changes in intracellular second messengers such as $Ca^{2+}$, or cyclic nucleotides.

KCNQ2 orthologs will generally confer substantially similar properties on a channel comprising such KCNQ2, as described above. In a preferred embodiment, the cell placed in contact with a compound that is suspected to be a KCNQ2 homolog is assayed for increasing or decreasing ion flux in a eukaryotic cell, e.g., an oocyte of *Xenopus* (e.g., *Xenopus laevis*) or a mammalian cell such as a CHO or HeLa cell. Channels that are affected by compounds in ways similar to KCNQ2 are considered homologs or orthologs of KCNQ2.

Utilizing screening assays such as described above, compounds of the invention were tested for their ability to open voltage-gated potassium channels. The results of these assays are set forth in Tables 1-5 in which the data are presented in terms of relative potency of the compounds tested to one another. The compound numbers in Tables 1-5 are cross-referenced to the compounds displayed in Examples 1-5.

IV. Pharmaceutical Compositions of Potassium Channel Modulators

In another aspect, the present invention provides pharmaceutical compositions comprising/including a pharmaceutically acceptable excipient and a compound described herein. In a group of exemplary embodiments, the compounds have any of Formulas I, II, III, IV, V, VI, VII, VIII, IX, IXa, IXa-1, IXa-2, IXa-3, IXa-4, IXa-5, IXa-6, IXa-7, IXb-1, IXb-2, IXb-3, IXb-3, IXb-4, IXb-5, IXc, IXc-1, IXc-2, IXd-1 and IXd-2. In another embodiment, the present invention provides a pharmaceutical composition comprising/including a compound set forth in Examples 1-5 and Tables 1-5.

IVa. Formulation of the Compounds (Compositions)

The compounds of the present invention can be prepared and administered in a wide variety of oral, parenteral and topical dosage forms. Thus, the compounds of the present invention can be administered by injection, that is, intravenously, intramuscularly, intracutaneously, subcutaneously, intraduodenally, or intraperitoneally. Also, the compounds described herein can be administered by inhalation, for example, intranasally. Additionally, the compounds of the present invention can be administered transdermally. Accordingly, the present invention also provides pharmaceutical compositions comprising a pharmaceutically acceptable carrier or excipient and a compound described herein, or a pharmaceutically acceptable salt thereof. The present invention also provides pharmaceutical compositions comprising a pharmaceutically acceptable carrier or excipient and a compound of Formulae I, II, III, IV, V, VI, VII, VIII, IX, IXa, IXa-1, IXa-2, IXa-3, IXa-4, IXa-5, IXa-6, IXa-7, IXb-1, IXb-2, IXb-3, IXb-3, IXb-4, IXb-5, IXc, IXc-1, IXc-2, IXd-1 and IXd-2 or a pharmaceutically acceptable salt thereof.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances, which may also act as diluents, flavoring agents, binders, preservatives, tablet disintegrating agents, or an encapsulating material.

In powders, the carrier is a finely divided solid, which is in a mixture with the finely divided active component. In tablets, the active component is mixed with the carrier having the necessary binding properties in suitable proportions and compacted in the shape and size desired.

The powders and tablets preferably contain from 5% or 10% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations, which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 10000 mg, more typically 1.0 mg to 1000 mg, most typically 10 mg to 500 mg, according to the particular application and the potency of the active component. The composition can, if desired, also contain other compatible therapeutic agents.

IVb. Effective Dosages

Pharmaceutical compositions provided by the present invention include compositions wherein the active ingredient is contained in a therapeutically effective amount, i.e., in an amount effective to achieve its intended purpose. The actual amount effective for a particular application will depend, inter alia, on the condition being treated. For example, when administered in methods to treat pain or anxiety, such compositions will contain an amount of active ingredient effective to achieve a clinically relevant degree of reduction in the condition being treated. Similarly, when the pharmaceutical composition is used to treat or prevent a central or peripheral nervous system disorder, e.g., Parkinson's disease a therapeutically effective amount will reduce one or more symptoms characteristic of the diseases (e.g., tremors) to below a predetermined pressure threshold. Determination of a therapeutically effective amount of a compound of the invention is well within the capabilities of those skilled in the art, especially in light of the detailed disclosure herein.

For any compound described herein, the therapeutically effective amount can be initially determined from cell culture assays. Target plasma concentrations will be those concentrations of active compound(s) that are capable of modulating, e.g., activating or opening the KCNQ channel. In preferred embodiments, the KCNQ channel activity is altered by at least 30%. Target plasma concentrations of active compound(s) that are capable of inducing at least about 50%, 70%, or even 90% or higher alteration of the KCNQ channel potassium flux are presently preferred. The percentage of alteration of the KCNQ channel in the patient can be monitored to assess the appropriateness of the plasma drug concentration achieved, and the dosage can be adjusted upwards or downwards to achieve the desired percentage of alteration.

As is well known in the art, therapeutically effective amounts for use in humans can also be determined from animal models. For example, a dose for humans can be formulated to achieve a circulating concentration that has been found to be effective in animals. A particularly useful animal model for predicting anticonvulsant dosages is the maximal electroshock assay (Fischer R S, *Brain Res. Rev.* 14: 245-278 (1989)). The dosage in humans can be adjusted by monitoring KCNQ channel activation and adjusting the dosage upwards or downwards, as described above.

A therapeutically effective dose can also be determined from human data for compounds which are known to exhibit similar pharmacological activities, such as retigabine (Rudnfeldt et al., *Neuroscience Lett.* 282: 73-76 (2000)).

Adjusting the dose to achieve maximal efficacy in humans based on the methods described above and other methods as are well-known in the art is well within the capabilities of the ordinarily skilled artisan.

By way of example, when a compound of the invention is used in the prophylaxis and/or treatment of an exemplary disease such as epilepsy, a circulating concentration of administered compound of about 0.001 µM to 20 µM is considered to be effective, with about 0.01 µM to 5 µM being preferred.

Patient doses for oral administration of the compounds described herein, which is the preferred mode of administration for prophylaxis and for treatment of an exemplary disease such as epilepsy, typically range from about 1 mg/day to about 10,000 mg/day, more typically from about 10 mg/day to about 1,000 mg/day, and most typically from about 1 mg/day to about 500 mg/day. Stated in terms of patient body weight, typical dosages range from about 0.01 to about 150 mg/kg/day, more typically from about 0.1 to about 15 mg/kg/day, and most typically from about 0.5 to about 10 mg/kg/day.

For other modes of administration, dosage amount and interval can be adjusted individually to provide plasma levels of the administered compound effective for the particular clinical indication being treated. For example, if acute epileptic seizures are the most dominant clinical manifestation, in one embodiment, a compound according to the invention can be administered in relatively high concentrations multiple times per day. Alternatively, if the patient exhibits only periodic epileptic seizures on an infrequent, periodic or irregular basis, in one embodiment, it may be more desirable to administer a compound of the invention at minimal effective concentrations and to use a less frequent administration regimen. This will provide a therapeutic regimen that is commensurate with the severity of the individual's disease.

Utilizing the teachings provided herein, an effective prophylactic or therapeutic treatment regimen can be planned which does not cause substantial toxicity and yet is entirely effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

V. Methods for Increasing Ion Flow in Voltage-Dependent Potassium Channels

In yet another aspect, the present invention provides methods for increasing ion flow through voltage dependent potassium channels in a cell. The method includes contacting a cell containing the target ion channels with an amount of a compound of the invention as described herein, sufficient to enhance the activity of a potassium channel. In one embodiment, the method includes contacting a cell containing the target ion channels with a potassium channel modulating amount of a compound of any of Formulas I, II, III, IV, V, VI, VII, VIII, IX, IXa, IXa-1, IXa-2, IXa-3, IXa-4, IXa-5, IXa-6, IXa-7, IXb-1, IXb-2, IXb-3, IXb-3, IXb-4, IXb-5, IXc, IXc-1, IXc-2, IXd-1 and IXd-2. For instances, the compound is present in an amount sufficient to enhance activities of a potassium ion channel.

The methods provided in this aspect of the invention are useful for the diagnosis of conditions that can be treated by modulating ion flux through voltage-dependent potassium channels, or for determining if a patient will be responsive to therapeutic agents, which act by opening potassium channels. In particular, a patient's cell sample can be obtained and contacted with a compound of the invention and the ion flux can be measured relative to a cell's ion flux in the absence of a compound of the invention, for example, a compound of any of Formulas I, II, III, IV, V, VI, VII, VIII, IX, IXa, IXa-1, IXa-2, IXa-3, IXa-4, IXa-5, IXa-6, IXa-7, IXb-1, IXb-2, IXb-3, IXb-3, IXb-4, IXb-5, IXc, IXc-1, IXc-2, IXd-1 and IXd-2 or a compound of any of sets 1-33. An increase in ion flux will typically indicate that the patient will be responsive to a therapeutic regimen of ion channel openers.

VI. Methods for Treating Conditions Mediated by Voltage-Dependent Potassium Channels The compounds of any of sets 1-33 described above or the compounds of Formulas I, II, III, IV, V, VI, VII, VIII, IX, IXa, IXa-1, IXa-2, IXa-3, IXa-4, IXa-5, IXa-6, IXa-7, IXb-1, IXb-2, IXb-3, IXb-3, IXb-4, IXb-5, IXc, IXc-1, IXc-2, IXd-1 or IXd-2 or pharmaceutically acceptable salts, hydrates or solvates thereof, which, inter alia, are useful in the treatment of a range of conditions, disorders and diseases through the modulation of potassium ion flux through voltage-dependent potassium channels. More particularly, the invention provides compounds, compositions and methods that are useful in the treatment of central or peripheral nervous system disorders (e.g., migraine, ataxia, Parkinson's disease, bipolar disorders, trigeminal neuralgia, spasticity, mood disorders, brain tumors, psychotic disorders, myokymia, seizures, epilepsy, hearing and vision loss, Alzheimer's disease, age-related memory loss, learning deficiencies, anxiety and motor neuron diseases), and as neuroprotective agents (e.g., to prevent stroke and the like). Compounds of the invention have use as agents for treating convulsive states, for example that following grand mal, petit mal, psychomotor epilepsy or focal seizure. The compounds of the invention are also useful in treating disease states such as gastroesophogeal reflux disorder and gastrointestinal hypomotility disorders.

The compounds of the invention are also useful in the treatment, prevention, inhibition and amelioration of urge urinary incontinence also known as bladder instability, neurogenic bladder, voiding dysfunction, hyperactive bladder or detrusor overactivity. The methods of this invention also include the prevention and treatment of mixed stress and urge urinary incontinence, including that associated with secondary conditions such as prostate hypertrophy. The methods of this invention are useful for inducing, assisting or maintaining desirable bladder control in a mammal experiencing or susceptible to bladder instability or urinary incontinence. These methods include prevention, treatment or inhibition of bladder-related urinary conditions and bladder instability, including idiopathic bladder instability, nocturnal enuresis, nocturia, voiding dysfunction and urinary incontinence. Also treatable or preventable with the methods of this invention is bladder instability secondary to prostate hypertrophy. The compounds described herein are also useful in promoting the temporary delay of urination whenever desirable. The compounds of this invention may also be utilized to stabilize the bladder and treat or prevent incontinence which urge urinary incontinence, stress urinary incontinence or a combination of urge and stress incontinence in a mammal, which may also be referred to as mixed urge and stress incontinence. These methods include assistance in preventing or treating urinary incontinence associated with secondary conditions such as prostate hypertrophy. These methods may be utilized to allow a recipient to control the urgency and frequency of urination. The methods of this invention include the treatment, prevention, inhibition and amelioration of urge urinary incontinence also known as bladder instability, neurogenic bladder, voiding dysfunction, hyperactive bladder, detrusor overactivity, detrusor hyper-reflexia or uninhibited bladder.

As described above, methods of this invention include treatments, prevention, inhibition or amelioration of hyperactive or unstable bladder, neurogenic bladder, sensory bladder urgency, or hyperreflexic bladder. These uses include, but are not limited to, those for bladder activities and instabilities in which the urinary urgency is associated with prostatitis, prostatic hypertrophy, interstitial cystitis, urinary tract infections or vaginitis. The methods of this invention may also be used to assist in inhibition or correction of the conditions of Frequency-Urgency Syndrome, and lazy bladder, also known as infrequent voiding syndrome. The methods of this invention may also be used to treat, prevent, inhibit, or limit the urinary incontinence, urinary instability or urinary urgency associated with or resulting from administrations of other medications, including diuretics, vasopressin antagonists, anticholinergic agents, sedatives or hypnotic agents, narcotics, alpha-adrenergic agonists, alpha-adrenergic antagonists, or calcium channel blockers.

Moreover, compounds of the invention are useful in the treatment of pain, for example, neuropathic pain, inflammatory pain, cancer pain, migraine pain, and musculoskeletal pain. The compounds are also useful to treat conditions, which may themselves be the origin of pain, for example, inflammatory conditions, including arthritic conditions (e.g., rheumatoid arthritis, rheumatoid spondylitis, osteoarthritis and gouty arthritis) and non-articular inflammatory conditions (e.g., herniated, ruptured and prolapsed disc syndrome, bursitis, tendonitis, tenosynovitis, fibromyalgia syndrome, and other conditions associated with ligamentous sprain and regional musculoskeletal strain). Particularly preferred compounds of the invention are less ulcerogenic than other anti-inflammatory agents (e.g., ibuprofen, naproxen and aspirin). Furthermore, the compounds of the invention are useful in treating conditions and pain associated with abnormally raised skeletal muscle tone.

Physiological pain is an important protective mechanism designed to warn of danger from potentially injurious stimuli from the external environment. The system operates through a specific set of primary sensory neurons and is activated by noxious stimuli via peripheral transducing mechanisms (see Millan, 1999, Prog. Neurobiol., 57, 1-164 for a review). These sensory fibers are known as nociceptors and are characteristically small diameter axons with slow conduction velocities. Nociceptors encode the intensity, duration and quality of noxious stimulus and by virtue of their topographically organized projection to the spinal cord, the location of the stimulus. The nociceptors are found on nociceptive nerve fibers of which there are two main types, A-delta fibers (myelinated) and C fibers (non-myelinated). The activity generated by nociceptor input is transferred, after complex processing in the dorsal horn, either directly, or via brain stem relay nuclei, to the ventrobasal thalamus and then on to the cortex, where the sensation of pain is generated.

Pain may generally be classified as acute or chronic. Acute pain begins suddenly and is short-lived (usually twelve weeks or less). It is usually associated with a specific cause such as a specific injury and is often sharp and severe. It is the kind of pain that can occur after specific injuries resulting from surgery, dental work, a strain or a sprain. Acute pain does not generally result in any persistent psychological response. In contrast, chronic pain is long-term pain, typically persisting for more than three months and leading to significant psychological and emotional problems. Common examples of chronic pain are neuropathic pain (e.g. painful diabetic neuropathy, post-herpetic neuralgia), carpal tunnel syndrome, back pain, headache, cancer pain, arthritic pain and chronic post-surgical pain.

When a substantial injury occurs to body tissue, via disease or trauma, the characteristics of nociceptor activation are altered and there is sensitization in the periphery, locally around the injury and centrally where the nociceptors terminate. These effects lead to a heightened sensation of pain. In acute pain these mechanisms can be useful, in promoting protective behaviors which may better enable repair processes to take place. The normal expectation would be that sensitivity returns to normal once the injury has healed. However, in many chronic pain states, the hypersensitivity far outlasts the healing process and is often due to nervous system injury. This injury often leads to abnormalities in sensory nerve fibers associated with maladaptation and aberrant activity (Woolf & Salter, 2000, Science, 288, 1765-1768).

Clinical pain is present when discomfort and abnormal sensitivity feature among the patient's symptoms. Patients tend to be quite heterogeneous and may present with various pain symptoms. Such symptoms include: 1) spontaneous pain which may be dull, burning, or stabbing; 2) exaggerated pain responses to noxious stimuli (hyperalgesia); and 3) pain produced by normally innocuous stimuli (allodynia—Meyer et al., 1994, Textbook of Pain, 13-44). Although patients suffering from various forms of acute and chronic pain may have similar symptoms, the underlying mechanisms may be different and may, therefore, require different treatment strategies. Pain can also therefore be divided into a number of different subtypes according to differing pathophysiology, including nociceptive, inflammatory and neuropathic pain.

Nociceptive pain is induced by tissue injury or by intense stimuli with the potential to cause injury. Pain afferents are activated by transduction of stimuli by nociceptors at the site of injury and activate neurons in the spinal cord at the level of their termination. This is then relayed up the spinal tracts to the brain where pain is perceived (Meyer et al., 1994, Textbook of Pain, 13-44). The activation of nociceptors activates two types of afferent nerve fibers. Myelinated A-delta fibers transmit rapidly and are responsible for sharp and stabbing pain sensations, whilst unmyelinated C fibers transmit at a slower rate and convey a dull or aching pain. Moderate to severe acute nociceptive pain is a prominent feature of pain from central nervous system trauma, strains/sprains, burns, myocardial infarction and acute pancreatitis, post-operative pain (pain following any type of surgical procedure), post-traumatic pain, renal colic, cancer pain and back pain. Cancer pain may be chronic pain such as tumor related pain (e.g. bone pain, headache, facial pain or visceral pain) or pain associated with cancer therapy (e.g. postchemotherapy syndrome, chronic post-surgical pain syndrome or post radiation syndrome). Cancer pain may also occur in response to chemotherapy, immunotherapy, hormonal therapy or radiotherapy. Back pain may be due to herniated or ruptured intervertebral discs or abnormalities of the lumber facet joints, sacroiliac joints, paraspinal muscles or the posterior longitudinal ligament. Back pain may resolve naturally but in some patients, where it lasts over 12 weeks, it becomes a chronic condition which can be particularly debilitating.

Neuropathic pain is currently defined as pain initiated or caused by a primary lesion or dysfunction in the nervous system. Nerve damage can be caused by trauma and disease and thus the term 'neuropathic pain' encompasses many disorders with diverse aetiologies. These include, but are not limited to, peripheral neuropathy, diabetic neuropathy, post herpetic neuralgia, trigeminal neuralgia, back pain, cancer neuropathy, HIV neuropathy, phantom limb pain, carpal tunnel syndrome, central post-stroke pain and pain associated with chronic alcoholism, hypothyroidism, uremia, multiple sclerosis, spinal cord injury, Parkinson's disease, epilepsy and vitamin deficiency. Neuropathic pain is pathological as it has no protective role. It is often present well after the original cause has dissipated, commonly lasting for years, significantly decreasing a patient's quality of life (Woolf and Mannion, 1999, Lancet, 353, 1959-1964). The symptoms of neuropathic pain are difficult to treat, as they are often heterogeneous even between patients with the same disease (Woolf & Decosterd, 1999, Pain Supp., 6, S141-S147; Woolf and Mannion, 1999, Lancet, 353, 1959-1964). They include spontaneous pain, which can be continuous, and paroxysmal or abnormal evoked pain, such as hyperalgesia (increased sensitivity to a noxious stimulus) and allodynia (sensitivity to a normally innocuous stimulus).

The inflammatory process is a complex series of biochemical and cellular events, activated in response to tissue injury or the presence of foreign substances, which results in swelling and pain (Levine and Taiwo, 1994, Textbook of Pain, 45-56). Arthritic pain is the most common inflammatory pain. Rheumatoid disease is one of the commonest chronic inflammatory conditions in developed countries and rheumatoid arthritis is a common cause of disability. The exact aetiology of rheumatoid arthritis is unknown, but current hypotheses suggest that both genetic and microbiological factors may be important (Grennan & Jayson, 1994, Textbook of Pain, 397-407). It has been estimated that almost 16 million Americans have symptomatic osteoarthritis (OA) or degenerative joint disease, most of whom are over 60 years of age, and this is expected to increase to 40 million as the age of the population increases, making this a public health problem of enormous magnitude (Houge & Mersfelder, 2002, Ann Pharmacother., 36, 679-686; McCarthy et al., 1994, Textbook of Pain, 387-395). Most patients with osteoarthritis seek medical attention because of the associated pain. Arthritis has a significant impact on psychosocial and physical function and is known to be the leading cause of disability in later life. Ankylosing spondylitis is also a rheumatic disease that causes arthritis of the spine and sacroiliac joints. It varies from intermittent episodes of back pain that occur throughout life to a severe chronic disease that attacks the spine, peripheral joints and other body organs.

Another type of inflammatory pain is visceral pain which includes pain associated with inflammatory bowel disease (IBD). Visceral pain is pain associated with the viscera, which encompass the organs of the abdominal cavity. These organs include the sex organs, spleen and part of the digestive system. Pain associated with the viscera can be divided into digestive visceral pain and non-digestive visceral pain. Commonly encountered gastrointestinal (GI) disorders that cause pain include functional bowel disorder (FBD) and inflammatory bowel disease (IBD). These GI disorders include a wide range of disease states that are currently only moderately controlled, including, in respect of FBD, gastro-esophageal reflux, dyspepsia, irritable bowel syndrome (IBS) and functional abdominal pain syndrome (FAPS), and, in respect of IBD, Crohn's disease, ileitis and ulcerative colitis, all of which regularly produce visceral pain. Other types of visceral pain include the pain associated with dysmenorrhea, cystitis and pancreatitis and pelvic pain.

It should be noted that some types of pain have multiple aetiologies and thus can be classified in more than one area, e.g. back pain and cancer pain have both nociceptive and neuropathic components.

Other types of pain include:
pain resulting from musculo-skeletal disorders, including myalgia, fibromyalgia, spondylitis, sero-negative (non-rheumatoid) arthropathies, non-articular rheumatism, dystrophinopathy, glycogenolysis, polymyositis and pyomyositis;
heart and vascular pain, including pain caused by angina, myocardical infarction, mitral stenosis, pericarditis, Raynaud's phenomenon, scleredoma and skeletal muscle ischemia;
head pain, such as migraine (including migraine with aura and migraine without aura), cluster headache, tension-type headache mixed headache and headache associated with vascular disorders; and orofacial pain, including dental pain, otic pain, burning mouth syndrome and temporomandibular myofascial pain.

The compounds of the invention are also of use in treating anxiety (e.g. anxiety disorders). Anxiety disorders are defined in the Diagnostic and Statistical Manual of Mental Disorders (Third Edition-revised 1987, published by the American Psychiatric Association, Washington, D.C., see, pages 235 to 253), as psychiatric conditions having symptoms of anxiety and avoidance behavior as characteristic features. Included amongst such disorders are generalized anxiety disorder, simple phobia and panic disorder.

Anxiety also occurs as a symptom associated with other psychiatric disorders, for example, obsessive compulsive disorder, post-traumatic stress disorder, schizophrenia, mood disorders and major depressive disorders, and with organic clinical conditions including, but not limited to, Parkinson's disease, multiple sclerosis, and other physically incapacitating disorders.

In view of the above-noted discovery, the present invention provides compounds, compositions, and methods for increasing ion flux in voltage-dependent potassium channels, particularly those channels responsible for the M-current. As used herein, the term "M-current," "channels responsible for the M-current" and the like, refers to a slowly activating, non-inactivating, slowly deactivating voltage-gated $K^+$ channel. M-current is active at voltages close to the threshold for action potential generation in a wide variety of neuronal cells, and thus, is an important regulator of neuronal excitability.

Recently, members of the voltage-dependent potassium channel family were shown to be directly involved in diseases of the central or peripheral nervous system. The fused ring heterocycles provided herein are now shown to act as potassium channel modulators.

In some embodiments, the present invention provides a method for the treatment of a central or peripheral nervous system disorder or condition through modulation of a voltage-dependent potassium channel. In this method, a subject in need of such treatment is administered an effective amount of a compound having any of Formulas I, II, III, IV, V, VI, VII, VIII, IX, IXa, IXa-1, IXa-2, IXa-3, IXa-4, IXa-5, IXa-6, IXa-7, IXb-1, IXb-2, IXb-3, IXb-3, IXb-4, IXb-5, IXc, IXc-1, IXc-2, IXd-1 and IXd-2 or a compound of any of sets 1-33. In one embodiment, the present invention provides a method of treating, preventing, inhibiting or ameliorating a central or peripheral nervous system disorder or condition through modulation of a potassium ion channel. The method includes administering to a subject (i.e. a mammal or a human) in need of such treatment an effective amount of a compound of any of Formulas IX, IXa, IXa-1, IXa-2, IXa-3, IXa-4, IXa-5, IXa-6, IXa-7, IXb-1, IXb-2, IXb-3, IXb-3, IXb-4, IXb-5, IXc, IXc-1, IXc-2, IXd-1 and IXd-2 or a compound of any of sets 1-33.

The compounds provided herein are useful as potassium channel modulators and find therapeutic utility via modulation of voltage-dependent potassium channels in the treatment of diseases or conditions. The potassium channels targets for the compounds of the invention are described herein as voltage-dependent potassium channels such as the KCNQ potassium channels. As noted above, these channels may include homomultimers and heteromultimers of KCNQ2, KCNQ3, KCNQ4, KCNQ5 and KCNQ6. A heteromultimer of two proteins, e.g., KCNQ2 and KCNQ3 is referred to as, for example, KCNQ2/3, KCNQ3/5, etc. The conditions that can be treated with the compounds and compositions of the present invention may include, but are not limited to, central or peripheral nervous system disorders (e.g., migraine, ataxia, Parkinson's disease, bipolar disorders, trigeminal neuralgia, spasticity, mood disorders, brain tumors, psychotic disorders, myokymia, seizures, epilepsy, hearing and vision loss, Alzheimer's disease, age-related memory loss, learning deficiencies, anxiety, and motor neuron diseases). The compounds and compositions of the present invention may also serve as neuroprotective agents (e.g., to prevent stroke and the like). In a preferred embodiment, the condition or disorder to be treated is epilepsy or seizures. In another preferred embodiment, the condition or disorder is hearing loss.

In therapeutic use for the treatment of epilepsy or other neurological conditions, the compounds utilized in the pharmaceutical method of the invention are administered at the initial dosage of about 0.001 mg/kg to about 1000 mg/kg daily. A daily dose range of about 0.1 mg/kg to about 100 mg/kg is more typical. The dosages, however, may be varied depending upon the requirements of the patient, the severity of the condition being treated, and the compound being employed. Determination of the proper dosage for a particular situation is within the skill of the practitioner. Generally, treatment is initiated with smaller dosages, which are less than the optimum dose of the compound. Thereafter, the dosage is increased by small increments until the optimum effect under circumstances is reached. For convenience, the total daily dosage may be divided and administered in portions during the day, if desired.

In a group of embodiments, the present invention provides a compound as described herein or a compound of any of sets 1-33 above, or a pharmaceutically acceptable salt, hydrate or solvate thereof, for use as a medicament. In one embodiment, the compound has any of Formulas I, II, III, IV, V, VI, VII, VIII, IX, IXa, IXa-1, IXa-2, IXa-3, IXa-4, IXa-5, IXa-6, IXa-7, IXb-1, IXb-2, IXb-3, IXb-3, IXb-4, IXb-5, IXc, IXc-1, IXc-2, IXd-1 and IXd-2. In another embodiment, the compound has any of Formulas IX, IXa, IXa-1, IXa-2, IXa-3, IXa-4, IXa-5, IXa-6, IXa-7, IXb-1, IXb-2, IXb-3, IXb-3, IXb-4, IXb-5, IXc, IXc-1, IXc-2, IXd-1 and IXd-2.

In another group of embodiments, the present invention provides a compound as described herein or a compound of any of sets 1-33 above, or a pharmaceutically acceptable salt, hydrate or solvate thereof, for use in treating, preventing, inhibiting or ameliorating a central or peripheral nervous system disorder or condition. Exemplary disorders or conditions include migraine, ataxia, Parkinson's disease, bipolar disorders, trigeminal neuralgia, spasticity, mood disorders, brain tumors, psychotic disorders, myokymia, seizures, epilepsy, stroke, hearing and vision loss, Alzheimer's disease, age-related memory loss, learning deficiencies, retinal degeneration, pain anxiety, neuronal degeneration, motor neuron diseases and urinary incontinence. In one embodiment, the compound has any of Formulas I, II, III, IV, V, VI, VII, VIII, IX, IXa, IXa-1, IXa-2, IXa-3, IXa-4, IXa-5, IXa-6, IXa-7, IXb-1, IXb-2, IXb-3, IXb-3, IXb-4, IXb-5, IXc, IXc-1, IXc-2, IXd-1 and IXd-2.

In yet another group of embodiments, the present invention provides a compound as described herein or a compound of any of sets 1-33 above, or a pharmaceutically acceptable salt, hydrate or solvate thereof, in the manufacture of a medicament for treating, preventing, inhibiting or ameliorating a central or peripheral nervous system disorder or condition. Exemplary disorders or conditions include migraine, ataxia, Parkinson's disease, bipolar disorders, trigeminal neuralgia, spasticity, mood disorders, brain tumors, psychotic disorders, myokymia, seizures, epilepsy, stroke, hearing and vision loss, Alzheimer's disease, age-related memory loss, learning deficiencies, retinal degeneration, pain anxiety, neuronal degeneration, motor neuron diseases and urinary incontinence. In one embodiment, the compound has any of Formulas I, II, III, IV, V, VI, VII, VIII, IX, IXa, IXa-1, IXa-2, IXa-3, IXa-4, IXa-5, IXa-6, IXa-7, IXb-1, IXb-2, IXb-3, IXb-3, IXb-4, IXb-5, IXc, IXc-1, IXc-2, IXd-1 and IXd-2.

EXAMPLES

The following examples are offered to illustrate, but not to limit the claimed invention.

Compounds within the scope of this invention can be synthesized as described below, using a variety of reactions known to the skilled artisan. One skilled in the art will also recognize that alternative methods may be employed to synthesize the target compounds of this invention, and that the approaches described within the body of this document are not exhaustive, but do provide broadly applicable and practical routes to compounds of interest.

Certain molecules claimed in this patent can exist in different enantiomeric, diastereomeric and tautomeric forms and all such variants of these compounds are claimed.

Those skilled in the art will also recognize that during standard work up procedures in organic chemistry, acids and bases are frequently used. Salts of the parent compounds are sometimes produced, if they possess the necessary intrinsic acidity or basicity, during the experimental procedures described within this patent.

In the examples below, unless otherwise stated, temperatures are given in degrees Celsius (° C.); operations were carried out at room or ambient temperature (typically a range of from about 18-25° C.; evaporation of solvent was carried out using a rotary evaporator under reduced pressure (typically, 4.5-30 mmHg) with a bath temperature of up to 60° C.; the course of reactions was typically followed by TLC and reaction times are provided for illustration only; melting points are uncorrected; products exhibited satisfactory $^1$H-NMR and/or microanalytical data; yields are provided for illustration only; and the following conventional abbreviations are also used: mp (melting point), L (liter(s)), mL (milliliters), mmol (millimoles), g (grams), mg (milligrams), min (minutes), and h (hours).

The compounds were prepared using five related methods as described in detail below. Examples 1-5 illustrate each method along with the compounds prepared using that method.

Example 1

Preparation of N-3-cyclopropyl-6-fluoroimidazo[1,2-a]pyridin-2-yl)-3,3-dimethylbutanamide (g)

Method 1

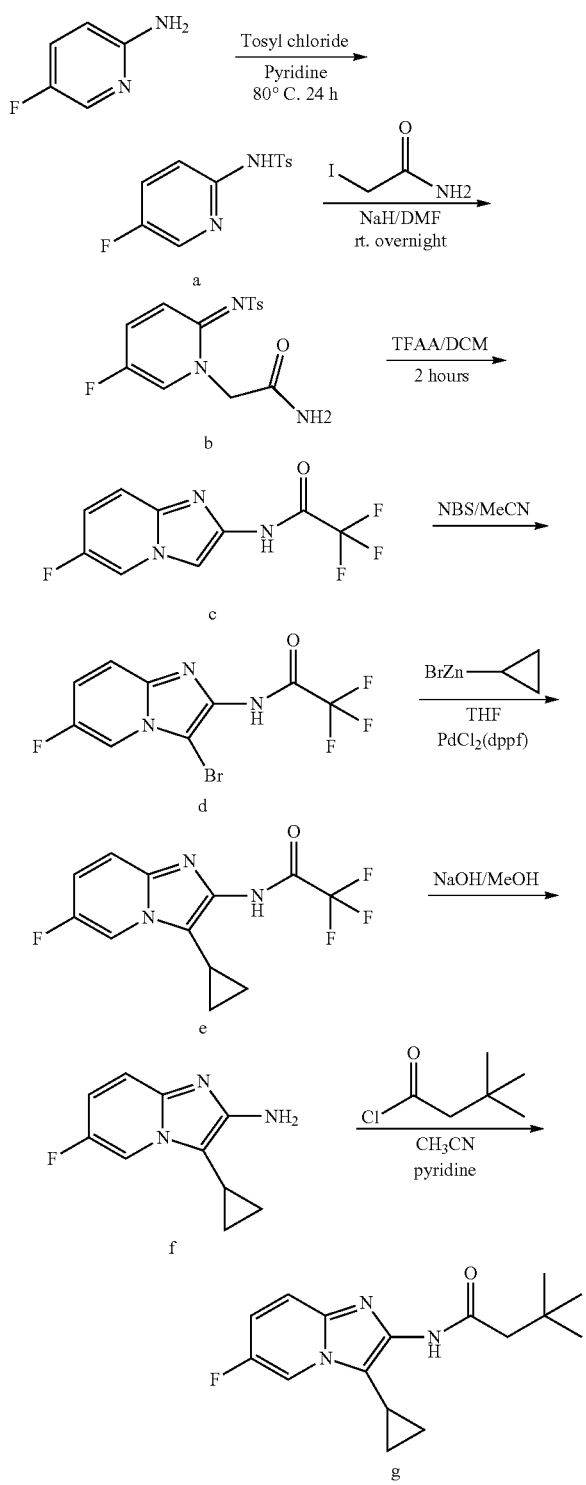

Synthesis of N-(5-Fluoro-pyridin-2-yl)-4-methyl-benzenesulfonamide (a)

2-amino-5-fluoropyridine (25 g, 0.22 mol) in pyridine (100 mL) was treated portion wise with p-toluenesulfonyl chloride (47.5 g, 0.25 mol) and heated at 80° C. for 2 hours. The cooled material was concentrated to remove the majority of pyridine. The resulting viscous solution was diluted with 200 ml of ethyl acetate then 200 ml of water. The resulting suspension was stirred for about an hour to break up the solids then filtered. The filter cake was washed with water then cold ethyl acetate, dried to afford 59 g of a light brown solid. Rf 0.43, 50% ethyl acetate/hexanes; MS m/z 266 (M+H).

Synthesis of 2-(5-fluoro-2-(tosylimino)pyridin-1 (2H)-yl)acetamide (b)

Sodium hydride (5.0 g, 0.21 mol) in N,N-Dimethylformamide (370 mL) was treated portion wise with N-(5-Fluoro-pyridin-2-yl)-4-methyl-benzenesulfonamide (compound a, 50 g, 0.2 mol). After stirring for 20 minutes, iodoacetamide (30 g, 0.2 mol) was added in one portion. The reaction stirred overnight at room temperature. The solvent was removed to give a brown solid. The crude material was diluted with 500 ml of ethyl acetate and 100 mL of water and stirred for 2 hours. The solid was collected by filtration and dried to afford 36 g of 2-(5-fluoro-2-(tosylimino)pyridin-1(2H)-yl)acetamide. Rf 0.37, neat ethyl acetate MS m/z 324 (M+H).

Synthesis of 2,2,2-trifluoro-N-(6-fluoroimidazo[1,2-a]pyridin-2-yl)acetamide (c)

2-(5-fluoro-2-(tosylimino)pyridin-1(2H)-yl)acetamide (compound b, 36 g, 0.11 mol) was taken up in 360 mL dichloromethane and treated with 135 ml of TFAA and stirred at room temperature for an hour. Solvent was removed and the residue taken up in ethyl acetate and sat. sodium bicarbonate and stirred until gas evolution ceased. The organic phase was separated, dried over sodium sulfate, filtered and concentrated to a light yellow solid (33 g). The crude solid was purified by flash chromatography (0-100% ethyl acetate/hexane) to give 17 g of 2,2,2-trifluoro-N-(6-fluoroimidazo[1,2-a]pyridin-2-yl)-acetamide. Rf 0.39, 50% ethyl acetate/hexanes; MS m/z 248 (M+H).

Synthesis of N-(3-Bromo-6-fluoro-imidazo[1,2-a]pyridin-2-yl)-2,2,2-trifluoro-acetamide (d)

N-Bromosuccinimide (2.96 g, 0.0166 mol) was added to a solution of 2,2,2-Trifluoro-N-(6-fluoro-imidazo[1,2-a]pyridin-2-yl)-acetamide (compound c, 3.74 g, 0.0151 mol) in acetonitrile (70 mL) and stirred at room temperature. The reaction mixture was stirred at room temperature for 15 minutes. Reaction mixture was concentrated under reduced pressure, crude product taken up in ethyl acetate, washed with water, organic layer collected, dried over Na2SO4, concentrated in vacuo and crude product purified by column chromatography (50% ethyl acetate/hexanes) to give product as an off white solid. Rf 0.47, 50% ethyl acetate/hexanes; MS m/z 327 (M+H).

Synthesis of N-(3-cyclopropyl-6-fluoro-imidazo[1,2-a]pyridin-2-yl)-2,2,2-trifluoro-acetamide (e)

Tetrakis(triphenylphosphine)palladium(0) (0.0797 g, 0.000069 mol) was added to a solution of 0.50 M of cyclopropylzinc bromide in tetrahydrofuran (4.1 mL) and N-(3- bromo-6-fluoro-imidazo[1,2-a]pyridin-2-yl)-2,2,2-trifluoro-acetamide (compound d, 0.225 g, 0.000690 mol) in tetrahydrofuran (20.0 mL) and the reaction was heated to reflux for 3 hours. An additional 0.50 M of cyclopropylzinc bromide (4.1 mL) in tetrahydrofuran and tetrakis(triphenylphosphine)palladium(0)(0.080 g) was added and the mixture was heated to reflux overnight. The reaction was concentrated in vacuo and crude product purified by column chromatography (50% ethyl acetate/hexanes) to give N-(3-cyclopropyl-6-fluoro-imidazo[1,2-a]pyridin-2-yl)-2,2,2-trifluoro-acetamide as a yellow solid. Rf 0.46, 50% ethyl acetate/hexanes; MS m/z 287 (M+H).

Synthesis of 3-Cyclopropyl-6-fluoro-imidazo[1,2-a]pyridin-2-ylamine (f)

6.00 M of Sodium hydroxide in water (1.0 mL) was added to a solution of N-(3-Cyclopropyl-6-fluoro-imidazo[1,2-a]pyridin-2-yl)-2,2,2-trifluoro-acetamide (compound e, 0.197 g, 0.000617 mol) in Methanol (2.00 mL, 0.0494 mol) and Tetrahydrofuran (2.0 mL, 0.0246 mol) and the reaction mixture was stirred at 55° C. for 36 hours. The reaction mixture concentrated in vacuo to dryness and crude product purified by column chromatography (5% methanol/dichloromethane) as a yellow solid. Rf 0.41, 5% methanol/dichloromethane; MS m/z 192 (M+H).

Synthesis of N-(3-Cyclopropyl-6-fluoro-imidazo[1,2-a]pyridin-2-yl)-3,3-dimethyl-butyramide (g)

Tert-butyl acetyl chloride (0.040 mL, 0.00029 mol) was added to a solution of 3-Cyclopropyl-6-fluoro-imidazo[1,2-a]pyridin-2-ylamine (compound f, 0.054 g, 0.00027 mol) in acetonitrile (5.00 mL) containing pyridine (0.0637 g, 0.00081 mol) and the mixture stirred at room temperature for 1 hour. The reaction mixture was concentrated in vacuo and crude product purified by column chromatography (50% ethyl acetate/hexanes to neat ethyl acetate) to give N-(3-cyclopropyl-6-fluoro-imidazo[1,2-a]pyridin-2-yl)-3,3-dimethyl-butyramide as a yellow solid. Rf 0.41, 5% methanol/dichloromethane; MS m/z 289 (M+H). SH-SY5Y_EC50 (μM): 2.5464.

The following compounds were prepared according to the procedures of Method 1. In one embodiment, 2-aminopyridazine was used as the starting material for the preparation of compounds 67, 68, 74, 76 and 78, which contain a imidazo[1,2-b]pyridazin moiety. The number next to each compound listed below corresponds to the compound number listed in Table 1.

Following is a List of the Compounds Prepared by Method 1:

2,2,2-trifluoro-N-(5-methylimidazo[1,2-a]pyridin-2-yl)acetamide 8
3,3-dimethyl-N-(5-methylimidazo[1,2-a]pyridin-2-yl)butanamide 9
2,2,2-trifluoro-N-(6-fluoroimidazo[1,2-a]pyridin-2-yl)acetamide 10
2,2,2-trifluoro-N-(6-fluoro-3-iodoimidazo[1,2-a]pyridin-2-yl)acetamide 11
2,2,2-trifluoro-N-(5-(trifluoromethyl)imidazo[1,2-a]pyridin-2-yl)acetamide 12
2-(4-fluorophenyl)-N-(5-(trifluoromethyl)imidazo[1,2-a]pyridin-2-yl)acetamide 13
N-(3-cyclopropyl-6-fluoroimidazo[1,2-a]pyridin-2-yl)-3,3-dimethylbutanamide 14
N-(6-fluoro-3-neopentylimidazo[1,2-a]pyridin-2-yl)-3,3-dimethylbutanamide 15
N-(6-fluoro-3-(4-fluorobenzyl)imidazo[1,2-a]pyridin-2-yl)-3,3-dimethylbutanamide 16
N-(6-fluoro-3-neopentylimidazo[1,2-a]pyridin-2-yl)-2-(4-fluorophenyl)acetamide 17
N-(6-fluoro-3-(4-fluorobenzyl)imidazo[1,2-a]pyridin-2-yl)-2-(4-fluorophenyl)acetamide 18
3,3-dimethyl-N-(3-neopentyl-6-(trifluoromethyl)imidazo[1,2-a]pyridin-2-yl)butanamide 19
N-(3-neopentyl-6-(trifluoromethyl)imidazo[1,2-a]pyridin-2-yl)-2-phenylacetamide 20
2-(4-fluorophenyl)-N-(3-neopentyl-6-(trifluoromethyl)imidazo[1,2-a]pyridin-2-yl)acetamide 21
N-(3-neopentyl-6-(trifluoromethyl)imidazo[1,2-a]pyridin-2-yl)-2-(4-phenoxyphenyl)acetamide 22
4,4,4-trifluoro-3-methyl-N-(3-neopentyl-6-(trifluoromethyl)imidazo yl)butanamide 23
4,4-dimethyl-N-(3-neopentyl-6-(trifluoromethyl)imidazo[1,2-a]pyridin-2-yl)pentanamide 24
N-(3-neopentyl-6-(trifluoromethyl)imidazo[1,2-a]pyridin-2-yl)-2-(3-(trifluoromethoxy)phenyl)acetamide 25
N-(3-neopentyl-6-(trifluoromethyl)imidazo[1,2-a]pyridin-2-yl)-2-(4-(trifluoromethoxy)phenyl)acetamide 26
2-(4-chlorophenyl)-N-(3-neopentyl-6-(trifluoromethyl)imidazo[1,2-a]pyridin-2-yl)acetamide 27
N-(6-fluoro-3-(4-(trifluoromethyl)benzyl)imidazo[1,2-a]pyridin-2-yl)-3,3-dimethylbutanamide 28
4,4,4-trifluoro-N-(6-fluoro-3-(4-(trifluoromethyl)benzyl)imidazo[1,2-a]pyridin-2-yl)-3-methylbutanamide 29
N-(6-fluoro-3-(4-(trifluoromethyl)benzyl)imidazo[1,2-a]pyridin-2-yl)-2,3-dimethylbutanamide 30
N-(3-isopentyl-6-(trifluoromethyl)imidazo[1,2-a]pyridin-2-yl)-3,3-dimethylbutanamide 31
N-(3-(cyclohexylmethyl)-6-(trifluoromethyl)imidazo[1,2-a]pyridin-2-yl)-3,3-dimethylbutanamide 32
N-(3-cyclohexyl-6-(trifluoromethyl)imidazo[1,2-a]pyridin-2-yl)-3,3-dimethylbutanamide 33
2-(1-methylcyclopentyl)-N-(3-neopentyl-6-(trifluoromethyl)imidazo[1,2-a]pyridin-2-yl)acetamide 34
2-(3-chlorophenyl)-N-(3-neopentyl-6-(trifluoromethyl)imidazo[1,2-a]pyridin-2-yl)acetamide 35
N-(3-isopentyl-6-(trifluoromethyl)imidazo[1,2-a]pyridin-2-yl)-2-phenylacetamide 36
N-(3-(cyclohexylmethyl)-6-(trifluoromethyl)imidazo[1,2-a]pyridin-2-yl)-2-phenylacetamide 37
N-(3-cyclohexyl-6-(trifluoromethyl)imidazo[1,2-a]pyridin-2-yl)-2-phenylacetamide 38
2-(4-fluorophenyl)-N-(3-isopentyl-6-(trifluoromethyl)imidazo[1,2-a]pyridin-2-yl)acetamide 39
N-(3-(cyclohexylmethyl)-6-(trifluoromethyl)imidazo[1,2-a]pyridin-2-yl)-2-(4-fluorophenyl)acetamide 40
N-(3-cyclohexyl-6-(trifluoromethyl)imidazo[1,2-a]pyridin-2-yl)-2-(4-fluorophenyl)acetamide 41
2-(3-chlorophenyl)-N-(3-isopentyl-6-(trifluoromethyl)imidazo[1,2-a]pyridin-2-yl)acetamide 42
2-(3-chlorophenyl)-N-(3-(cyclohexylmethyl)-6-(trifluoromethyl)imidazo[1,2-a]pyridin-2-yl)acetamide 43
2-(3-chlorophenyl)-N-(3-cyclohexyl-6-(trifluoromethyl)imidazo[1,2-a]pyridin-2-yl)acetamide 44
N-(3-isopentyl-6-(trifluoromethyl)imidazo[1,2-a]pyridin-2-yl)-2-(1-methylcyclopentyl)acetamide 45
N-(3-(cyclohexylmethyl)-6-(trifluoromethyl)imidazo[1,2-a]pyridin-2-yl)-2-(1-methylcyclopentyl)acetamide 46
N-(3-cyclohexyl-6-(trifluoromethyl)imidazo[1,2-a]pyridin-2-yl)-2-(1-methylcyclopentyl)acetamide 47
N-(3-cyclopentyl-6-(trifluoromethyl)imidazo[1,2-a]pyridin-2-yl)-3,3-dimethylbutanamide 48

N-(3-cyclopentyl-6-(trifluoromethyl)imidazo[1,2-a]pyridin-2-yl)-2-phenyl acetamide 49
N-(3-cyclopentyl-6-(trifluoromethyl)imidazo[1,2-a]pyridin-2-yl)-2-(4-fluorophenyl)acetamide 50
N-(3-neopentyl-6-(trifluoromethyl)imidazo[1,2-a]pyridin-2-yl)cyclopentanecarboxamide 51
N-(3-(cyclohexylmethyl)-6-(trifluoromethyl)imidazo[1,2-a]pyridin-2-yl)cyclopentanecarboxamide 52
N-(3-isopentyl-6-(trifluoromethyl)imidazo[1,2-a]pyridin-2-yl)cyclopentanecarboxamide 53
N-(3-cyclohexyl-6-(trifluoromethyl)imidazo[1,2-a]pyridin-2-yl)cyclopentanecarboxamide 54
N-(3-cyclopentyl-6-(trifluoromethyl)imidazo[1,2-a]pyridin-2-yl)cyclopentanecarboxamide 55
N-(3-cyclopentyl-6-(trifluoromethyl)imidazo[1,2-a]pyridin-2-yl)-2-(1-methylcyclopentyl)acetamide 56
2-cyclopropyl-N-(3-neopentyl-6-(trifluoromethyl)imidazo[1,2-a]pyridin-2-yl)acetamide 57
3-methyl-N-(3-neopentyl-6-(trifluoromethyl)imidazo[1,2-a]pyridin-2-yl)pentanamide 58
N-(3-neopentyl-6-(trifluoromethyl)imidazo[1,2-a]pyridin-2-yl)cyclohexanecarboxamide 59
3,3,3-trifluoro-N-(3-neopentyl-6-(trifluoromethyl)imidazo[1,2-a]pyridin-2-yl)propanamide 60
N-(3-neopentyl-6-(trifluoromethyl)imidazo[1,2-a]pyridin-2-yl)-2-(4-(trifluoromethyl)phenyl)acetamide 61
N-(3-neopentyl-6-(trifluoromethyl)imidazo[1,2-a]pyridin-2-yl)acetamide 62
3-methyl-N-(3-neopentyl-6-(trifluoromethyl)imidazo[1,2-a]pyridin-2-yl)butanamide 63
N-(3-neopentyl-6-(trifluoromethyl)imidazo[1,2-a]pyridin-2-yl)cyclopropanecarboxamide 64
N-(3-cyclopropyl-6-(trifluoromethyl)imidazo[1,2-a]pyridin-2-yl)-3,3-dimethylbutanamide 65
N-(3-(cyclohexylmethyl)-6-fluoroimidazo[1,2-a]pyridin-2-yl)-3,3-dimethylbutanamide 66
3,3-dimethyl-N-(6-methyl-3-neopentylimidazo[1,2-b]pyridazin-2-yl)butanamide 67
4,4,4-trifluoro-3-methyl-N-(6-methyl-3-neopentylimidazo[1,2-b]pyridazin-2-yl)butanamide 68
N-(3-cyclopropyl-6-(trifluoromethyl)imidazo[1,2-a]pyridin-2-yl)-4,4,4-trifluoro-3-methylbutanamide 69
N-(3-cyclopropyl-6-(trifluoromethyl)imidazo[1,2-a]pyridin-2-yl)-2-(4-fluorophenyl)acetamide 70
2-(2,2-difluorocyclopentyl)-N-(3-neopentyl-6-(trifluoromethyl)imidazo[1,2-a]pyridin-2-yl)acetamide 71
2-cyclopentyl-N-(3-neopentyl-6-(trifluoromethyl)imidazo[1,2-a]pyridin-2-yl)acetamide 72
4,4-difluoro-N-(3-neopentyl-6-(trifluoromethyl)imidazo[1,2-a]pyridin-2-yl)cyclohexanecarboxamide 73
N-(3-cyclopropyl-6-methylimidazo[1,2-b]pyridazin-2-yl)-3,3-dimethylbutanamide 74
N-(3-cyclopropyl-6-(trifluoromethyl)imidazo[1,2-a]pyridin-2-yl)-4,4-difluorocyclohexanecarboxamide 75
N-(3-cyclopropyl-6-methylimidazo[1,2-b]pyridazin-2-yl)-4,4,4-trifluoro-3-methylbutanamide 76
N-(3-cyclopropyl-6-(trifluoromethyl)imidazo[1,2-a]pyridin-2-yl)-2-(3,4-difluorophenyl)acetamide 77
N-(3-cyclopropyl-6-methylimidazo[1,2-b]pyridazin-2-yl)-4,4-difluorocyclohexanecarboxamide 78
N-(3-cyclopropyl-6-(trifluoromethyl)imidazo[1,2-a]pyridin-2-yl)-2-(2,4-difluorophenyl)acetamide 79
N-(3-cyclopropyl-6-(trifluoromethyl)imidazo[1,2-a]pyridin-2-yl)-2-(3,5-difluorophenyl)acetamide 80
N-(3-cyclopropyl-5-methylimidazo[1,2-a]pyridin-2-yl)-3,3-dimethylbutanamide 81
3,3-dimethyl-N-(3-(thiazol-2-yl)-6-(trifluoromethyl)imidazo[1,2-a]pyridin-2-yl)butanamide 82
4,4,4-trifluoro-3-methyl-N-(3-(thiazol-2-yl)-6-(trifluoromethyl)imidazo[1,2-a]pyridin-2-yl)butanamide 83
2-(4-fluorophenyl)-N-(3-(thiazol-2-yl)-6-(trifluoromethyl)imidazo[1,2-a]pyridin-2-yl)acetamide 84
N-(3-cyclopropyl-6-(trifluoromethyl)imidazo[1,2-a]pyridin-2-yl)-2,2-difluorocyclopropanecarboxamide 85
4,4,4-trifluoro-3-methyl-N-(3-neopentylimidazo[1,2-a]pyridin-2-yl)butanamide 86
4,4-difluoro-N-(3-neopentylimidazo[1,2-a]pyridin-2-yl)cyclohexanecarboxamide 87
3,3-dimethyl-N-(3-neopentylimidazo[1,2-a]pyridin-2-yl)butanamide 88
(R)—N-(3-cyclopropyl-6-(trifluoromethyl)imidazo[1,2-a]pyridin-2-yl)-4,4,4-trifluoro-3-methylbutanamide 89
(S)—N-(3-cyclopropyl-6-(trifluoromethyl)imidazo[1,2-a]pyridin-2-yl)-4,4,4-trifluoro-3-methylbutanamide 90

Table 1 sets forth potencies, purity, calculated molecular weights and measured molecular weights of representative compounds of the invention in the SH-SY5Y native cell line in a FLIPR (Fluorometric Imaging Plate Reader) assay, for a selection of compounds. The compound numbers in Table 1 correspond to the respective compound numbers listed above in Example 1.

TABLE 1

| Compound No. | SH-SY5Y EC50, μM | Purity (%) | Molecular Weight | Observed m/z (M + H) |
|---|---|---|---|---|
| 8 | + | 98 | 243.2 | 244.2 |
| 9 | + | 98 | 245.3 | 246.3 |
| 10 | + | 98 | 247.1 | 248.1 |
| 11 | + | 98 | 373.0 | 374.0 |
| 12 | + | 98 | 297.2 | 298.2 |
| 13 | + | 98 | 337.3 | 338.3 |
| 14 | ++ | 95 | 289.3 | 290.3 |
| 15 | ++ | 95 | 319.4 | 320.4 |
| 16 | +++ | 95 | 357.4 | 358.4 |
| 17 | +++ | 95 | 357.4 | 358.4 |
| 18 | +++ | 95 | 395.4 | 396.4 |
| 19 | +++ | 95 | 369.4 | 370.4 |
| 20 | +++ | 95 | 389.4 | 390.4 |
| 21 | +++ | 95 | 407.4 | 408.4 |
| 22 | +++ | 95 | 481.5 | 482.5 |
| 23 | +++ | 95 | 409.4 | 410.4 |
| 24 | +++ | 95 | 383.5 | 384.5 |
| 25 | +++ | 95 | 473.4 | 474.4 |
| 26 | +++ | 95 | 473.4 | 474.4 |
| 27 | +++ | 95 | 423.9 | 424.9 |
| 28 | +++ | 95 | 407.4 | 408.4 |
| 29 | +++ | 90 | 447.3 | 448.3 |
| 30 | ++ | 100 | 407.4 | 408.4 |
| 31 | +++ | 95 | 369.4 | 370.4 |
| 32 | +++ | 95 | 395.5 | 396.5 |
| 33 | +++ | 95 | 381.4 | 382.4 |
| 34 | +++ | 95 | 395.5 | 396.5 |
| 35 | +++ | 95 | 423.9 | 424.9 |
| 36 | +++ | 95 | 389.4 | 390.4 |
| 37 | +++ | 95 | 415.5 | 416.5 |
| 38 | +++ | 95 | 401.4 | 402.4 |
| 39 | +++ | 95 | 407.4 | 408.4 |
| 40 | +++ | 95 | 433.4 | 434.4 |
| 41 | +++ | 95 | 419.4 | 420.4 |
| 42 | +++ | 95 | 423.9 | 424.9 |
| 43 | +++ | 95 | 449.9 | 450.9 |
| 44 | +++ | 95 | 435.9 | 436.9 |
| 45 | +++ | 95 | 395.5 | 396.5 |
| 46 | +++ | 95 | 421.5 | 422.5 |
| 47 | +++ | 95 | 407.5 | 408.5 |
| 48 | +++ | 95 | 367.4 | 368.4 |
| 49 | +++ | 95 | 387.4 | 388.4 |
| 50 | +++ | 95 | 405.4 | 406.4 |
| 51 | +++ | 98 | 367.4 | 368.4 |

TABLE 1-continued

| Compound No. | SH-SY5Y EC50, μM | Purity (%) | Molecular Weight | Observed m/z (M + H) |
|---|---|---|---|---|
| 52 | +++ | 98 | 393.4 | 394.4 |
| 53 | +++ | 98 | 367.4 | 368.4 |
| 54 | +++ | 98 | 379.4 | 380.4 |
| 55 | +++ | 98 | 365.4 | 366.4 |
| 56 | +++ | 95 | 393.4 | 394.4 |
| 57 | +++ | 98 | 353.4 | 354.4 |
| 58 | +++ | 98 | 369.4 | 370.4 |
| 59 | +++ | 98 | 381.4 | 382.4 |
| 60 | +++ | 98 | 381.3 | 382.3 |
| 61 | +++ | 98 | 457.4 | 458.4 |
| 62 | + | 98 | 313.3 | 314.3 |
| 63 | ++ | 95 | 355.4 | 356.4 |
| 64 | ++ | 98 | 339.4 | 340.4 |
| 65 | ++ | 95 | 339.4 | 340.4 |
| 66 | +++ | 95 | 345.5 | 346.5 |
| 67 | +++ | 98 | 316.4 | 317.4 |
| 68 | +++ | 95 | 356.4 | 357.4 |
| 69 | +++ | 95 | 379.3 | 380.3 |
| 70 | +++ | 95 | 377.3 | 378.3 |
| 71 | +++ | 95 | 417.4 | 418.4 |
| 72 | +++ | 95 | 381.4 | 382.4 |
| 73 | +++ | 95 | 417.4 | 418.4 |
| 74 | ++ | 98 | 286.4 | 287.4 |
| 75 | +++ | 95 | 387.3 | 388.3 |
| 76 | + | 98 | 326.3 | 327.3 |
| 77 | +++ | 95 | 395.3 | 396.3 |
| 78 | ++ | 98 | 334.4 | 335.4 |
| 79 | ++ | 95 | 395.3 | 396.3 |
| 80 | +++ | 95 | 395.3 | 396.3 |
| 81 | + | 95 | 285.4 | 286.4 |
| 82 | + | 95 | 382.4 | 383.4 |
| 83 | + | 95 | 422.3 | 423.3 |
| 84 | +++ | 95 | 420.4 | 421.4 |
| 85 | ++ | 95 | 345.3 | 346.3 |
| 86 | ++ | 98 | 341.4 | 342.4 |
| 87 | ++ | 98 | 349.4 | 350.4 |
| 88 | ++ | 95 | 301.4 | 302.4 |
| 89 | ++ | 95 | 379.3 | 380.3 |
| 90 | ++ | 95 | 379.3 | 380.3 |

"+" represents 10 μM > $EC_{50}$ > 3 μM
"++" represents 3 μM > $EC_{50}$ > 0.5 μM
"+++" represents $EC_{50}$ < 0.5 μM

Example 2

Preparation of N-(6-fluoro-3-phenylimidazo[1,2-a]pyridin-2-yl)-2-(4-fluoro-phenyl)acetamide (92)

Method 2

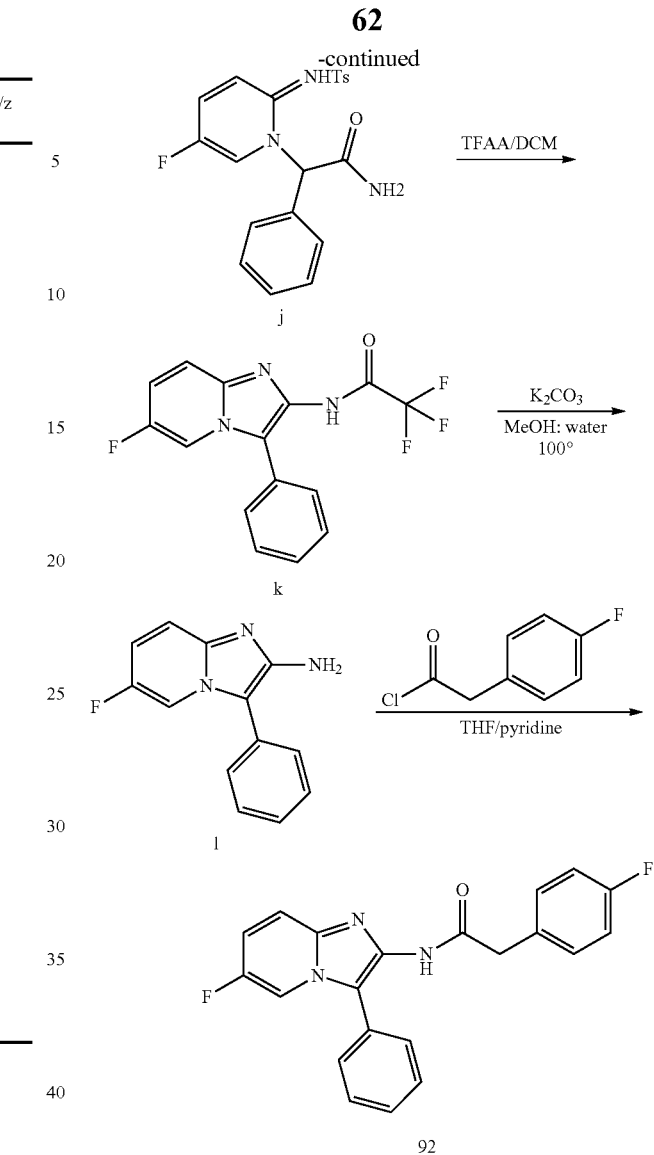

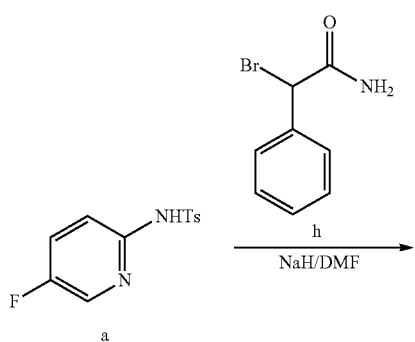

Synthesis of 2-Bromo-2-phenylacetamide (h)

Benzeneacetamide (3.0 g, 0.022 mol) was dissolved in dichloromethane (60 mL) and N-bromosuccinimide (4.0 g, 0.022 mol) was added. The reaction was stirred at room temperature under UV light for 24 hr. The mixture was poured into water and the layers were separated. The organic layer was washed with water (2×50 mL) then with brine (1×50 mL). The organic layer was dried (magnesium sulfate) then chromatographed on silica (40% ethyl acetate/hexanes) to give 2-Bromo-2-phenylacetamide, compound h Rf 0.37, 40% ethyl acetate/hexanes; MS m/z 216 (M+H).

Synthesis of 2-(5-fluoro-2-(tosylimino)pyridin-1(2H)-yl)-2-phenylacetamide (j)

Sodium hydride (0.040 g, 0.0017 mol) was suspended in N,N-dimethylformamide (15 mL) and was cooled at 0° C. N-(5-fluoropyridin-2-yl)-4-methylbenzenesulfonamide (compound a, 0.37 g, 0.0014 mol) was added and was stirred for 15 minutes. 2-Bromo-2-phenylacetamide h (0.3 g, 0.001 mol) was added then the reaction was warmed to room temperature and was stirred for 24 hours. The reaction was poured into water and extracted with ethyl acetate (3×50 mL) then dried then chromatographed on silica (50% ethyl acetate/hexanes) to give 2-(5-fluoro-2-(tosylimino)pyridin-1 (2H)-yl)-2-phenylacetamide (compound j) Rf 0.42, 50% ethyl acetate/hexanes; MS m/z 400 (M+H).

Synthesis of 2,2,2-trifluoro-N-(6-fluoro-3-phenylimidazo[1,2-a]pyridin-2-yl)acetamide (k)

2-(5-fluoro-2-(tosylimino)pyridin-1(2H)-yl)-2-phenylacetamide (compound j, 0.370 g, 0.00093 mol) was dissolved in dichloromethane (5.0 mL) and trifluoroacetic anhydride (2.0 mL, 0.014 mol) was added. The reaction was stirred at room for 2 h. Solvent was removed and the residue taken up in ethyl acetate then washed with saturated NaHCO$_3$ (3×50 mL). Solvent removed to provide clean 2,2,2-trifluoro-N-(6-fluoro-3-phenylimidazo[1,2-a]pyridin-2-yl)acetamide Rf 0.41, 70% ethyl acetate/hexanes; MS m/z 324 (M+H).

Synthesis of 6-fluoro-3-phenylimidazo[1,2-a]pyridin-2-amine (l)

2,2,2-trifluoro-N-(6-fluoro-3-phenylimidazo[1,2-a]pyridin-2-yl)acetamide (compound k, 0.190 g, 0.0006 mol) was dissolved in methanol (8.0 mL) and water (2 ml). To this was added potassium carbonate (0.2 g, 0.002 mol). The reaction was heated in the microwave at 100° C. for 45 min. The solvent concentrated and residue was partitioned between water (100 mL) and ethyl acetate (100 mL). The layers were separated and the organic layer was dried (magnesium sulfate) then chromatographed on silica (55:40:5, DCM:acetonitrile:MeOH) to give 6-fluoro-3-phenylimidazo[1,2-a]pyridin-2-amine Rf 0.40, (55:40:5, DCM:acetonitrle:MeOH); MS ink 228 (M+H).

Synthesis of N-(6-fluoro-3-phenylimidazo[1,2-a] pyridin-2-yl)-2-(4-fluorophenyl)acetamide (92)

6-fluoro-3-phenylimidazo[1,2-a]pyridin-2-amine (compound 1, 0.075 g, 0.00033 mol) was dissolved in tetrahydrofuran (5.0 mL) and pyridine (29 uL, 0.00036 mol) was added. Rxn cooled to 0° C. and 4-fluorophenylacetyl chloride (48 uL, 0.00036 mol) was added. The reaction was stirred at C for 30 minutes. The solvent was removed and the crude product was partioned between water (25 mL) and EtOAc (25 mL). The layers were separated and the organic layer was washed 3×20 mL with water. The organic layer was dried (magnesium sulfate) then chromatographed on silica (70% ethyl acetate/hexanes) to give N-(6-fluoro-3-phenylinaidazo[1,2-a]pyridin-2-yl)-2-(4-fluorophenyl)acetamide Rf 0.37, 70% ethyl acetate/hexanes; MS m/z 364 (M+H). SH-SY5Y_EC50 (μM): 0.7321.

The following compounds were prepared according to the procedures of Method 2. In one embodiment, 2-aminopyridazine was used as the starting material in preparing compounds 271, 272, 305, 306, 308, 309, 316, 339 and 346, which contain a imidazo[1,2-b]pyridazin moiety. In another embodiment, 2-aminopyrimidine was used as the starting material for preparing compounds 317-325 and 329-333, which contain a imidazo[1,2-a]pyrimidin moiety. The number next to each compound listed below corresponds to the compound number in Table 2.

Following is a List of the Compounds Prepared by Method 2:
2,2,2-trifluoro-N-(6-fluoro-3-phenylimidazo[1,2-a]pyridin-2-yl)acetamide 91
N-(6-fluoro-3-phenylimidazo[1,2-a]pyridin-2-yl)-2-(4-fluorophenyl)acetamide 92
N-(6-fluoro-3-phenylimidazo[1,2-a]pyridin-2-yl)-3,3-dimethylbutanamide 93
2-cyclopentyl-N-(6-fluoro-3-phenylimidazo[1,2-a]pyridin-2-yl)acetamide 94
3,3,3-trifluoro-N-(6-fluoro-3-phenylimidazo[1,2-a]pyridin-2-yl)propanamide 95
N-(6-fluoro-3-phenylimidazo[1,2-a]pyridin-2-yl)-2-phenylacetamide 96
4,4,4-trifluoro-N-(6-fluoro-3-phenylimidazo[1,2-a]pyridin-2-yl)butanamide 97
2-cyclopentyl-N-(3-phenyl-7-(trifluoromethyl)imidazo[1,2-a]pyridin-2-yl)acetamide 98
2-(4-fluorophenyl)-N-(3-phenyl-7-(trifluoromethyl)imidazo[1,2-a]pyridin-2-yl)acetamide 99
3,3-dimethyl-N-(3-phenyl-7-(trifluoromethyl)imidazo[1,2-a]pyridin-2-yl)butanamide 100
2-phenyl-N-(3-phenyl-7-(trifluoromethyl)imidazo[1,2-a]pyridin-2-yl)acetamide 101
N-(6-fluoro-3-(4-fluorophenyl)imidazo[1,2-a]pyridin-2-yl)-2-(4-fluorophenyl)acetamide 102
N-(6-fluoro-3-(4-fluorophenyl)imidazo[1,2-a]pyridin-2-yl)-3,3-dimethylbutanamide 103
3,3,3-trifluoro-N-(3-phenyl-7-(trifluoromethyl)imidazo[1,2-a]pyridin-2-yl)propanamide 104
4,4,4-trifluoro-N-(3-phenyl-7-(trifluoromethyl)imidazo[1,2-a]pyridin-2-yl)butanamide 105
N-(6-fluoro-3-(4-fluorophenyl)imidazo[1,2-a]pyridin-2-yl)-2-phenylacetamide 106
2-cyclopentyl-N-(6-fluoro-3-(4-fluorophenyl)imidazo[1,2-a]pyridin-2-yl)acetamide 107
4,4,4-trifluoro-N-(6-fluoro-3-(4-fluorophenyl)imidazo[1,2-a]pyridin-2-yl)butanamide 108.
N-(6-fluoro-3-(4-fluorophenyl)imidazo[1,2-a]pyridin-2-yl)-2-phenylpropanamide 109
2-phenyl-N-(3-phenyl-7-(trifluoromethyl)imidazo[1,2-a]pyridin-2-yl)propanamide 110
2-(4-fluorophenyl)-N-(3-(4-fluorophenyl)-7-(trifluoromethyl)imidazo[1,2-a]pyridin-2-yl)acetamide 111
N-(3-(4-fluorophenyl)-7-(trifluoromethyl)imidazo[1,2-a]pyridin-2-yl)-2-phenylacetamide 112
N-(3-(4-fluorophenyl)-7-(trifluoromethyl)imidazo[1,2-a]pyridin-2-yl)-3,3-dimethylbutanamide 113
N-(3-(4-fluorophenyl)-7-(trifluoromethyl)imidazo[1,2-a]pyridin-2-yl)-2-phenylpropanamide 114
N-(3-(2,4-difluorophenyl)-6-fluoroimidazo[1,2-a]pyridin-2-yl)-2-phenylacetamide 115
N-(3-(2,4-difluorophenyl)-6-fluoroimidazo[1,2-a]pyridin-2-yl)-3,3-dimethylbutanamide 116
N-(3-(2,4-difluorophenyl)-6-fluoroimidazo[1,2-a]pyridin-2-yl)-2-(4-fluorophenyl)acetamide 117
2-cyclopentyl-N-(3-(2,4-difluorophenyl)-6-fluoroimidazo[1,2-a]pyridin-2-yl)acetamide 118
N-(3-(4-fluorophenyl)-6-(trifluoromethyl)imidazo[1,2-a]pyridin-2-yl)-2-phenylacetamide 119
N-(3-(4-fluorophenyl)-6-(trifluoromethyl)imidazo[1,2-a]pyridin-2-yl)-3,3-dimethylbutanamide 120
2-(4-fluorophenyl)-N-(3-(4-fluorophenyl)-6-(trifluoromethyl)imidazo[1,2-a]pyridin-2-yl)acetamide 121
N-(3-(2,4-difluorophenyl)-7-(trifluoromethyl)imidazo[1,2-a]pyridin-2-yl)-2-(4-fluorophenyl)acetamide 122
N-(3-(2,4-difluorophenyl)-7-(trifluoromethyl)imidazo[1,2-a]pyridin-2-yl)-3,3-dimethylbutanamide 123
N-(3-(2,4-difluorophenyl)-7-(trifluoromethyl)imidazo[1,2-a]pyridin-2-yl)-2-phenyl acetamide 124

2-cyclopentyl-N-(3-(2,4-difluorophenyl)-7-(trifluoromethyl)imidazo[1,2-a]pyridin-2-yl)acetamide 125
N-(6-fluoro-3-(4-(trifluoromethyl)phenyl)imidazo[1,2-a]pyridin-2-yl)-2-(4-fluorophenyl)acetamide 126
N-(6-fluoro-3-(4-(trifluoromethyl)phenyl)imidazo[1,2-a]pyridin-2-yl)-2-phenylacetamide 127
N-(6-fluoro-3-(4-(trifluoromethyl)phenyl) imidazo[1,2-a]pyridin-2-yl)-3,3-dimethylbutanamide 128
2-cyclopropyl-N-(6-fluoro-3-(4-fluorophenyl)imidazo[1,2-a]pyridin-2-yl)acetamide 129
N-(6-chloro-3-(4-fluorophenyl)imidazo[1,2-a]pyridin-2-yl)-3,3-dimethylbutanamide
N-(6-chloro-3-(4-fluorophenyl)imidazo[1,2-a]pyridin-2-yl)-2-(4-fluorophenyl)acetamide 131
N-(6-fluoro-3-(4-fluorophenyl)imidazo[1,2-a]pyridin-2-yl)-2-(4-methoxyphenyl)acetamide 132
N-(6-fluoro-3-(4-fluorophenyl)imidazo[1,2-a]pyridin-2-yl)-3-methylbutanamide 133
N-(6-fluoro-3-(4-fluorophenyl)imidazo[1,2-a]pyridin-2-yl)-3-phenylpropanamide 134
N-(6-fluoro-3-(4-fluorophenyl)imidazo[1,2-a]pyridin-2-yl)-2-(4-(trifluoromethyl)phenyl)acetamide 135
2-(2,4-difluorophenyl)-N-(6-fluoro-3-(4-fluorophenyl)imidazo[1,2-a]pyridin-2-yl)acetamide 136
2-(4-cyanophenyl)-N-(6-fluoro-3-(4-fluorophenyl)imidazo[1,2-a]pyridin-2-yl)acetamide 137
2-(bicyclo[2.2.1]heptan-2-yl)-N-(6-fluoro-3-(4-fluorophenyl)imidazo[1,2-a]pyridin-2-yl)acetamide 138
N-(6-fluoro-3-(4-fluorophenyl)imidazo[1,2-a]pyridin-2-yl)-3,5,5-trimethylhexanamide 139
2-(2-chloro-4-fluorophenyl)-N-(6-fluoro-3-(4-fluorophenyl)imidazo[1,2-a]pyridin-2-yl)acetamide 140
2-(2-chloro-6-fluorophenyl)-N-(6-fluoro-3-(4-fluorophenyl)imidazo[1,2-a]pyridin-2-yl)acetamide 141
2-(3,4-dichlorophenyl)-N-(6-fluoro-3-(4-fluorophenyl)imidazo yl)acetamide 142
N-(6-fluoro-3-(4-fluorophenyl)imidazo[1,2-a]pyridin-2-yl)-2-p-tolylacetamide 143
4,4,4-trifluoro-N-(6-fluoro-3-(4-fluorophenyl)imidazo[1,2-a]pyridin-2-yl)-3-methylbutanamide 144
2-(4-chlorophenyl)-N-(6-fluoro-3-(4-fluorophenyl)imidazo[1,2-a]pyridin-2-yl)acetamide 145
benzyl 6-fluoro-3-(4-fluorophenyl)imidazo[1,2-a]pyridin-2-ylcarbamate 146
N-(6-fluoro-3-(4-fluorophenyl)imidazo[1,2-a]pyridin-2-yl)-3-methylpentanamide 147
N-(3-(3-chlorophenyl)-6-fluoroimidazo[1,2-a]pyridin-2-yl)-2-(4-fluorophenyl)acetamide 148
N-(3-(3-chlorophenyl)-6-fluoroimidazo[1,2-a]pyridin-2-yl)-3,3-dimethylbutanamide 149
N-(3-(4-chlorophenyl)-6-fluoroimidazo[1,2-a]pyridin-2-yl)-3,3-dimethylbutanamide 150
N-(6-fluoro-3-(4-fluorophenyl)imidazo[1,2-a]pyridin-2-yl) hex-5-ynamide 151
N-(6-bromo-3-(4-fluorophenyl)imidazo[1,2-a]pyridin-2-yl)-3,3-dimethyl butanamide 152
N-(6-fluoro-3(4-(trifluoromethoxy)phenyl)imidazo[1,2-a]pyridin-2-yl)-3,3-dimethylbutanamide 153
N-(6-fluoro-3-(4-(trifluoromethoxy)phenyl)imidazo[1,2-a]pyridin-2-yl)-2-(4-fluorophenyl)acetamide 154
N-(3-(3-chlorophenyl)-6-fluoroimidazo[1,2-a]pyridin-2-yl)-2-phenylacetamide 155
2-cyclopentyl-N-(6-fluoro-3-(4-(trifluoromethyl)phenyl) imidazo[1,2-a]pyridin-2-yl)acetamide 156
2-cyclohexyl-N-(6-fluoro-3-(4-(trifluoromethyl)phenyl)imidazo[1,2-a]pyridin-2-yl)acetamide 157
N-(3-(2-chlorophenyl)-6-fluoroimidazo[1,2-a]pyridin-2-yl)-3,3-dimethylbutanamide 158
N-(6-cyano-3-(4-fluorophenyl)imidazo[1,2-a]pyridin-2-yl)-3,3-dimethylbutanamide 159
N-(6-cyano-3-(4-fluorophenyl)imidazo[1,2-a]pyridin-2-yl)-2-phenylacetamide 160
benzyl 6-fluoro-3-(4-(trifluoromethyl)phenyl)imidazo[1,2-a]pyridin-2-ylcarbamate 161
N-(6-fluoro-3(4-fluorophenyl)imidazo[1,2-a]pyridin-2-yl)-2,3-dimethylbutanamide 162
N-(6-fluoro-3-(3-(trifluoromethyl)phenyl)imidazo[1,2-a]pyridin-2-yl)-3,3-dimethylbutanamide 163
N-(6-fluoro-3-(3-(trifluoromethyl)phenyl)imidazo[1,2-a]pyridin-2-yl)-2-(4-fluorophenyl)acetamide 164
N-(6-fluoro-3-(3-(trifluoromethyl)phenyl)imidazo[1,2-a]pyridin-2-yl)-2-phenylacetamide 165
N-(3-(4-fluorophenyl)-6-methylimidazo[1,2-a]pyridin-2-yl)-2-phenylacetamide 166
N-(3-(4-fluorophenyl)-6-methylimidazo[1,2-a]pyridin-2-yl)-3,3-dimethylbutanamide 167
N-(3-(4-fluorophenyl)-7-methylimidazo[1,2-a]pyridin-2-yl)-2-phenylacetamide 168
N-(3-(4-fluorophenyl)-7-methylimidazo[1,2-a]pyridin-2-yl)-3,3-dimethylbutanamide 169
2-cyclopentyl-N-(6-fluoro-3-(4-(trifluoromethoxy)phenyl) imidazo[1,2-a]pyridin-2-yl)acetamide 170
2-cyclopropyl-N-(6-fluoro-3-(4-(trifluoromethoxy)phenyl) imidazo[1,2-a]pyridin-2-yl)acetamide 171
3-cyclopropyl-N-(6-fluoro-3-(4-(trifluoromethoxy)phenyl) imidazo[1,2-a]pyridin-2-yl)propanamide 172
4,4,4-trifluoro-N-(6-fluoro-3-(4-(trifluoromethoxy)phenyl) imidazo[1,2-a]pyridin-2-yl)butanamide 173
5,5,5-trifluoro-N-(6-fluoro-3-(4-(trifluoromethoxy)phenyl) imidazo[1,2-a]pyridin-2-yl)pentanamide 174
N-(3-(4-(2-cyanopropan-2-yl)phenyl)-6-fluoroimidazo[1,2-a]pyridin-2-yl)-3,3-dimethylbutanamide 175
N-(3-(3-(2-cyanopropan-2-yl)phenyl)-6-fluoroimidazo[1,2-a]pyridin-2-yl)-3,3-dimethylbutanamide 176
N-(3-(4-cyanophenyl)-6-fluoroimidazo[1,2-a]pyridin-2-yl)-3,3-dimethylbutanamide 177
3,3-dimethyl-N-(3-(4-(trifluoromethoxy)phenyl)-6-(trifluoromethyl)imidazo[1,2-a]pyridin-2-yl)butanamide 178
N-(6-fluoro-3-(4-fluorophenyl)imidazo[1,2-a]pyridin-2-yl)-2-(1-methylcyclopentyl)acetamide 179
N-(6-fluoro-3-(4-(trifluoromethyl)phenyl)imidazo[1,2-a]pyridin-2-yl)-2-(1-methylcyclopentyl)acetamide 180
N-(6-fluoro-3-(4-(trifluoromethyl)phenyl)imidazo[1,2-a]pyridin-2-yl)-2-hydroxy-3,3-dimethylbutanamide 181
N-(6-fluoro-3-(3-(trifluoromethoxy)phenyl)imidazo[1,2-a]pyridin-2-yl)-3,3 dimethylbutanamide 182
N-(6-fluoro-3-(3-(trifluoromethoxy)phenyl) imidazo[1,2-a]pyridin-2-yl)-2-(4-fluorophenyl) acetamide 183
N-(6-fluoro-3-(4-(trifluoromethyl)phenyl)imidazo[1,2-a]pyridin-2-yl)-2,3-dimethylbutanamide 184
2-cyclobutyl-N-(6-fluoro-3-(4-(trifluoromethyl)phenyl) imidazo[1,2-a]pyridin-2-yl)acetamide 185
N-(3-(4-fluorophenyl)-6-methylimidazo[1,2-a]pyridin-2-yl)-2-(4-(trifluoromethyl)phenyl)acetamide 186
N-(3-(4-fluorophenyl)-7-methylimidazo[1,2-a]pyridin-2-yl)-2-(4-(trifluoromethyl)phenyl)acetamide 187
N-(6-fluoro-3-(4-(trifluoromethyl)phenyl)imidazo[1,2-a]pyridin-2-yl)-4,4-dimethylpentanamide 188
4-(6-fluoro-3-(4-(trifluoromethyl)phenyl)imidazo[1,2-a]pyridin-2-ylamino)-2,2-dimethyl-4-oxobutyl acetate 189
N-(6-fluoro-3-(4-(trifluoromethyl)phenyl)imidazo[1,2-a]pyridin-2-yl)-4-hydroxy-3,3-dimethylbutanamide 190

4-(6-fluoro-3-(4-(trifluoromethoxy)phenyl)imidazo[1,2-a]pyridin-2-ylamino)-2,2-dimethyl-4-oxobutyl acetate 191
N-(6-fluoro-3-(4-(trifluoromethoxy)phenyl)imidazo[1,2-a]pyridin-2-yl)-4-hydroxy-3,3-dimethylbutanamide 192
N-(6-fluoro-3-(4-(trifluoromethoxy)phenyl)imidazo[1,2-a]pyridin-2-yl)-2-(1-methylcyclopentyl)acetamide 193
2-cyclobutyl-N-(6-fluoro-3-(4-(trifluoromethoxy)phenyl)imidazo[1,2-a]pyridin-2-yl)acetamide 194
4,4,4-trifluoro-N-(6-fluoro-3-(4-(trifluoromethoxy)phenyl)imidazo[1,2-a]pyridin-2-yl)-3-methylbutanamide 195
N-(3-(3-(difluoromethyl)-4-fluorophenyl)-6-fluoroimidazo[1,2-a]pyridin-2-yl)-3,3-dimethylbutanamide 196
N-(3-(4-cyano-3-fluorophenyl)-6-fluoroimidazo[1,2-a]pyridin-2-yl)-3,3-dimethylbutanamide 197
N-(6-fluoro-3-(3-fluoro-5-(trifluoromethyl)phenyl) imidazo[1,2-a]pyridin-2-yl)-3,3-dimethylbutanamide 198
N-(6-fluoro-3-(3-fluoro-4-(trifluoromethyl)phenyl)imidazo[1,2-a]pyridin-2-yl)-3,3-dimethylbutanamide 199
N-(6-fluoro-3-(4-methoxy-3-(trifluoromethyl)phenyl)imidazo[1,2-a]pyridin-2-yl)-3,3-dimethylbutanamide 200
N-(6-fluoro-3-(3-fluoro-4-methylphenyl)imidazo[1,2-a]pyridin-2-yl)-3,3-dimethylbutanamide 201
2,2-difluoro-N-(6-fluoro-3-(4-(trifluoromethyl)phenyl)imidazo[1,2-a]pyridin-2-yl)-3,3-dimethylbutanamide 202
2-(4-fluorophenyl)-N-(3-(4-fluorophenyl)imidazo[1,2-a]pyridin-2-yl)acetamide 203
2-(4-fluorophenyl)-N-(3-(4-(trifluoromethyl)phenyl)imidazo[1,2-a]pyridin-2-yl)acetamide 204
2-(4-fluorophenyl)-N-(3-(4-(trifluoromethoxy)phenyl)imidazo[1,2-a]pyridin-2-yl)acetamide 205
2-tert-butoxy-N-(6-fluoro-3-(4-(trifluoromethyl)phenyl)imidazo[1,2-a]pyridin-2-yl)acetamide 206
N-(6-fluoro-3-(4-(trifluoromethoxy)phenyl)imidazo[1,2-a]pyridin-2-yl)-2-phenylacetamide 207
2-tert-butoxy-N-(6-fluoro-3-(4-(trifluoromethoxy)phenyl)imidazo[1,2-a]pyridin-2-yl)acetamide 208
N-(3-(3,4-difluorophenyl)-6-fluoroimidazo[1,2-a]pyridin-2-yl)-4,4,4-trifluoro-3-methylbutanamide 209
N-(3-(3,4-difluorophenyl)-6-fluoroimidazo[1,2-a]pyridin-2-yl)-2-(4-fluorophenyl)acetamide 210
N-(3-(3,4-difluorophenyl)-6-fluoroimidazo[1,2-a]pyridin-2-yl)-2-phenylacetamide 211
N-(3-(3,4-difluorophenyl)-6-fluoroimidazo[1,2-a]pyridin-2-yl)-3,3-dimethylbutanamide 212
1-(6-fluoro-3-(4-(trifluoromethyl)phenyl)imidazo[1,2-a]pyridin-2-yl)-3-(4-fluorophenethyl)urea 213
1-(6-fluoro-3-(4-(trifluoromethyl)phenyl)imidazo[1,2-a]pyridin-2-yl)-3-(4-fluorobenzyl)urea 214
1-tert-butyl-3-(6-fluoro-3-(4-(trifluoromethyl)phenyl)imidazo[1,2-a]pyridin-2-yl)urea 215
N-(6,7-dichloro-3-(4-(trifluoromethoxy)phenyl)imidazo[1,2-a]pyridin-2-yl)-3,3-dimethylbutanamide 216
N-(6,7-dichloro-3-(4-(trifluoromethoxy)phenyl)imidazo[1,2-a]pyridin-2-yl)-2-(4-fluorophenyl)acetamide 217
3-cyano-N-(6-fluoro-3-(4-(trifluoromethoxy)phenyl)imidazo[1,2-a]pyridin-2-yl)-3-methylbutanamide 218
N-(6,7-dichloro-3-(4-(trifluoromethoxy)phenyl)imidazo trifluoro-3-methylbutanamide 219
3-cyclopentyl-N-(6-fluoro-3-(4-(trifluoromethyl)phenyl)imidazo[1,2-a]pyridin-2-yl)propanamide 220
N-(3-(4-fluorophenyl)imidazo[1,2-a]pyridin-2-yl)-3,3-dimethylbutanamide 221
2-cyclopentyl-N-(3-(4-fluorophenyl)imidazo[1,2-a]pyridin-2-yl)acetamide 222
3,3-dimethyl-N-(3-(4-(trifluoromethyl)phenyl)imidazo[1,2-a]pyridin-2-yl)butanamide 223
2-cyclopentyl-N-(3-(4-(trifluoromethyl)phenyl)imidazo[1,2-a]pyridin-2-yl)acetamide 224
3,3-dimethyl-N-(3-(4-(trifluoromethoxy)phenyl)imidazo[1,2-a]pyridin-2-yl)butanamide 225
2-cyclopentyl-N-(3-(4-(trifluoromethoxy)phenyl)imidazo[1,2-a]pyridin-2-yl)acetamide 226
N-(3-(3,5-difluorophenyl)-6-fluoroimidazo[1,2-a]pyridin-2-yl)-3,3-dimethylbutanamide 227
N-(3-(3,5-difluorophenyl)-6-fluoroimidazo[1,2-a]pyridin-2-yl)-2-phenylacetamide 228
N-(3-(3,5-difluorophenyl)-6-fluoroimidazo[1,2-a]pyridin-2-yl)-2-(4-fluorophenyl)acetamide 229
N-(3-(3,5-difluorophenyl)-6-fluoroimidazo[1,2-a]pyridin-2-yl)-4,4,4-trifluoro-3-methylbutanamide 230
N-(6-fluoro-3-(4-(trifluoromethoxy)phenyl)imidazo[1,2-a]pyridin-2-yl)-2-phenoxyacetamide 231
N-(6-fluoro-3-(4-(trifluoromethoxy)phenyl)imidazo[1,2-a]pyridin-2-yl)-2-phenoxypropanamide 232
N-(6,7-dichloro-3-(4-(trifluoromethyl)phenyl)imidazo[1,2-a]pyridin-2-yl)-3,3-dimethylbutanamide 233
N-(6-fluoro-3-(4-(trifluoromethyl)phenyl)imidazo[1,2-a]pyridin-2-yl)-2,3,3-trimethylbutanamide 234
N-(6-fluoro-3-(4-(trifluoromethoxy)phenyl)imidazo[1,2-a]pyridin-2-yl)-2,3,3-trimethylbutanamide 235
N-(6,7-dichloro-3-(4-(trifluoromethyl)phenyl)imidazo[1,2-a]pyridin-2-yl)-2-(4-fluorophenyl)acetamide 236
2-(benzyloxy)-N-(6-fluoro-3-(4-(trifluoromethoxy)phenyl)imidazo[1,2-a]pyridin-2-yl)acetamide 237
2-(4-chlorophenyl)-N-(6-fluoro-3-(4-(trifluoromethoxy)phenyl)imidazo[1,2-a]pyridin-2-yl)acetamide 238
2-(3-chlorophenyl)-N-(6-fluoro-3-(4-(trifluoromethoxy)phenyl)imidazo yl)acetamide 239
N-(6-fluoro-3-(4-(trifluoromethoxy)phenyl)imidazo[1,2-a]pyridin-2-yl)-2-(3-fluorophenyl)acetamide 240
2-(3,4-difluorophenyl)-N-(6-fluoro-3-(4-(trifluoromethoxy)phenyl)imidazo[1,2-a]pyridin-2-yl)acetamide 241
2-(3,5-difluorophenyl)-N-(6-fluoro-3-(4-(trifluoromethoxy)phenyl)imidazo[1,2-a]pyridin-2-yl)acetamide 242
(R)—N-(6-fluoro-3-(4-(trifluoromethoxy)phenyl)imidazo[1,2-a]pyridin-2-yl)tetrahydrofuran-2-carboxamide 243
(S)—N-(6-fluoro-3-(4-(trifluoromethoxy)phenyl)imidazo[1,2-a]pyridin-2-yl)tetrahydrofuran-2-carboxamide 244
N-(7-methoxy-3-(4-(trifluoromethyl)phenyl)imidazo[1,2-a]pyridin-2-yl)-3,3-dimethylbutanamide 245
N-(7-methoxy-3-(4-(trifluoromethyl)phenyl)imidazo[1,2-a]pyridin-2-yl)-2-phenylacetamide 246
2-(2,4-dichlorophenoxy)-N-(6-fluoro-3-(4-(trifluoromethoxy)phenyl)imidazo[1,2-a]pyridin-2-yl)acetamide 247
N-(6-fluoro-3-(4-(trifluoromethoxy)phenyl)imidazo[1,2-a]pyridin-2-yl)tetrahydrofuran-3-carboxamide 248
N-(6-fluoro-3-(4-(trifluoromethoxy)phenyl)imidazo[1,2-a]pyridin-2-yl)-2,3-dimethylbutanamide 249
N-(6-fluoro-3-(4-(trifluoromethoxy)phenyl)imidazo[1,2-a]pyridin-2-yl)-3-(4-fluorophenoxy)propanamide 250
N-(6-fluoro-3-(4-(trifluoromethoxy)phenyl)imidazo[1,2-a]pyridin-2-yl)-2-(tetrahydro-2H-pyran-4-yl)acetamide 251
3,3,3-trifluoro-N-(6-fluoro-3-(4-(trifluoromethoxy)phenyl)imidazo[1,2-a]pyridin-2-yl)propanamide 252
(R)—N-(6-fluoro-3-(4-(trifluoromethoxy)phenyl)imidazo[1,2-a]pyridin-2-yl)-2-methoxy-2-phenyl acetamide 253
(S)—N-(6-fluoro-3-(4-(trifluoromethoxy)phenyl)imidazo[1,2-a]pyridin-2-yl)-2-methoxy-2-phenyl acetamide 254
N-(6-fluoro-3-(4-fluoro-3-methylphenyl)imidazo[1,2-a]pyridin-2-yl)-3,3-dimethylbutanamide 255
N-(3-(2,4-difluoro-3-methylphenyl)-6-fluoroimidazo[1,2-a]pyridin-2-yl)-3,3-dimethylbutanamide 256

N-(3-(4-chloro-3-methylphenyl)-6-fluoroimidazo[1,2-a]pyridin-2-yl)-3,3-dimethylbutanamide 257
N-(3-(3-chloro-4-methylphenyl)-6-fluoroimidazo[1,2-a]pyridin-2-yl)-3,3-dimethylbutanamide 258
N-(6-cyano-3-(4-(trifluoromethyl)phenyl)imidazo[1,2-a]pyridin-2-yl)-3,3-dimethylbutanamide 259
N-(6-cyano-3-(4-(trifluoromethyl)phenyl)imidazo[1,2-a]pyridin-2-yl)-2-(4-fluorophenyl)acetamide 260
3-tert-butoxy-N-(6-fluoro-3-(4-(trifluoromethoxy)phenyl)imidazo yl)propanamide 261
N-(6,8-difluoro-3-(4-(trifluoromethoxy)phenyl)imidazo[1,2-a]pyridin-2-yl)-3,3-dimethylbutanamide 262
3,3,3-trifluoro-N-(6-fluoro-3-(3-(trifluoromethoxy)phenyl)imidazo[1,2-a]pyridin-2-yl)propanamide 263
2-cyclopentyl-N-(6-fluoro-3-(3-(trifluoromethoxy)phenyl)imidazo[1,2-a]pyridin-2-yl)acetamide 264
2-cyclopropyl-N-(6-fluoro-3-(3-(trifluoromethoxy)phenyl)imidazo[1,2-a]pyridin-2-yl)acetamide 265
2-cyclobutyl-N-(6-fluoro-3-(3-(trifluoromethoxy)phenyl)imidazo[1,2-a]pyridin-2-yl)acetamide 266
3,3,3-trifluoro-N-(6-fluoro-3-(3-(trifluoromethyl)phenyl)imidazo[1,2-a]pyridin-2-yl)propanamide 267
2-cyclopentyl-N-(6-fluoro-3-(3-(trifluoromethyl)phenyl)imidazo[1,2-a]pyridin-2-yl)acetamide 268
2-cyclopropyl-N-(6-fluoro-3-(3-(trifluoromethyl)phenyl)imidazo[1,2-a]pyridin-2-yl)acetamide 269
2-cyclobutyl-N-(6-fluoro-3-(3-(trifluoromethyl)phenyl)imidazo[1,2-a]pyridin-2-yl)acetamide 270
N-(6-chloro-3-(4-(trifluoromethyl)phenyl)imidazo[1,2-b]pyridazin-2-yl)-3,3-dimethylbutanamide 271
N-(6-chloro-3-(4-(trifluoromethyl)phenyl)imidazo[1,2-b]pyridazin-2-yl)-2-(4-fluorophenyl)acetamide 272
N-(6-fluoro-3-p-tolylimidazo[1,2-a]pyridin-2-yl)-3,3-dimethylbutanamide 273
3-cyclopropyl-N-(6-fluoro-3-(3-(trifluoromethoxy)phenyl)imidazo[1,2-a]pyridin-2-yl)propanamide 274
4,4,4-trifluoro-N-(6-fluoro-3-(3-(trifluoromethoxy)phenyl)imidazo[1,2-a]pyridin-2-yl)butanamide 275
4,4,4-trifluoro-N-(6-fluoro-3-(3-(trifluoromethoxy)phenyl)imidazo[1,2-a]pyridin-2-yl)-3-methylbutanamide 276
3-tert-butoxy-N-(6-fluoro-3-(3-(trifluoromethoxy)phenyl)imidazo[1,2-a]pyridin-2-yl)propanamide 277
N-(6-fluoro-3-(3-(trifluoromethoxy)phenyl)imidazo[1,2-a]pyridin-2-yl)-2,3-dimethylbutanamide 278
N-(6-fluoro-3-(3-(trifluoromethoxy)phenyl)imidazo[1,2-a]pyridin-2-yl)-4,4-dimethylpentanamide 279
3-cyclopropyl-N-(6-fluoro-3-(3-(trifluoromethyl)phenyl)imidazo[1,2-a]pyridin-2-yl)propanamide 280
4,4,4-trifluoro-N-(6-fluoro-3-(3-(trifluoromethyl)phenyl)imidazo[1,2-a]pyridin-2-yl)butanamide 281
4,4,4-trifluoro-N-(6-fluoro-3-(3-(trifluoromethyl)phenyl)imidazo[1,2-a]pyridin-2-yl)-3-methylbutanamide 282
N-(6-fluoro-3-(3-(trifluoromethyl)phenyl)imidazo[1,2-a]pyridin-2-yl)-4,4-dimethylpentanamide 283
N-(3-(3-chlorophenyl)-6-fluoroimidazo[1,2-a]pyridin-2-yl)-3,3,3-trifluoropropanamide 284
N-(3-(3-chlorophenyl)-6-fluoroimidazo[1,2-a]pyridin-2-yl)-4,4,4-trifluorobutanamide 285
N-(3-(3-chlorophenyl)-6-fluoroimidazo[1,2-a]pyridin-2-yl)-2-(1-methylcyclopentyl)acetamide 286
3-tert-butoxy-N-(6-fluoro-3-(3-(trifluoromethyl)phenyl)imidazo[1,2-a]pyridin-2-yl)propanamide 287
N-(6-fluoro-3-(3-(trifluoromethyl)phenyl)imidazo[1,2-a]pyridin-2-yl)-2,3-dimethylbutanamide 288
N-(6-fluoro-3-(3-(trifluoromethyl)phenyl)imidazo[1,2-a]pyridin-2-yl)cyclopentanecarboxamide 289
N-(6-fluoro-3-(4-(trifluoromethoxy)phenyl)imidazo[1,2-a]pyridin-2-yl)cyclopentanecarboxamide 290
N-(6-fluoro-3-(4-(trifluoromethoxy)phenyl)imidazo pyridin-2-yl)cycloheptanecarboxamide 291
N-(6-fluoro-3-(4-(trifluoromethoxy)phenyl)imidazo[1,2-a]pyridin-2-yl)-2,3-dihydro-1H-indene-2-carboxamide 292
N-(6-fluoro-3-(4-(trifluoromethoxy)phenyl)imidazo yl)cycloheptanecarboxamide 293
N-(6-fluoro-3-(4-(trifluoromethyl)phenyl)imidazo yl)cycloheptanecarboxamide 294
N-(6-fluoro-3-(3-fluoro-4-(trifluoromethoxy)phenyl)imidazo[1,2-a]pyridin-2-yl)-2-phenylacetamide 295
N-(6-fluoro-3-(3-fluoro-4-(trifluoromethoxy)phenyl)imidazo[1,2-a]pyridin-2-yl)-2-(4-fluorophenyl)acetamide 296
N-(6-fluoro-3-(3-fluoro-4-(trifluoromethoxy)phenyl)imidazo[1,2-a]pyridin-2-yl)-2-(4-(trifluoromethyl)phenyl)acetamide 297
2-(3-chlorophenyl)-N-(6-fluoro-3-(3-fluoro-4-(trifluoromethoxy)phenyl)imidazo[1,2-a]pyridin-2-yl)acetamide 298
N-(3-(3-chlorophenyl)-6-fluoroimidazo[1,2-a]pyridin-2-yl)-2-(4-(trifluoromethyl)phenyl)acetamide 299
2-(3-chlorophenyl)-N-(3-(3-chlorophenyl)-6-fluoroimidazo[1,2-a]pyridin-2-yl)acetamide 300
2-(4-chlorophenyl)-N-(3-(3-chlorophenyl)-6-fluoroimidazo[1,2-a]pyridin-2-yl)acetamide 301
N-(3-(3-chlorophenyl)-6-fluoroimidazo[1,2-a]pyridin-2-yl)-2-cyclopentylacetamide 302
4,4,4-trifluoro-N-(6-fluoro-3-(3-fluoro-4-(trifluoromethoxy)phenyl)imidazo[1,2-a]pyridin-2-yl)butanamide 303
N-(6-fluoro-3-(3-fluoro-4-(trifluoromethoxy)phenyl)imidazo[1,2-a]pyridin-2-yl)-2-(1-methylcyclopentyl)acetamide 304
3,3-dimethyl-N-(6-methyl-3-(3-(trifluoromethoxy)phenyl)imidazo[1,2-b]pyridazin-2-yl)butanamide 305
2-(4-fluorophenyl)-N-(6-methyl-3-(3-(trifluoromethoxy)phenyl)imidazo[1,2-b]pyridazin-2-yl)acetamide 306
3,3,3-trifluoro-N-(7-methoxy-3-(4-(trifluoromethyl)phenyl)imidazo[1,2-a]pyridin-2-yl)propanamide 307
3,3-dimethyl-N-(6-methyl-3-(3-(trifluoromethyl)phenyl)imidazo[1,2-b]pyridazin-2-yl)butan amide 308
2-(4-fluorophenyl)-N-(6-methyl-3-(3-(trifluoromethyl)phenyl)imidazo[1,2-b]pyridazin-2-yl)acetamide 309
2-(4-chlorophenyl)-N-(6-fluoro-3-(3-fluoro-4-(trifluoromethoxy)phenyl)imidazo[1,2-a]pyridin-2-yl)acetamide 310
2-cyclopentyl-N-(6-fluoro-3-(3-fluoro-4-(trifluoromethoxy)phenyl)imidazo[1,2-a]pyridin-2-yl)acetamide 311
N-(6-fluoro-3-(3-fluoro-4-(trifluoromethoxy)phenyl)imidazo[1,2-a]pyridin-2-yl)-2,3-dimethylbutanamide 312
4,4,4-trifluoro-N-(6-fluoro-3-(3-fluoro-4-(trifluoromethoxy)phenyl)imidazo[1,2-a]pyridin-2-yl)-3-methylbutanamide 313
N-(3-(3-chlorophenyl)-6-fluoroimidazo[1,2-a]pyridin-2-yl)-2,3-dimethylbutanamide 314
N-(3-(3-chlorophenyl)-6-fluoroimidazo[1,2-a]pyridin-2-yl)-4,4,4-trifluoro-3-methylbutanamide 315
4,4,4-trifluoro-3-methyl-N-(6-methyl-3-(3-(trifluoromethyl)phenyl)imidazo[1,2-b]pyridazin-2-yl)butanamide 316
N-(6-chloro-3-(4-(trifluoromethyl)phenyl)imidazo[1,2-a]pyrimidin-2-yl)-2-(4-fluorophenyl)acetamide 317
N-(6-chloro-3-(4-(trifluoromethyl)phenyl)imidazo[1,2-a]pyrimidin-2-yl)-4,4,4-trifluoro-3-methylbutanamide 318

N-(6-chloro-3-(3-chlorophenyl)imidazo[1,2-a]pyrimidin-2-yl)-3,3-dimethylbutanamide 319
N-(6-chloro-3-(3-chlorophenyl)imidazo[1,2-a]pyrimidin-2-yl)-2-(4-fluorophenyl) acetamide 320
N-(6-chloro-3-(3-chlorophenyl)imidazo[1,2-a]pyrimidin-2-yl)-4,4,4-trifluoro-3-methylbutanamide 321
N-(6-chloro-3-(4-(trifluoromethyl)phenyl)imidazo[1,2-a]pyrimidin-2-yl)-3,3-dimethylbutanamide 322
3,3-dimethyl-N-(3-(3-(trifluoromethoxy)phenyl)imidazo[1,2-a]pyrimidin-2-yl)butanamide 323
2-(4-fluorophenyl)-N-(3-(3-(trifluoromethoxy)phenyl)imidazo[1,2-a]pyrimidin-2-yl)acetamide 324
4,4,4-trifluoro-3-methyl-N-(3-(3-(trifluoromethoxy)phenyl)imidazo[1,2-a]pyrimidin-2-yl)butanamide 325
4,4-difluoro-N-(6-fluoro-3-(4-(trifluoromethoxy)phenyl)imidazo[1,2-a]pyridin-2-yl)cyclohexanecarboxamide 326
4,4-difluoro-N-(6-fluoro-3-(trifluoromethoxy)phenyl)imidazo[1,2-a]pyridin-2-yl)cyclohexanecarboxamide 327
4,4-difluoro-N-(6-fluoro-3-(trifluoromethyl)phenyl)imidazo[1,2-a]pyridin-2-yl)cyclohexanecarboxamide 328
N-(3-(3-chlorophenyl)imidazo[1,2-a]pyrimidin-2-yl)-3,3-dimethylbutanamide 329
N-(3-(3-chlorophenyl)imidazo[1,2-a]pyrimidin-2-yl)-2-(4-fluorophenyl)acetamide 330
N-(3-(3-chlorophenyl)imidazo[1,2-a]pyrimidin-2-yl)-4,4,4-trifluoro-3-methylbutanamide 331
N-(6-fluoro-3-(3-(trifluoromethyl)phenyl)imidazo[1,2-a]pyrimidin-2-yl)-3,3-dimethylbutanamide 332
N-(6-fluoro-3-(3-(trifluoromethoxy)phenyl)imidazo[1,2-a]pyrimidin-2-yl)-3,3-dimethylbutanamide 333
N-(6-fluoro-3-fluoro-4-(trifluoromethoxy)phenyl)imidazo[1,2-a]pyridin-2-yl)cyclobutanecarboxamide 334
N-(3-(3-chlorophenyl)-6-fluoroimidazo[1,2-a]pyridin-2-yl)cyclobutanecarboxamide 335
3,3-dimethyl-N-(3-(3-(trifluoromethyl)phenyl)imidazo[1,2-a]pyridin-2-yl)butanamide 336
4,4,4-trifluoro-3-methyl-N-(3-(3-(trifluoromethyl)phenyl)imidazo[1,2-a]pyridin-2-yl)butanamide 337
2-(4-fluorophenyl)-N-(3-(3-(trifluoromethyl)phenyl)imidazo[1,2-a]pyridin-2-yl)acetamide 338
N-(6-methoxy-3-(3-(trifluoromethyl)phenyl)imidazo[1,2-b]pyridazin-2-yl)-3,3-dimethylbutanamide 339
(S)-1-(6-fluoro-3-(4-(trifluoromethyl)phenyl)imidazo[1,2-a]pyridin-2-ylamino)-3,3-dimethyl-1-oxobutan-2-yl acetate 340
(S)—N-(6-fluoro-3-(4-(trifluoromethyl)phenyl)imidazo[1,2-a]pyridin-2-yl)-2-hydroxy-3,3-dimethylbutanamide 341
3,3-dimethyl-N-(3-(3-(trifluoromethoxy)phenyl)imidazo[1,2-a]pyridin-2-yl)butanamide 342
4,4,4-trifluoro-3-methyl-N-(3-(3-(trifluoromethoxy)phenyl)imidazo[1,2-a]pyridin-2-yl)butanamide 343
2-(4-fluorophenyl)-N-(3-(3-(trifluoromethoxy)phenyl)imidazo[1,2-a]pyridin-2-yl)acetamide 344
4,4-difluoro-N-(6-fluoro-3-(4-(trifluoromethyl)phenyl)imidazo[1,2-a]pyridin-2-yl)piperidine-1-carboxamide 345
N-(6-methoxy-3-(3-(trifluoromethoxy)phenyl)imidazo[1,2-b]pyridazin-2-yl)-3,3-dimethylbutanamide 346

Table 2 sets forth potencies, purity, calculated molecular weights and measured molecular weights of representative compounds of the invention in the SH-SY5Y native cell line in a FLIPR assay, for a selection of compounds. The compound numbers in Table 2 correspond to the respective compound numbers listed above in Example 2.

TABLE 2

| Compound No. | SH-SY5Y EC50, μM | Purity (%) | Molecular Weight | Observed m/z (M + H) |
|---|---|---|---|---|
| 91 | + | 98 | 323.2 | 324.2 |
| 92 | ++ | 98 | 363.4 | 364.4 |
| 93 | ++ | 98 | 325.4 | 326.4 |
| 94 | +++ | 98 | 337.4 | 338.4 |
| 95 | + | 98 | 337.3 | 338.3 |
| 96 | ++ | 98 | 345.4 | 346.4 |
| 97 | ++ | 98 | 351.3 | 352.3 |
| 98 | ++ | 98 | 387.4 | 388.4 |
| 99 | +++ | 98 | 413.4 | 414.4 |
| 100 | ++ | 98 | 375.4 | 376.4 |
| 101 | ++ | 98 | 395.4 | 396.4 |
| 102 | +++ | 98 | 381.4 | 382.4 |
| 103 | +++ | 98 | 343.4 | 344.4 |
| 104 | + | 98 | 387.3 | 388.3 |
| 105 | + | 98 | 401.3 | 402.3 |
| 106 | ++ | 95 | 363.4 | 364.4 |
| 107 | +++ | 99 | 355.4 | 356.4 |
| 108 | ++ | 99 | 369.3 | 370.3 |
| 109 | ++ | 99 | 377.4 | 378.4 |
| 110 | ++ | 98 | 409.4 | 410.4 |
| 111 | ++ | 98 | 431.4 | 432.4 |
| 112 | ++ | 95 | 413.4 | 414.4 |
| 113 | ++ | 95 | 393.4 | 394.4 |
| 114 | ++ | 97 | 427.4 | 428.4 |
| 115 | ++ | 98 | 381.4 | 382.4 |
| 116 | ++ | 98 | 361.4 | 362.4 |
| 117 | ++ | 98 | 399.3 | 400.3 |
| 118 | ++ | 98 | 373.4 | 374.4 |
| 119 | +++ | 98 | 413.4 | 414.4 |
| 120 | +++ | 98 | 393.4 | 394.4 |
| 121 | +++ | 98 | 431.4 | 432.4 |
| 122 | ++ | 98 | 449.3 | 450.3 |
| 123 | ++ | 98 | 411.4 | 412.4 |
| 124 | ++ | 98 | 431.4 | 432.4 |
| 125 | ++ | 98 | 423.4 | 424.4 |
| 126 | ++ | 98 | 431.4 | 432.4 |
| 127 | +++ | 98 | 413.4 | 414.4 |
| 128 | +++ | 98 | 393.4 | 394.4 |
| 129 | + | 98 | 327.3 | 328.3 |
| 130 | +++ | 98 | 359.8 | 360.8 |
| 131 | +++ | 98 | 397.8 | 398.8 |
| 132 | ++ | 96 | 393.4 | 394.4 |
| 133 | ++ | 95 | 329.3 | 330.3 |
| 134 | ++ | 96 | 377.4 | 378.4 |
| 135 | ++ | 98 | 431.4 | 432.4 |
| 136 | ++ | 98 | 399.3 | 400.3 |
| 137 | ++ | 98 | 388.4 | 389.4 |
| 138 | +++ | 98 | 381.4 | 382.4 |
| 139 | +++ | 98 | 385.5 | 386.5 |
| 140 | + | 98 | 415.8 | 416.8 |
| 141 | + | 98 | 415.8 | 416.8 |
| 142 | +++ | 98 | 432.3 | 433.3 |
| 143 | +++ | 98 | 377.4 | 378.4 |
| 144 | ++ | 98 | 383.3 | 384.3 |
| 145 | ++ | 98 | 397.8 | 398.8 |
| 146 | +++ | 97 | 379.4 | 380.4 |
| 147 | ++ | 95 | 343.4 | 344.4 |
| 148 | +++ | 99 | 397.8 | 398.8 |
| 149 | +++ | 99 | 359.8 | 360.8 |
| 150 | +++ | 99 | 359.8 | 360.8 |
| 151 | ++ | 98 | 339.3 | 340.3 |
| 152 | +++ | 98 | 404.3 | 405.3 |
| 153 | +++ | 99 | 409.4 | 410.4 |
| 154 | +++ | 99 | 447.4 | 448.4 |
| 155 | +++ | 99 | 379.8 | 380.8 |
| 156 | +++ | 98 | 405.4 | 406.4 |
| 157 | +++ | 98 | 419.4 | 420.4 |
| 158 | ++ | 99 | 359.8 | 360.8 |
| 159 | ++ | 98 | 350.4 | 351.4 |
| 160 | ++ | 98 | 370.4 | 371.4 |
| 161 | + | 98 | 429.4 | 430.4 |
| 162 | ++ | 98 | 343.4 | 344.4 |
| 163 | +++ | 99 | 393.4 | 394.4 |
| 164 | +++ | 99 | 431.4 | 432.4 |
| 165 | +++ | 98 | 413.4 | 414.4 |
| 166 | +++ | 98 | 359.4 | 360.4 |
| 167 | +++ | 98 | 339.4 | 340.4 |

TABLE 2-continued

| Compound No. | SH-SY5Y EC50, μM | Purity (%) | Molecular Weight | Observed m/z (M + H) |
|---|---|---|---|---|
| 168 | +++ | 98 | 359.4 | 360.4 |
| 169 | +++ | 98 | 339.4 | 340.4 |
| 170 | +++ | 95 | 421.4 | 422.4 |
| 171 | ++ | 99 | 393.3 | 394.3 |
| 172 | ++ | 99 | 407.4 | 408.4 |
| 173 | ++ | 99 | 435.3 | 436.3 |
| 174 | +++ | 99 | 449.3 | 450.3 |
| 175 | ++ | 98 | 392.5 | 393.5 |
| 176 | ++ | 98 | 392.5 | 393.5 |
| 177 | ++ | 99 | 350.4 | 351.4 |
| 178 | +++ | 98 | 459.4 | 460.4 |
| 179 | +++ | 98 | 369.4 | 370.4 |
| 180 | +++ | 98 | 419.4 | 420.4 |
| 181 | ++ | 95 | 409.4 | 410.4 |
| 182 | +++ | 99 | 409.4 | 410.4 |
| 183 | +++ | 99 | 447.4 | 448.4 |
| 184 | ++ | 98 | 393.4 | 394.4 |
| 185 | +++ | 98 | 391.4 | 392.4 |
| 186 | +++ | 98 | 427.4 | 428.4 |
| 187 | +++ | 98 | 427.4 | 428.4 |
| 188 | +++ | 95 | 407.4 | 408.4 |
| 189 | + | 95 | 451.4 | 452.4 |
| 190 | + | 95 | 409.4 | 410.4 |
| 191 | + | 95 | 467.4 | 468.4 |
| 192 | ++ | 95 | 425.4 | 426.4 |
| 193 | +++ | 98 | 435.4 | 436.4 |
| 194 | +++ | 98 | 407.4 | 408.4 |
| 195 | +++ | 99 | 449.3 | 450.3 |
| 196 | +++ | 96 | 393.4 | 394.4 |
| 197 | ++ | 97 | 368.4 | 369.4 |
| 198 | +++ | 99 | 411.4 | 412.4 |
| 199 | +++ | 99 | 411.4 | 412.4 |
| 200 | +++ | 98 | 423.4 | 424.4 |
| 201 | +++ | 97 | 357.4 | 358.4 |
| 202 | +++ | 95 | 429.4 | 430.4 |
| 203 | ++ | 98 | 363.4 | 364.4 |
| 204 | +++ | 98 | 413.4 | 414.4 |
| 205 | +++ | 97 | 429.4 | 430.4 |
| 206 | + | 98 | 409.4 | 410.4 |
| 207 | +++ | 99 | 429.4 | 430.4 |
| 208 | + | 99 | 425.4 | 426.4 |
| 209 | +++ | 99 | 401.3 | 402.3 |
| 210 | +++ | 99 | 399.3 | 400.3 |
| 211 | +++ | 99 | 381.4 | 382.4 |
| 212 | +++ | 99 | 361.4 | 362.4 |
| 213 | + | 95 | 460.4 | 461.4 |
| 214 | ++ | 94 | 446.4 | 447.4 |
| 215 | ++ | 95 | 394.4 | 395.4 |
| 216 | +++ | 98 | 460.3 | 461.3 |
| 217 | ++ | 98 | 498.3 | 499.3 |
| 218 | ++ | 98 | 420.4 | 421.4 |
| 219 | ++ | 95 | 500.2 | 501.2 |
| 220 | +++ | 98 | 419.4 | 420.4 |
| 221 | ++ | 99 | 325.4 | 326.4 |
| 222 | ++ | 99 | 337.4 | 338.4 |
| 223 | +++ | 99 | 375.4 | 376.4 |
| 224 | +++ | 99 | 387.4 | 388.4 |
| 225 | +++ | 99 | 391.4 | 392.4 |
| 226 | +++ | 99 | 403.4 | 404.4 |
| 227 | +++ | 99 | 361.4 | 362.4 |
| 228 | +++ | 99 | 381.4 | 382.4 |
| 229 | +++ | 99 | 399.3 | 400.3 |
| 230 | ++ | 99 | 401.3 | 402.3 |
| 231 | + | 99 | 445.4 | 446.4 |
| 232 | + | 99 | 459.4 | 460.4 |
| 233 | +++ | 95 | 444.3 | 445.3 |
| 234 | +++ | 98 | 407.4 | 408.4 |
| 235 | +++ | 98 | 423.4 | 424.4 |
| 236 | +++ | 98 | 482.3 | 483.3 |
| 237 | + | 99 | 459.4 | 460.4 |
| 238 | +++ | 99 | 463.8 | 464.8 |
| 239 | +++ | 99 | 463.8 | 464.8 |
| 240 | +++ | 98 | 447.4 | 448.4 |
| 241 | +++ | 99 | 465.3 | 466.3 |
| 242 | +++ | 99 | 465.3 | 466.3 |
| 243 | + | 99 | 409.3 | 410.3 |
| 244 | + | 99 | 409.3 | 410.3 |
| 245 | ++ | 98 | 405.4 | 406.4 |
| 246 | ++ | 95 | 425.4 | 426.4 |
| 247 | + | 99 | 514.3 | 515.3 |
| 248 | + | 99 | 409.3 | 410.3 |
| 249 | +++ | 99 | 409.4 | 410.4 |
| 250 | ++ | 99 | 477.4 | 478.4 |
| 251 | ++ | 99 | 437.4 | 438.4 |
| 252 | +++ | 99 | 421.3 | 422.3 |
| 253 | + | 99 | 459.4 | 460.4 |
| 254 | + | 99 | 459.4 | 460.4 |
| 255 | +++ | 96 | 357.4 | 358.4 |
| 256 | ++ | 98 | 375.4 | 376.4 |
| 257 | +++ | 97 | 373.9 | 374.9 |
| 258 | +++ | 97 | 373.9 | 374.9 |
| 259 | +++ | 98 | 400.4 | 401.4 |
| 260 | +++ | 98 | 438.4 | 439.4 |
| 261 | +++ | 99 | 439.4 | 440.4 |
| 262 | +++ | 97 | 427.4 | 428.4 |
| 263 | ++ | 99 | 421.3 | 422.3 |
| 264 | +++ | 99 | 421.4 | 422.4 |
| 265 | ++ | 99 | 393.3 | 394.3 |
| 266 | +++ | 99 | 407.4 | 408.4 |
| 267 | ++ | 99 | 405.3 | 406.3 |
| 268 | +++ | 99 | 405.4 | 406.4 |
| 269 | ++ | 99 | 377.3 | 378.3 |
| 270 | +++ | 99 | 391.4 | 392.4 |
| 271 | +++ | 98 | 410.8 | 411.8 |
| 272 | ++ | 98 | 448.8 | 449.8 |
| 273 | ++ | 97 | 339.4 | 340.4 |
| 274 | +++ | 99 | 407.4 | 408.4 |
| 275 | ++ | 99 | 435.3 | 436.3 |
| 276 | +++ | 99 | 449.3 | 450.3 |
| 277 | +++ | 98 | 439.4 | 440.4 |
| 278 | +++ | 99 | 409.4 | 410.4 |
| 279 | +++ | 99 | 423.4 | 424.4 |
| 280 | ++ | 99 | 391.4 | 392.4 |
| 281 | ++ | 99 | 419.3 | 420.3 |
| 282 | +++ | 99 | 433.3 | 434.3 |
| 283 | +++ | 99 | 407.4 | 408.4 |
| 284 | ++ | 98 | 371.7 | 372.7 |
| 285 | ++ | 98 | 385.7 | 386.7 |
| 286 | +++ | 98 | 385.9 | 386.9 |
| 287 | ++ | 98 | 423.4 | 424.4 |
| 288 | ++ | 98 | 393.4 | 394.4 |
| 289 | +++ | 99 | 391.4 | 392.4 |
| 290 | +++ | 99 | 407.4 | 408.4 |
| 291 | +++ | 99 | 435.4 | 436.4 |
| 292 | ++ | 99 | 455.4 | 456.4 |
| 293 | +++ | 99 | 435.4 | 436.4 |
| 294 | +++ | 99 | 419.4 | 420.4 |
| 295 | +++ | 99 | 447.4 | 448.4 |
| 296 | +++ | 99 | 465.3 | 466.3 |
| 297 | +++ | 99 | 515.4 | 516.4 |
| 298 | +++ | 99 | 481.8 | 482.8 |
| 299 | ++ | 99 | 447.8 | 448.8 |
| 300 | +++ | 99 | 414.3 | 415.3 |
| 301 | +++ | 98 | 414.3 | 415.3 |
| 302 | +++ | 99 | 371.8 | 372.8 |
| 303 | ++ | 98 | 453.3 | 454.3 |
| 304 | +++ | 98 | 453.4 | 454.4 |
| 305 | +++ | 98 | 406.4 | 407.4 |
| 306 | +++ | 98 | 444.4 | 445.4 |
| 307 | + | 98 | 417.3 | 418.3 |
| 308 | +++ | 98 | 390.4 | 391.4 |
| 309 | +++ | 98 | 428.4 | 429.4 |
| 310 | +++ | 99 | 481.8 | 482.8 |
| 311 | +++ | 99 | 439.4 | 440.4 |
| 312 | +++ | 99 | 427.4 | 428.4 |
| 313 | +++ | 99 | 467.3 | 468.3 |
| 314 | +++ | 99 | 359.8 | 360.8 |
| 315 | ++ | 99 | 399.8 | 400.8 |
| 316 | +++ | 98 | 430.3 | 431.3 |
| 317 | ++ | 95 | 448.8 | 449.8 |
| 318 | ++ | 96 | 450.8 | 451.8 |
| 319 | + | 95 | 377.3 | 378.3 |
| 320 | + | 99 | 415.2 | 416.2 |
| 321 | + | 99 | 417.2 | 418.2 |

TABLE 2-continued

| Compound No. | SH-SY5Y EC50, μM | Purity (%) | Molecular Weight | Observed m/z (M + H) |
|---|---|---|---|---|
| 322 | + | 99 | 410.8 | 411.8 |
| 323 | + | 97 | 392.4 | 393.4 |
| 324 | + | 99 | 430.4 | 431.4 |
| 325 | + | 99 | 432.3 | 433.3 |
| 326 | +++ | 97 | 457.4 | 458.4 |
| 327 | +++ | 99 | 457.4 | 458.4 |
| 328 | +++ | 99 | 441.4 | 442.4 |
| 329 | + | 96 | 342.8 | 343.8 |
| 330 | + | 96 | 380.8 | 381.8 |
| 331 | + | 98 | 382.8 | 383.8 |
| 332 | + | 98 | 394.4 | 395.4 |
| 333 | ++ | 98 | 410.4 | 411.4 |
| 334 | ++ | 98 | 411.3 | 412.3 |
| 335 | ++ | 98 | 343.8 | 344.8 |
| 336 | ++ | 98 | 375.4 | 376.4 |
| 337 | ++ | 98 | 415.3 | 416.3 |
| 338 | ++ | 98 | 413.4 | 414.4 |
| 339 | ++ | 98 | 406.4 | 407.4 |
| 340 | + | 95 | 451.4 | 452.4 |
| 341 | ++ | 95 | 409.4 | 410.4 |
| 342 | +++ | 98 | 391.4 | 392.4 |
| 343 | ++ | 98 | 431.3 | 432.3 |
| 344 | +++ | 98 | 429.4 | 430.4 |
| 345 | ++ | 95 | 442.4 | 443.4 |
| 346 | +++ | 97 | 422.4 | 423.4 |

"+" represents 10 μM > $EC_{50}$ > 3 μM
"++" represents 3 μM > $EC_{50}$ > 0.5 μM
"+++" represents $EC_{50}$ < 0.5 μM

Example 3

Preparation of N-(3-(benzo[d]thiazol-2-yl)-6-fluoroimidazo[1,2-a]pyridin-2-yl)-3,3,3-trifluoropropanamide (381)

Method 3

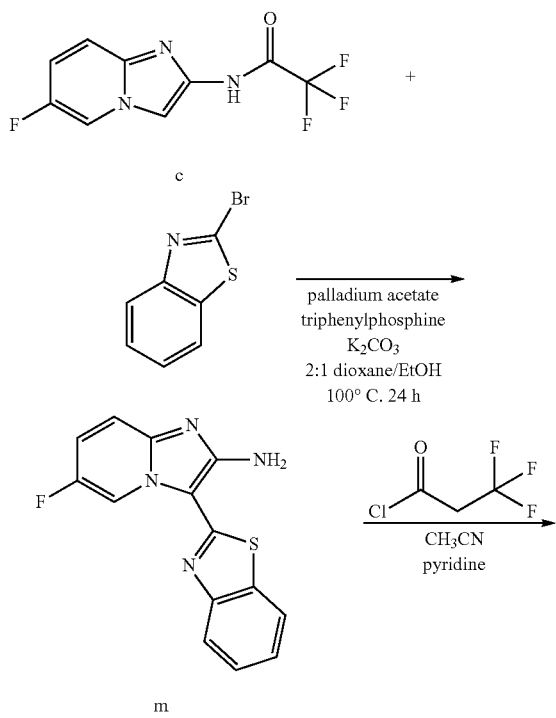

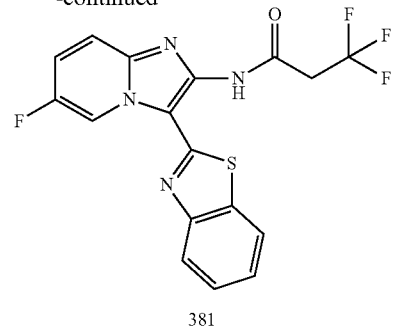

381

Synthesis of 3-(benzo[d]thiazol-2-yl)-6-fluoroimidazo[1,2-a]pyridin-2-amine (m)

2,2,2-Trifluoro-N-(6-fluoro-imidazo[1,2-a]pyridin-2-yl)-acetamide (compound c, 6 g, 0.02 mol), 2-bromo-1,3-benzothiazole (6.8 g, 32 mmol), potassium carbonate (7000 mg, 0.05 mol), and triphenylphosphine (1000 mg, 0.005 mol) were diluted with 60 ml of a 2:1 solution of dioxane/ethanol and treated with palladium acetate (500 mg, 0.002 mol). The reaction was heated at 100° C. overnight. The reaction was cooled and resulting solid was filtered and washed with dichloromethane then dried to give 3-(benzo[d]thiazol-2-yl)-6-fluoroimidazo[1,2-a]pyridin-2-amine as a yellow solid. Rf 0.37, 70% ethyl acetate/hexanes; MS m/z 285 (M+H).

Synthesis of N-(3-(benzo[d]thiazol-2-yl)-6-fluoroimidazo[1,2-a]pyridin-2-yl)-3,3,3-trifluoropropanamide (381)

3-(benzo[d]thiazol-2-yl)-6-fluoroimidazo[1,2-a]pyridin-2-amine (compound m, 250 mg, 0.0009 mol) in pyridine (0.2 mL) was treated with 3,3,3-trifluoropropionyl chloride (0.134 mL, 0.0011 mol) and shaken at room temperature for about 45 min. The solvent was removed and the crude product was purified by column chromatography (50% ethyl acetate/hexane) to give N-(3-(benzo[d]thiazol-2-yl)-6-fluoroimidazo[1,2-a]pyridin-2-yl)-3,3,3-trifluoropropanamide as a white solid. Rf 0.32, 70% ethyl acetate/hexanes; MS m/z 395 (M+H). SH-SY5Y_EC50 (μM): 2.1258.

The following compounds were prepared according to the procedures of Method 3. In one embodiment, 2-aminopyridazine was used as the starting material in preparing compounds 382, 385-390, 394-397 and 415, which contain a imidazo[1,2-b]pyridazin moiety. In another embodiment, 2-aminopyrimidine was used as the starting material for preparing compounds 362 and 377, which contain a imidazo[1,2-a]pyrimidin moiety, The number next to each compound listed below corresponds to the compound number in Table 3. Following is a List of the Compounds Prepared by Method 3:

N-(6-fluoro-3-(pyridin-2-yl)imidazo[1,2-a]pyridin-2-yl)-3,3-dimethylbutanamide 347

N-(6-fluoro-3-(pyridin-3-yl)imidazo[1,2-a]pyridin-2-yl)-3,3-dimethylbutanamide 348

N-(6-fluoro-3-(6-fluoropyridin-3-yl)imidazo[1,2-a]pyridin-2-yl)-3,3-dimethylbutanamide 349

N-(3-(6-cyanopyridin-3-yl)-6-fluoroimidazo[1,2-a]pyridin-2-yl)-3,3-dimethylbutanamide 350

N-(6-fluoro-3-(pyridin-4-yl)imidazo[1,2-a]pyridin-2-yl)-3,3-dimethylbutanamide 351

N-(6-fluoro-3-(5-fluoropyridin-2-yl)imidazo[1,2-a]pyridin-2-yl)-3,3-dimethylbutanamide 352

N-(6-fluoro-3-(5-(trifluoromethyl)pyridin-2-yl)imidazo[1,2-a]pyridin-2-yl)-3,3-dimethylbutanamide 353
N-(3-(5-cyanopyridin-2-yl)-6-fluoroimidazo[1,2-a]pyridin-2-yl)-3,3-dimethylbutanamide 354
N-(6-fluoro-3-(5-(trifluoromethyl)pyridin-3-yl)imidazo[1,2-a]pyridin-2-yl)-3,3-dimethylbutanamide 355
N-(3,3-dimethylbutanoyl)-N-(6-fluoro-3-(5-methylpyridin-2-yl)imidazo[1,2-a]pyridin-2-yl)-3,3-dimethylbutanamide 356
N-(3,3-dimethylbutanoyl)-N-(6-fluoro-3-(6-(trifluoromethyl)pyridin-2-yl)imidazo[1,2-a]pyridin-2-yl)-3,3-dimethylbutanamide 357
N-(3-(benzo[d]thiazol-2-yl)-6-fluoroimidazo[1,2-a]pyridin-2-yl)-N-(3,3-dimethylbutanoyl)-3,3-dimethylbutanamide 358
N-(6-fluoro-3-(5-methylpyridin-2-yl)imidazo[1,2-a]pyridin-2-yl)-3,3-dimethylbutanamide 359
N-(3-(benzo[d]thiazol-2-yl)-6-fluoroimidazo[1,2-a]pyridin-2-yl)-3,3-dimethylbutanamide 360
N-(6-fluoro-3-(6-(trifluoromethyl)pyridin-2-yl)imidazo[1,2-a]pyridin-2-yl)-3,3-dimethylbutanamide 361
N-(6-fluoro-3-(pyrimidin-2-yl)imidazo[1,2-a]pyridin-2-yl)-3,3-dimethylbutanamide 362
N-(3-(5-chloropyridin-2-yl)-6-fluoroimidazo[1,2-a]pyridin-2-yl)-3,3-dimethylbutanamide 363
N-(3-(4-chloropyridin-2-yl)-6-fluoroimidazo[1,2-a]pyridin-2-yl)-3,3-dimethylbutanamide 364
N-(6-fluoro-3-(4-methylpyridin-2-yl)imidazo[1,2-a]pyridin-2-yl)-3,3-dimethylbutanamide 365
N-(6-fluoro-3-(4-(trifluoromethyl)pyridin-2-yl)imidazo[1,2-a]pyridin-2-yl)-3,3-dimethylbutanamide 366
N-(6-fluoro-3-(6-methoxypyridin-2-yl)imidazo[1,2-a]pyridin-2-yl)-3,3-dimethylbutanamide 367
N-(6-fluoro-3-(5-fluoropyridin-2-yl)imidazo[1,2-a]pyridin-2-yl)-2,3-dimethylbutanamide 368
4,4,4-trifluoro-N-(6-fluoro-3-(5-fluoropyridin-2-yl)imidazo[1,2-a]pyridin-2-yl)-3-methylbutanamide 369
N-(6-fluoro-3-(1-isopropyl-1H-pyrazol-4-yl)imidazo[1,2-a]pyridin-2-yl)-3,3-dimethylbutanamide 370
N-(6-fluoro-3-(thiazol-2-yl)imidazo[1,2-a]pyridin-2-yl)-3,3-dimethyl butanamide 371
N-(3-(benzo[d]thiazol-2-yl)-6-fluoroimidazo[1,2-a]pyridin-2-yl)-4,4-dimethylpentanamide 372
N-(3-(benzo[d]thiazol-2-yl)-6-fluoroimidazo[1,2-a]pyridin-2-yl)-2,3-dimethylbutanamide 373
N-(3-(benzo[d]thiazol-2-yl)-6-fluoroimidazo[1,2-a]pyridin-2-yl)-4,4,4-trifluoro-3-methylbutanamide 374
N-(3-(benzo[d]thiazol-2-yl)-6-fluoroimidazo[1,2-a]pyridin-2-yl)-2-(1-methylcyclopentyl)acetamide 375
N-(3-(benzo[d]thiazol-2-yl)-6-(trifluoromethyl)imidazo[1,2-a]pyridin-2-yl)-3,3-dimethylbutanamide 376
N-(6-fluoro-3-(4-(trifluoromethyl)pyrimidin-2-yl)imidazo[1,2-a]pyridin-2-yl)-3,3-dimethylbutanamide 377
N-(3-(benzo[d]thiazol-2-yl)-6-fluoroimidazo[1,2-a]pyridin-2-yl)cyclopentanecarboxamide 378
N-(3-(benzo[d]thiazol-2-yl)-6-fluoroimidazo[1,2-a]pyridin-2-yl)-2-(4-fluorophenyl)acetamide 379
N-(3-(benzo[d]thiazol-2-yl)-6-fluoroimidazo[1,2-a]pyridin-2-yl)-2-cyclopentylacetamide 380
N-(3-(benzo[d]thiazol-2-yl)-6-fluoroimidazo[1,2-a]pyridin-2-yl)-3,3,3-trifluoropropanamide 381
N-(3-(benzo[d]thiazol-2-yl)-6-methylimidazo[1,2-b]pyridazin-2-yl)-3,3-dimethylbutanamide 382
4,4,4-trifluoro-N-(6-fluoro-3-(thiazol-2-yl)imidazo[1,2-a]pyridin-2-yl)-3-methylbutanamide 383
N-(6-fluoro-3-(thiazol-2-yl)imidazo[1,2-a]pyridin-2-yl)-2-(4-fluorophenyl)acetamide 384
N-(3-(benzo[d]thiazol-2-yl)-6-methylimidazo[1,2-b]pyridazin-2-yl)-2-(4-fluorophenyl)acetamide 385
N-(3-(benzo[d]thiazol-2-yl)-6-methylimidazo[1,2-b]pyridazin-2-yl)-4,4,4-trifluoro-3-methylbutanamide 386
3,3-dimethyl-N-(6-methyl-3-(thiazol-2-yl)imidazo[1,2-b]pyridazin-2-yl)butanamide 387
4,4,4-trifluoro-3-methyl-N-(6-methyl-3-(thiazol-2-yl)imidazo[1,2-b]pyridazin-2-yl)butan amide 388
4,4-difluoro-N-(6-methyl-3-(thiazol-2-yl)imidazo[1,2-b]pyridazin-2-yl)cyclohexanecarboxamide 389
2-(4-fluorophenyl)-N-(6-methyl-3-(thiazol-2-yl)imidazo[1,2-b]pyridazin-2-yl)acetamide 390
4,4-difluoro-N-(6-fluoro-3-(thiazol-2-yl)imidazo[1,2-a]pyridin-2-yl)cyclohexanecarboxamide 391
N-(3-(benzo[d]thiazol-2-yl)-5-methylimidazo[1,2-a]pyridin-2-yl)-3,3-dimethylbutanamide 392
N-(3-(benzo[d]thiazol-2-yl)-5-methylimidazo[1,2-a]pyridin-2-yl)-2-(4-fluorophenyl)acetamide 393
3,3-dimethyl-N-(6-methyl-3-(4-(trifluoromethyl)pyridin-2-yl)imidazo[1,2-b]pyridazin-2-yl)butanamide 394
2-(4-fluorophenyl)-N-(6-methyl-3-(4-(trifluoromethyl)pyridin-2-yl)imidazo[1,2-b]pyridazin-2-yl)acetamide 395
4,4,4-trifluoro-3-methyl-N-(6-methyl-3-(4-(trifluoromethyl)pyridin-2-yl)imidazo[1,2-b]pyridazin-2-yl)butanamide 396
4,4-difluoro-N-(6-methyl-3-(4-(trifluoromethyl)pyridin-2-yl)imidazo[1,2-b]pyridazin-2-yl)cyclohexanecarboxamide 397
3,3-dimethyl-N-(6-(trifluoromethyl)-3-(4-(trifluoromethyl)pyridin-2-yl)imidazo[1,2-a]pyridin-2-yl)butanamide 398
4,4,4-trifluoro-3-methyl-N-(6-(trifluoromethyl)-3-(4-(trifluoromethyl)pyridin-2-yl)imidazo[1,2-a]pyridin-2-yl)butanamide 399
2-(4-fluorophenyl)-N-(6-(trifluoromethyl)-3-(4-(trifluoromethyl)pyridin-2-yl)imidazo[1,2-a]pyridin-2-yl)acetamide 400
4,4,4-trifluoro-N-(6-fluoro-3-(4-(trifluoromethyl)pyridin-2-yl)imidazo[1,2-a]pyridin-2-yl)-3-methylbutanamide 401
4,4-difluoro-N-(6-fluoro-3-(4-(trifluoromethyl)pyridin-2-yl)imidazo[1,2-a]pyridin-2-yl)cyclohexanecarboxamide 402
2-(4-fluorophenyl)-N-(3-(4-(trifluoromethyl)pyridin-2-yl)imidazo[1,2-a]pyridin-2-yl)acetamide 403
3,3-dimethyl-N-(3-(4-(trifluoromethyl)pyridin-2-yl)imidazo[1,2-a]pyridin-2-yl)butanamide 404
4,4,4-trifluoro-3-methyl-N-(3-(4-(trifluoromethyl)pyridin-2-yl)imidazo[1,2-a]pyridin-2-yl)butanamide 405
3,3-dimethyl-N-(3-(thiazol-2-yl)imidazo[1,2-a]pyridin-2-yl)butanamide 406
2-(4-fluorophenyl)-N-(3-(thiazol-2-yl)imidazo[1,2-a]pyridin-2-yl)acetamide 407
4,4,4-trifluoro-3-methyl-N-(3-(thiazol-2-yl)imidazo[1,2-a]pyridin-2-yl)butanamide 408
4,4-difluoro-N-(3-(thiazol-2-yl)imidazo[1,2-a]pyridin-2-yl)cyclohexanecarboxamide 409
N-(6-fluoro-3-(4-(trifluoromethyl)pyridin-2-yl)imidazo[1,2-a]pyridin-2-yl)-2-(4-fluorophenyl)acetamide 410
4,4-difluoro-N-(3-(4-(trifluoromethyl)pyridin-2-yl)imidazo[1,2-a]pyridin-2-yl)cyclohexanecarboxamide 411
2,2-difluoro-N-(6-fluoro-3-(4-(trifluoromethyl)pyridin-2-yl)imidazo[1,2-a]pyridin-2-yl)cyclopropanecarboxamide 412
2,2-difluoro-N-(3-(4-(trifluoromethyl)pyridin-2-yl)imidazo[1,2-a]pyridin-2-yl)cyclopropanecarboxamide 413
3,3-dimethyl-N-(3-(thiazol-4-yl)imidazo[1,2-a]pyridin-2-yl)butanamide 414

N-(6-methoxy-3-(thiazol-2-yl)imidazo[1,2-b]pyridazin-2-yl)-3,3-dimethylbutanamide 415

3,3-dimethyl-N-(3-(2-methylthiazol-4-yl)imidazo[1,2-a]pyridin-2-yl)butanamide 416

3,3-dimethyl-N-(3-(5-methylthiazol-2-yl)imidazo[1,2-a]pyridin-2-yl)butanamide 417

4,4,4-trifluoro-3-methyl-N-(3-(5-methylthiazol-2-yl)imidazo[1,2-a]pyridin-2-yl)butanamide 418

Table 3 sets forth potencies, purity, calculated molecular weights and measured molecular weights of representative compounds of the invention in the SH-SY5Y native cell line in a FLIPR assay, for a selection of compounds. The compound numbers in Table 3 correspond to the compound numbers following each compound listed above in Example 3.

TABLE 3

| Compound No. | SH-SY5Y EC50, μM | Purity (%) | Molecular Weight | Observed m/z (M + H) |
|---|---|---|---|---|
| 347 | + | 90 | 326.4 | 327.4 |
| 348 | + | 95 | 326.4 | 327.4 |
| 349 | ++ | 90 | 344.4 | 345.4 |
| 350 | ++ | 90 | 351.4 | 352.4 |
| 351 | + | 90 | 326.4 | 327.4 |
| 352 | ++ | 90 | 344.4 | 345.4 |
| 353 | +++ | 90 | 394.4 | 395.4 |
| 354 | + | 95 | 351.4 | 352.4 |
| 355 | + | 100 | 394.4 | 395.4 |
| 356 | + | 90 | 438.5 | 439.5 |
| 357 | + | 100 | 492.5 | 493.5 |
| 358 | + | 90 | 480.6 | 481.6 |
| 359 | ++ | 95 | 340.4 | 341.4 |
| 360 | +++ | 90 | 382.5 | 383.5 |
| 361 | +++ | 100 | 394.4 | 395.4 |
| 362 | + | 90 | 327.4 | 328.4 |
| 363 | +++ | 97 | 360.8 | 361.8 |
| 364 | ++ | 99 | 360.8 | 361.8 |
| 365 | ++ | 99 | 340.4 | 341.4 |
| 366 | +++ | 99 | 394.4 | 395.4 |
| 367 | ++ | 100 | 356.4 | 357.4 |
| 368 | + | 100 | 344.4 | 345.4 |
| 369 | + | 100 | 384.3 | 385.3 |
| 370 | + | 100 | 357.4 | 358.4 |
| 371 | ++ | 90 | 332.4 | 333.4 |
| 372 | ++ | 95 | 396.5 | 397.5 |
| 373 | + | 95 | 382.5 | 383.5 |
| 374 | + | 90 | 422.4 | 423.4 |
| 375 | +++ | 100 | 408.5 | 409.5 |
| 376 | +++ | 100 | 432.5 | 433.5 |
| 377 | + | 98 | 395.4 | 396.4 |
| 378 | + | 95 | 380.4 | 381.4 |
| 379 | ++ | 90 | 420.4 | 421.4 |
| 380 | ++ | 90 | 394.5 | 395.5 |
| 381 | ++ | 95 | 394.3 | 395.3 |
| 382 | + | 98 | 379.5 | 380.5 |
| 383 | + | 98 | 372.3 | 373.3 |
| 384 | ++ | 92 | 370.4 | 371.4 |
| 385 | + | 98 | 417.5 | 418.5 |
| 386 | + | 98 | 419.4 | 420.4 |
| 387 | + | 95 | 329.4 | 330.4 |
| 388 | + | 95 | 369.4 | 370.4 |
| 389 | + | 95 | 377.4 | 378.4 |
| 390 | + | 95 | 367.4 | 368.4 |
| 391 | +++ | 95 | 380.4 | 381.4 |
| 392 | + | 98 | 378.5 | 379.5 |
| 393 | ++ | 98 | 416.5 | 417.5 |
| 394 | + | 95 | 391.4 | 392.4 |
| 395 | + | 95 | 429.4 | 430.4 |
| 396 | + | 95 | 431.3 | 432.3 |
| 397 | + | 95 | 439.4 | 440.4 |
| 398 | +++ | 95 | 444.4 | 445.4 |
| 399 | ++ | 95 | 484.3 | 485.3 |
| 400 | +++ | 95 | 482.4 | 483.4 |
| 401 | ++ | 95 | 434.3 | 435.3 |
| 402 | +++ | 95 | 442.4 | 443.4 |
| 403 | +++ | 95 | 414.4 | 415.4 |
| 404 | ++ | 95 | 376.4 | 377.4 |

TABLE 3-continued

| Compound No. | SH-SY5Y EC50, μM | Purity (%) | Molecular Weight | Observed m/z (M + H) |
|---|---|---|---|---|
| 405 | ++ | 98 | 416.3 | 417.3 |
| 406 | ++ | 95 | 314.4 | 315.4 |
| 407 | ++ | 95 | 352.4 | 353.4 |
| 408 | + | 95 | 354.4 | 355.4 |
| 409 | ++ | 95 | 362.4 | 363.4 |
| 410 | +++ | 95 | 432.3 | 433.3 |
| 411 | +++ | 90 | 424.4 | 425.4 |
| 412 | + | 90 | 400.3 | 401.3 |
| 413 | ++ | 98 | 382.3 | 383.3 |
| 414 | + | 98 | 314.4 | 315.4 |
| 415 | + | 97 | 345.4 | 346.4 |
| 416 | + | 98 | 328.4 | 329.4 |
| 417 |   | 98 | 328.4 | 329.4 |
| 418 |   | 98 | 368.4 | 369.4 |

"+" represents 10 μM > $EC_{50}$ > 3 μM

"++" represents 3 μM > $EC_{50}$ > 0.5 μM

"+++" represents $EC_{50}$ < 0.5 μM

Example 4

Preparation of 3,3-Dimethyl-N-[5-methyl-3-(3-trifluoromethyl-phenyl)-imidazo[1,2-a]pyridin-2-yl]-butyramide (419)

Method 4

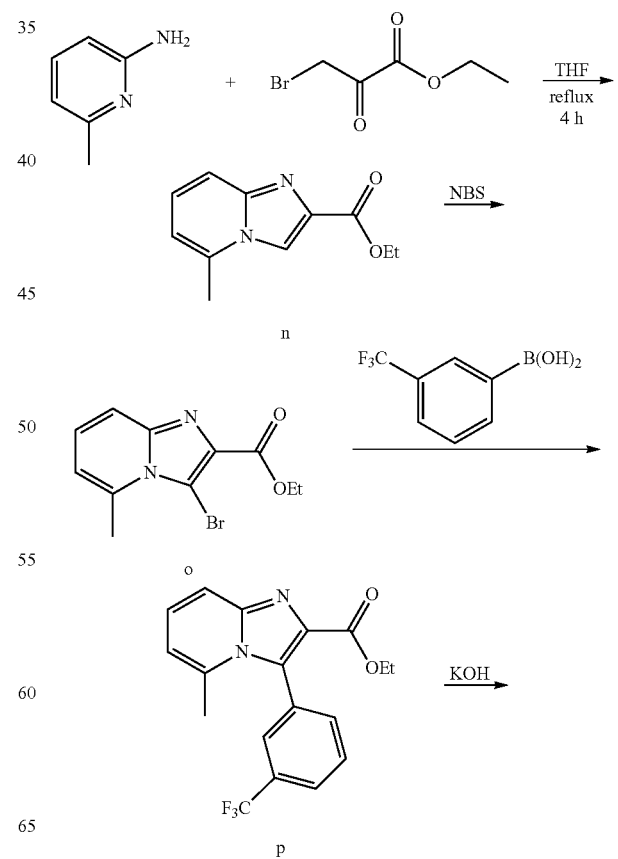

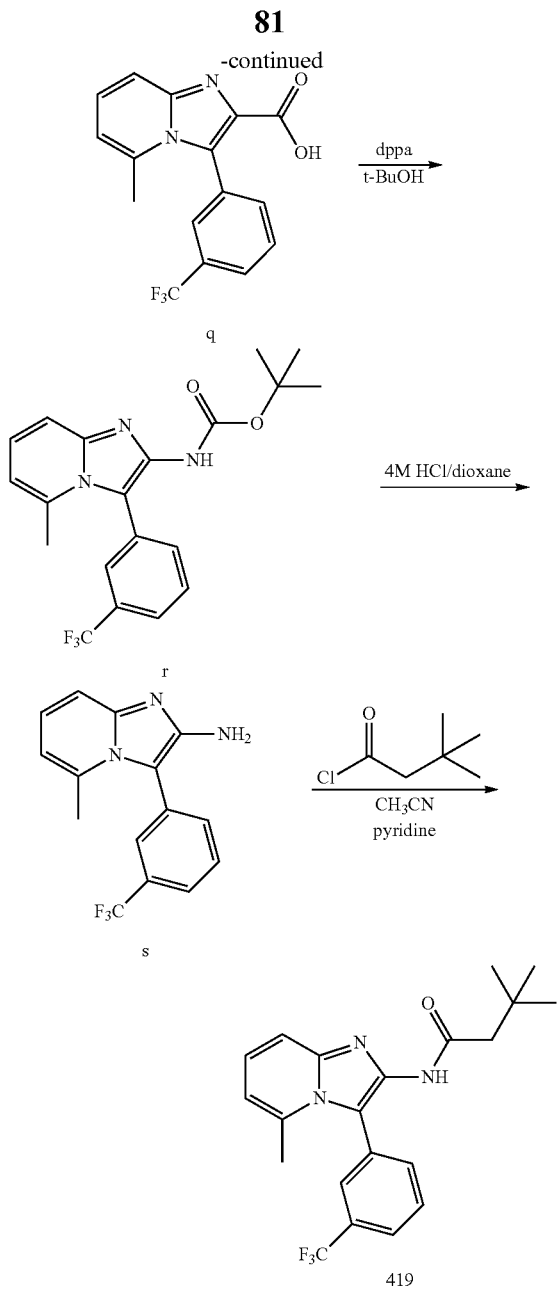

carboxylic acid ethyl ester (compound n, 0.3 g, 0.001 mol) in acetonitrile (7 mL) at 0° C. The reaction was stirred at 0° C. for 15 minutes. The solvent removed then water (10 mL) and ethyl acetate (10 mL) was added. The layers were separated and the organic layer dried (magnesium sulfate) then removed. The crude product was chromatographed using 30% ethyl acetate/hexanes to give 3-Bromo-5-methyl-imidazo[1,2-a]pyridine-2-carboxylic acid ethyl ester as a light brown solid. Rf 0.35, 80% ethyl acetate/hexanes; MS m/z 284 (M+H).

Synthesis of 5-Methyl-3-(3-trifluoromethyl-phenyl)-imidazo[1,2-a]pyridine-2-carboxylic acid ethyl ester (p)

3-Bromo-5-methyl-imidazo[1,2-a]pyridine-2-carboxylic acid ethyl ester (compound o, 0.6 g, 0.002 mol), potassium carbonate (0.6 g, 0.004 mol), triphenylphosphine (0.06 g, 0.0002 mol), 3-(trifluoromethyl)phenylboronic acid (0.4 g, 0.002 mol) and bis(acetato) bis(triphenylphosphine)palladium (II) (0.08 g, 0.0001 mol) were mixed in a microwave vial. The mixture was purged with argon. Isopropyl alcohol (20 mL) and water (3 mL) was added. The mixture was heated (120° C.) by microwaved for 25 minutes. The solvent removed then water (10 mL) and ethyl acetate (10 mL) was added. The layers were separated and the organic layer dried (magnesium sulfate) then removed. The crude product was chromatographed using 50% ethyl acetate/hexanes to give 350 mg of 5-methyl-3-(3-trifluoromethyl-phenyl)-imidazo[1,2-a]pyridine-2-carboxylic acid ethyl ester as a white solid. Rf 0.42, 50% ethyl acetate/hexanes; MS m/z 349 (M+H).

Synthesis of 5-Methyl-3-(3-(trifluoromethyl)phenyl)imidazo[1,2-a]pyridine-2-carboxylic acid (q)

Potassium hydroxide (0.2 g, 0.003 mol) was added to a suspension of 5-Methyl-3-(3-trifluoromethyl-phenyl)-imidazo[1,2-a]pyridine-2-carboxylic acid ethyl ester (compound p, 0.35 g, 0.0010 mol) in methanol (0.4 mL) and water (4.7 mL). Stirred at 80° C. for 1 hour. The methanol was removed and 6N HCl added to the residue until pH approx. 5. The white solid that formed was filtered to give 290 mg of 5-methyl-3-(3-(trifluoromethyl)phenyl)imidazo[1,2-a]pyridine-2-carboxylic acid as a white solid. Rf 0.20, 100% ethyl acetate; MS m/z 319 (M−H).

Synthesis of [5-Methyl-3-(3-trifluoromethyl-phenyl)-imidazo[1,2-a]pyridin-2-yl]-carbamic acid tert-butyl ester (r)

5-methyl-3-(3-(trifluoromethyl)phenyl)imidazo[1,2-a]pyridine-2-carboxylic acid (0.28 g, 0.00087 mol) was dissolved in tert-Butyl alcohol (compound q, 6 mL, 0.06 mol) and triethylamine (0.15 mL, 0.0010 mol). Diphenylphosphonic azide (0.23 mL, 0.0010 mol) was added and was stirred at 85° C. for 6 hours. Reaction was cooled then water was added and the solvent evaporated. Aqueous layer was extracted with ethyl acetate. The organics were combined then dried (magnesium sulfate) and removed in vacuo. The crude product was chromatographed using 60% ethyl acetate/hexanes to give 130 mg of [5-Methyl-3-(3-trifluoromethyl-phenyl)-imidazo[1,2-a]pyridin-2-yl]-carbamic acid tert-butyl ester as a yellow solid. Rf 0.40, 60% ethyl acetate; MS m/z 392 (M+H).

Synthesis of 5-Methyl-3-(3-trifluoromethyl-phenyl)-imidazo[1,2-a]pyridin-2-ylamine (s)

4 M of Hydrogen chloride in 1,4-dioxane (0.8 mL) was added to [5-Methyl-3-(3-trifluoromethyl-phenyl)-imidazo[1, Synthesis of 5-Methylimidazo[1,2-a]pyridine-2-carboxylic acid ethyl ester (n)

2-Amino-6-methylpyridine (5 g, 0.05 mol) was dissolved in tetrahydrofuran (100 mL). Ethyl bromopyruvate (9 g, 0.05 mol) was added and the mixture was refluxed for 4 hours. The reaction was cooled and the solid that formed was filtered to give 6 grams of 5-methylimidazo[1,2-a]pyridine-2-carboxylic acid ethyl ester. Rf 0.45, 2% methanol/dichloromethane; MS m/z 205 (M+H).

Synthesis of 3-Bromo-5-methyl-imidazo[1,2-a]pyridine-2-carboxylic acid ethyl ester (o)

N-Bromosuccinimide (0.288 g, 0.00162 mol) was added in portions to a solution of 5-methylimidazo[1,2-a]pyridine-2-

2-a]pyridin-2-yl]-carbamic acid tert-butyl ester (compound r, 0.14 g, 0.00036 mol). The mixture was stirred at room temperature for 2 hours. Solvent evaporated to give 0.1 g as a yellow oil. Rf 0.42, 100% ethyl acetate; MS m/z 292 (M+H).

Synthesis of 3,3-Dimethyl-N-[5-methyl-3-(3-trifluoromethyl-phenyl)-imidazo[1,2-a]pyridin-2-yl]-butyramide (419)

5-Methyl-3-(3-trifluoromethyl-phenyl)-imidazo[1,2-a]pyridin-2-ylamine (compound s, 0.05 g, 0.0002 mol) was dissolved in acetonitrile (0.9 mL) and pyridine (0.03 mL, 0.0003 mol). t-butylacetyl chloride (0.028 mL, 0.00020 mol) was added and the mixture was stirred at room temperature for 4 hours. Solvent was removed then ethyl acetate and saturated sodium bicarbonate was added. The layers were separated and the organic layer dried (magnesium sulfate) then removed. The crude product was chromatographed using 60% ethyl acetate/hexanes to give 39 mg of 3,3-Dimethyl-N-(5-methyl-3-(3-trifluoromethyl-phenyl)-imidazo[1,2-a]pyridin-2-yl)-butyramide as a white solid. Rf 0.27, 100% ethyl acetate; MS m/z 390 (M+H). SH-SY5Y_EC50: 0.3399.

The following compounds were prepared according to the procedures of Method 4. The number next to each compound listed below corresponds to the compound number in Table 4.

Following is a List of the Compounds Prepared by Method 4:

3,3-dimethyl-N-(5-methyl-3-(3-(trifluoromethyl)phenyl)imidazo[1,2-a]pyridin-2-yl)butanamide 419

4,4,4-trifluoro-3-methyl-N-(5-methyl-3-(3-(trifluoromethyl)phenyl)imidazo[1,2-a]pyridin-2-yl)butanamide 420

Table 4 sets forth potencies, purity, calculated molecular weights and measured molecular weights of representative compounds of the invention in the SH-SY5Y native cell line in a FLIPR assay, for a selection of compounds. The compound numbers in Table 4 correspond to the compound numbers following each compound listed above in Example 4.

TABLE 4

| Compound No. | SH-SY5Y EC50, μM | Purity (%) | Molecular Weight | Observed m/z (M + H) |
|---|---|---|---|---|
| 419 | +++ | 98 | 389.4 | 390.4 |
| 420 | ++ | 98 | 429.4 | 430.4 |

"+" represents 10 μM > $EC_{50}$ > 3 μM
"++" represents 3 μM > $EC_{50}$ > 0.5 μM
"+++" represents $EC_{50}$ < 0.5 μM

Example 5

Preparation of 3,3,3-trifluoro-N-(6-fluoro-3-methylimidazo[1,2-a]pyridin-2-yl)propanamide (7)

Method 5

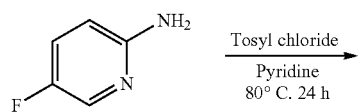

Synthesis of N-(5-fluoropyridin-2-yl)-4-methylbenzenesulfonamide (1)

2-Amino-5-fluoropyridine (4.0 g, 0.036 mol) was dissolved in pyridine (40 mL) and p-toluenesulfonyl chloride (7.5 g, 0.039 mol) was added. The reaction was heated at 80° C. for 24 hours then cooled and the pyridine was removed under vacuum. The residue was partioned between water (100 mL) and ethyl acetate (100 mL). The layers were separated and the organic layer was washed (3×100 mL) with water then dried and solvent stripped to give clean N-(5-fluoropyridin-2-yl)-4-methylbenzenesulfonamide 1 Rf 0.42, 50% E/H; MS m/z 267 (M+H).

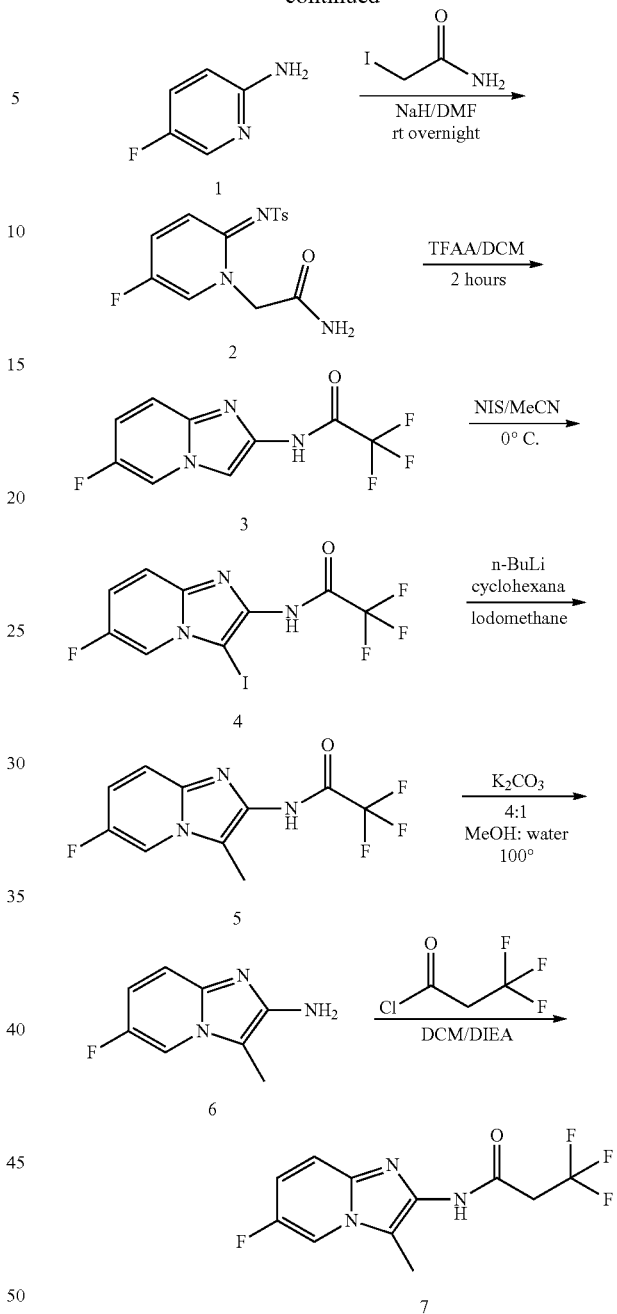

Synthesis of 2-(5-fluoro-2-(tosylimino)pyridin-1(2H)-yl)acetamide (2)

Sodium hydride (0.43 g, 0.018 mol) was mixed with N,N-Dimethylformamide (67.4 mL) and N-(5-fluoropyridin-2-yl)-4-methylbenzenesulfonamide 1 (4.0 g, 0.015 mol) was added. The reaction was stirred at room temperature for 10 minutes. Iodoacetamide (3.3 g, 0.018 mol) was added and the mixture was stirred at room temperature for 24 hours. The reaction was poured into water (100 mL) and extracted with ethyl acetate (4×75 mL). Organic layers were combined then dried with magnesium sulfate and the solvent removed. The crude product was chromatographed on silica using 5% methanol in dichloromethane to give 2-(5-fluoro-2-(tosylimino)pyridin-1(2H)-yl)acetamide 2 Rf 0.26, 5% methanol.dichloromethane; MS m/z 324 (M+H)

Synthesis of 2,2,2-trifluoro-N-(6-fluoroimidazo[1,2-a]pyridin-2-yl)acetamide (3)

2-(5-fluoro-2-(tosylimino)pyridin-1(2H)-yl)acetamide (1.5 g, 0.0046 mol) was mixed with dichloromethane (18 mL) and trifluoroacetic anhydride (10 mL, 0.09 mol) was added. The reaction was stirred at room temperature 30 min. The solvent was removed and residue taken up in ethyl acetate (50 mL) then washed with saturated NaHCO$_3$ (3×50 mL). The organic layer was dried with magnesium sulfate and the solvent removed. The residue was chromatographed on silica (70% ethyl acetate/hexanes) to give 2,2,2-trifluoro-N-(6-fluoroimidazo[1,2-a]pyridin-2-yl)acetamide 3 Rf 0.35, 70% ethyl acetate/hexanes; MS m/z 248 (M+H)

Synthesis of 2,2,2-trifluoro-N-(6-fluoro-3-iodoimidazo[1,2-a]pyridin-2-yl)acetamide (4)

2,2,2-trifluoro-N-(6-fluoroimidazo[1,2-a]pyridin-2-yl)acetamide (0.89 g, 0.0036 mol) was dissolved in acetonitrile (20 mL) and was cooled at 0° C. N-Iodosuccinimide (0.89 g, 0.0040 mol) was added and the reaction was stirred for 30 minutes. The mixture was poured into water (100 mL) and extracted with ethyl acetate (3×100 mL). The combined organics were dried with magnesium sulfate and the solvent removed. The residue was chromatographed on silica (60% ethyl acetate/hexanes) to give 2,2,2-trifluoro-N-(6-fluoro-3-iodoimidazo[1,2-a]pyridin-2-yl)acetamide 4 Rf 0.40, 60% ethyl acetate/hexanes; MS m/z 374 (M+H).

Synthesis of 2,2,2-trifluoro-N-(6-fluoro-3-methylimidazo[1,2-a]pyridin-2-yl)acetamide (5)

2,2,2-trifluoro-N-(6-fluoro-3-iodoimidazo[1,2-a]pyridin-2-yl)acetamide (500 g, 0.00134 mol) was dissolved in tetrahydrofuran (16 mL) and was cooled at −78° C. N-Butyllithium (2 molarin cyclohexane, 1.6 mL) was added and the reaction was warmed to −20 for 15 minutes then chilled to 78° C. Methyl iodide (110 uL, 0.0017 mol) was added and the reaction was allowed to warm to room temperature. The reaction was poured into ice water and extracted with ethyl acetate (3×50 mL). The combined organics were dried (magnesium sulfate) and solvent removed. Residue chromatographed on silica (50% ethyl acetate/hexanes) to give 2,2,2-trifluoro-N-(6-fluoro-3-methylimidazo[1,2-a]pyridin-2-yl)acetamide 5 Rf 0.47, 50% ethyl acetate/hexanes; MS m/z 262 (M+H).

Synthesis of 6-fluoro-3-methylimidazo[1,2-a]pyridin-2-amine (6)

2,2,2-trifluoro-N-(6-fluoro-3-methylimidazo[1,2-a]pyridin-2-yl)acetamide (0.188 g, 0.00072 mol) was dissolved in methanol (4.0 mL) and water (0.5 mL). Potassium carbonate (0.40 g, 0.0029 mol) was added and heated in the microwave for 45 min at 100° C. The solvent concentrated and residue was partitioned between water (50 mL) and ethyl acetate (50 mL). The layers were separated and the organic layer was dried (magnesium sulfate) then chromatographed on silica (55:40:5, DCM:acetonitrle:MeOH) to give 6-fluoro-3-methylimidazo[1,2-a]pyridin-2-amine Rf 0.47, (55:40:5, DCM:acetonitrle:MeOH); MS m/z 166 (M+H).

Synthesis of 3,3,3-trifluoro-N-(6-fluoro-3-methylimidazo[1,2-a]pyridin-2-yl)propanamide (7)

6-fluoro-3-methylimidazo[1,2-a]pyridin-2-amine (0.033 g, 0.00020 mol) was dissolved in dichloromethane (3.0 mL) and N,N-diisopropylethylamine (0.070 mL, 0.00040 mol) was added. The reaction was cooled to 0° C. and 3,3,3-trifluoropropionyl chloride (29 uL, 0.00024 mol) was added. The mixture was warmed to room temperature and was stirred for 1 hour. Solvent removed and residue was chromatographed on silica (70% ethyl acetate/hexanes) to give 3,3,3-trifluoro-N-(6-fluoro-3-methylimidazo[1,2-a]pyridin-2-yl)propanamide Rf 0.43, 70% ethyl acetate/hexanes; MS m/z 276 (M+H). SH-SY5Y_EC50 (μM): 10.

The following compounds were prepared according to the procedures of Method 5. The number next to each compound listed below corresponds to the compound number in Table 5.

2,2,2-trifluoro-N-(6-fluoro-3-methylimidazo[1,2-a]pyridin-2-yl)acetamide 421

N-(6-fluoro-3-methylimidazo[1,2-a]pyridin-2-yl)-2-(4-fluorophenyl)acetamide 422

N-(6-fluoro-3-methylimidazo[1,2-a]pyridin-2-yl)-3,3-dimethylbutanamide 423

3,3,3-trifluoro-N-(6-fluoro-3-methylimidazo[1,2-a]pyridin-2-yl)propanamide 424

N-(6-fluoro-3-vinylimidazo[1,2-a]pyridin-2-yl)-2-(4-fluorophenyl)acetamide 425

2-(4-fluorophenyl)-N-(7-(trifluoromethyl)-3-vinylimidazo[1,2-a]pyridin-2-yl)acetamide 426

3,3,3-trifluoro-N-(7-(trifluoromethyl)-3-vinylimidazo[1,2-a]pyridin-2-yl)propanamide 427

N-(5-(benzyl(methyl)amino)imidazo[1,2-a]pyridin-2-yl)-3,3-dimethylbutanamide

Table 5 sets forth potencies, purity, calculated molecular weights and measured molecular weights of representative compounds of the invention in the SH-SY5Y native cell line in a FLIPR assay, for a selection of compounds. The compound numbers in Table 5 correspond to the compound numbers following each compound listed above in Example 5.

TABLE 5

| Compound No. | SH-SY5Y EC50, μM | Purity (%) | Molecular Weight | Observed m/z (M + H) |
|---|---|---|---|---|
| 421 | + | 98 | 261.2 | 262.2 |
| 422 | + | 98 | 301.3 | 302.3 |
| 423 | + | 98 | 263.3 | 264.3 |
| 424 | + | 98 | 275.2 | 276.2 |
| 425 | ++ | 98 | 313.3 | 314.3 |
| 426 | ++ | 98 | 363.3 | 364.3 |
| 427 | + | 98 | 337.2 | 338.2 |

"+" represents 10 μM > EC$_{50}$ > 3 μM
"++" represents 3 μM > EC$_{50}$ > 0.5 μM
"+++" represents EC$_{50}$ < 0.5 μM

Example 6

Preparation N-(3-cyclopropyl-6-(trifluoromethyl)imidazo[1,2-b]pyridazin-2-yl)-3,3,3-trifluoro-2,2-dimethylpropanamide (434)

Method 6

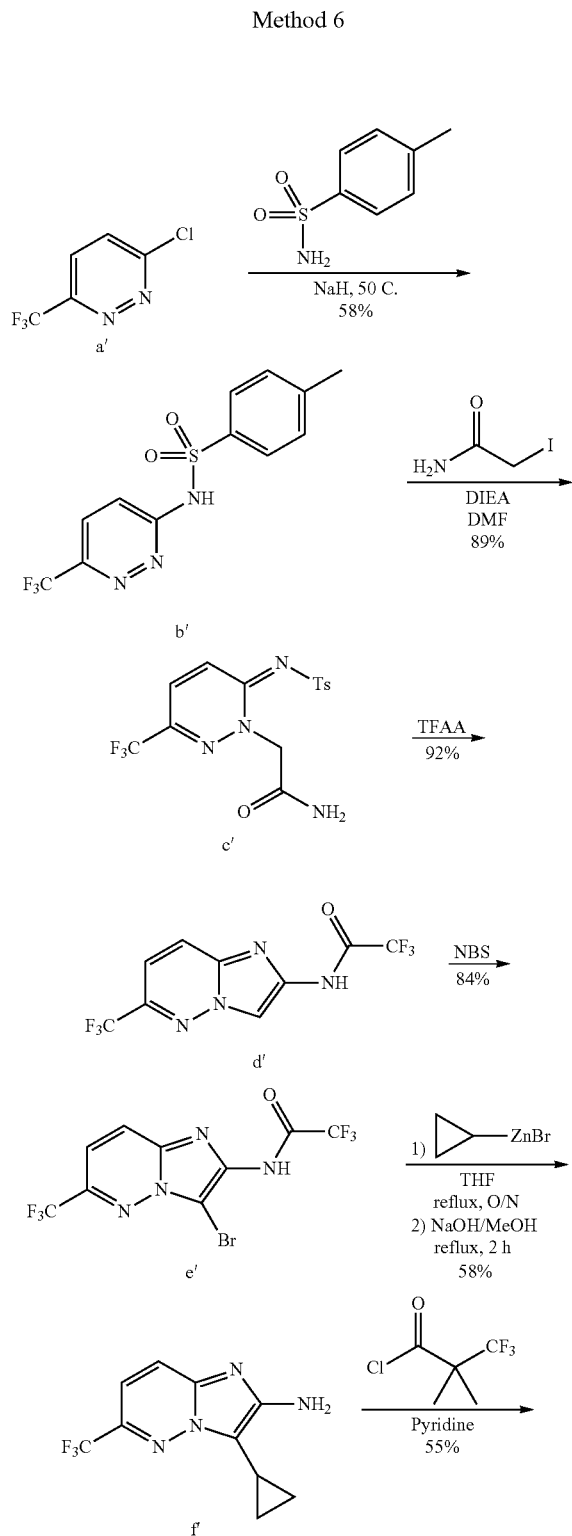

Synthesis of 4-Methyl-N-(6-trifluoromethylpyridazine-3-yl)benzenesulfonamide (b')

To a solution of 4-methylbenzenesulfonamide (25 g, 0.15 mol) in DMSO (100 mL) was added NaH (7.0 g, 0.18 mol, 1.2 eq) in 1 g portions over about 2 h. The reaction foamed considerably as the NaH was added and excess DMSO was used to wash down sides of flask (total volume of extra DMSO added about 100 mL). After all NaH was added the reaction was stirred at RT for 10 min and then compound a' (27 g, 0.15 mol) was added. The reaction turned dark brown and the mixture was heated to 50° C. and stirred overnight. The mixture was cooled to RT and quenched by addition of EtOAc and 1M HCl. The layers were separated and the aqueous layer was extracted with EtOAc. The combined extracts were dried over MgSO$_4$ and concentrated in vacuo onto celite. This mixture was separated into two equal portions and each was chromatographed (silica gel, gradient 0-20% EtOAc/Hexanes and then maintaining 20% EtOAc/Hexanes) to provide 26.79 g (58%) of a red solid MS m/z 318 (M+H).

Synthesis of (Z)-2-(6-Tosylimino-3-trifluoromethyl)pyridazine-1(6H)-yl)acetamide (c')

To a cooled solution (0° C.) of 4-Methyl-N-(6-trifluoromethyl pyridazine-3-yl)benzenesulfonamide (compound b', 16.03 g, 0.05 mol) in DMF (60 mL) was added N,N-diisopropylethylamine (11 mL, 0.066 mol). The mixture was stirred at 0° C. for 1 h then iodoacetamide was added (11 g, 0.061 mol, 1.2 eq). The ice bath was removed and the mixture was stirred at RT overnight. Water (ca 400 mL) was then added and the resulting solid was collected by filtration. The solid was dried to provide 16.7 g (88%) of a reddish brown solid which was used without further purification MS m/z 375 (M+H).

Synthesis of 2,2,2-Trifluoro-N-(6-(trifluoromethyl)imidazo[1,2-b]pyridazin-2yl)acetamide (d')

To a solution of (Z)-2-(6-Tosylimino-3-trifluoromethyl)pyridazine-1(6H)-yl)acetamide c' (1132 g, 0.03 mol) in DCM (150 mL) was slowly added TFAA (30 mL, 0.2 mol). The mixture was stirred at RT for 1 h. The mixture was concentrated in vacuo to remove excess TFAA. The residue was partitioned between DCM and sat. NaHCO$_3$ and the layers were separated and aqueous layer extracted with DCM. The organic was washed with sat. NaHCO$_3$, dried over MgSO$_4$ and concentrated in vacuo to provide 7.89 g (88%) of a brown solid MS m/z 299 (M+H).

Synthesis of N-(3-Bromo-6-trifluoromethyl)imidazo[1,2-b]pyridazin-2-yl)-2,2,2-trifluoroacetamide (e')

2,2,2-Trifluoro-N-(6-(trifluoromethyl)imidazo[1,2-b]pyridazin-2yl)acetamide (d') (12.27 g, 0.041 mol) was suspended in CH₃CN (80 mL) and cooled to 0° C. NBS (8.0 g, 0.045 mol) was added in four (1.3 g) portions and the mixture was stirred at 0° C. for 30 minutes. Water (200 mL) was added and the resulting solid was collected by filtration, washed with water and dried to provide 13.11 g (84%) of a solid MS m/z 378 (M+H).

Synthesis of 3-Cyclopropyl-6-(trifluoromethyl)imidazo[1,2-b]pyridin-2-amine (f')

To a solution of N-(3-Bromo-6-trifluoromethyl)imidazo[1,2-b]pyridazin-2yl)-2,2,2-trifluoroacetamide e' (16 g, 0.042 mol,) in THF (100 mL) was added 4 A molecular sieves. The mixture was stirred at RT for 30 minutes and then a solution of cyclopropylzinc bromide in THF (0.5M, 250 mL) was added followed by Pd(dppf)Cl₂-DCM (1.71 g, 0.0021 mol,). The resulting mixture was heated to reflux overnight and then an additional 50 mL (0.025 mol) of cyclopropylzinc bromide solution was added and heating continued for 2 h. The mixture was concentrated in vacuo and to the residue was added MeOH (320 mL) and NaOH (6.0M, 160 mL). The mixture was heated to reflux for about 2 h and then stirred overnight at RT. The mixture was concentrated by half in vacuo and DCM was added and then filtered through celite. Water added to the filtrate and the layers separated. The aqueous layer was extracted with DCM and the combined extracts were dried over MgSO₄ and concentrated in vacuo. The residue was purified by column chromatography using silica gel and a gradient of 0-100% EtOAc/hexanes to provide 5.99 g (58%) of a solid MS m/z 243 (M+H).

Synthesis of N-(3-cyclopropyl-6-(trifluoromethyl)imidazo[1,2-b]pyridazin-2-yl)-3,3,3-trifluoro-2,2-dimethylpropanamide (435)

To a solution of 3,3,3-trifluororo-2,2-dimethylpropionic acid (3.4 g, 21.8 mmol) at 0° C. was added 1 drop of DMF followed by oxalyl chloride (1.99 mL, 23.6 mmol) and the solution stirred at RT for 3 h. An additional 200 µL of oxalyl chloride was added and more stirring continued for an additional 1 h.

To a solution of 3-cyclopropyl-6-(trifluoromethyl)imidazo[1,2-b]pyridin-2-amine (f') (4.39 g, 18.1 mmol) in THF (30 mL) was added pyridine (2.93 mL, 36.2 mmol). The solution was cooled to 0° C. and the acid chloride solution from above was added dropwise over about 10 min. The mixture was allowed to warm to RT and stirred overnight. The mixture was concentrated in vacuo and the residue was purified by column chromatography using silica gel and a gradient of 0-50% EtOAc/hexanes to provide 3.79 g (55%) of the desired product MS m/z 381 (M+H).

The following compounds were prepared according to the procedures of Method 6. The number next to each compound listed below corresponds to the compound number in Table 6.
N-(3-cyclobutyl-6-(trifluoromethyl)imidazo[1,2-a]pyridin-2-yl)-3,3,3-trifluoro-2,2-dimethylpropanamide 428
N-(3-cyclopropyl-6-(trifluoromethyl)imidazo[1,2-a]pyridin-2-yl)-3,3,3-trifluoro-2,2-dimethylpropanamide 429
N-(3-cyclopentyl-6-(trifluoromethyl)imidazo[1,2-a]pyridin-2-yl)-3,4-difluorobenzamide 430
N-(3-cyclobutyl-6-(trifluoromethyl)imidazo[1,2-a]pyridin-2-yl)-4,4,4-trifluoro-3,3-dimethylbutanamide 431
N-(3-cyclopropyl-6-(trifluoromethyl)imidazo[1,2-a]pyridin-2-yl)-4,4,4-trifluoro-3,3-dimethylbutanamide 432
4,4,4-trifluoro-N-(6-fluoro-3-(4-(trifluoromethyl)pyridin-2-yl)imidazo[1,2-a]pyridin-2-yl)-3,3-dimethylbutanamide 433
N-(3-cyclopropyl-6-(trifluoromethyl)imidazo[1,2-b]pyridazin-2-yl)-3,4-difluorobenzamide 434
N-(3-cyclopropyl-6-(trifluoromethyl)imidazo[1,2-b]pyridazin-2-yl)-3,3,3-trifluoro-2,2-dimethylpropanamide 435
N-(3-cyclopropyl-6-(trifluoromethyl)imidazo[1,2-b]pyridazin-2-yl)-4,4,4-trifluoro-3,3-dimethylbutanamide 436
N-(3-cyclobutyl-6-(trifluoromethyl)imidazo[1,2-b]pyridazin-2-yl)-3,3,3-trifluoro-2,2-dimethylpropanamide 437
N-(3-cyclobutyl-6-(trifluoromethyl)imidazo[1,2-b]pyridazin-2-yl)-4,4,4-trifluoro-3,3-dimethylbutanamide 438
N-(3-cyclobutyl-6-(trifluoromethyl)imidazo[1,2-b]pyridazin-2-yl)-4,4,4-trifluoro-3,3-dimethylbutanamide 439
4,4,4-trifluoro-3,3-dimethyl-N-(3-neopentyl-6-(trifluoromethyl)imidazo[1,2-a]pyridin-2-yl)butanamide 440
N-(3-cyclohexyl-6-(trifluoromethyl)imidazo[1,2-a]pyridin-2-yl)-4,4,4-trifluoro-3,3-dimethylbutanamide 441
N-(3-cyclopentyl-6-(trifluoromethyl)imidazo[1,2-a]pyridin-2-yl)-4,4,4-trifluoro-3,3-dimethylbutanamide 442
4,4,4-trifluoro-N-(3-isopentyl-6-(trifluoromethyl)imidazo[1,2-a]pyridin-2-yl)-3,3-dimethylbutanamide 443
N-(3-(cyclohexylmethyl)-6-fluoroimidazo[1,2-a]pyridin-2-yl)-4,4,4-trifluoro-3,3-dimethylbutanamide 444
N-(3-cyclopropyl-6-(trifluoromethyl)imidazo[1,2-b]pyridazin-2-yl)-2-(1-methylcyclopentyl)acetamide 445
N-(3-cyclobutyl-6-fluoroimidazo[1,2-a]pyridin-2-yl)-4,4,4-trifluoro-3,3-dimethylbutanamide 446
N-(3-cyclopentyl-6-(trifluoromethyl)imidazo[1,2-b]pyridazin-2-yl)-3,4,-difluorobenzamide 447

Table 6 sets forth potencies, purity, calculated molecular weights and measured molecular weights of representative compounds of the invention in the SH-SY5Y native cell line in a FLIPR assay, for a selection of compounds. The compound numbers in Table 6 correspond to the compound numbers following each compound listed above in Example 6.

TABLE 6

| Compound No. | SH-SY5Y EC50 µM | Purity (%) | Molecular Weight | Observed m/z (M + H) |
|---|---|---|---|---|
| 428 | +++ | 99 | 393.3 | 394.30 |
| 429 | ++ | 97 | 379.3 | 380.30 |
| 430 | ++ | 98 | 409.35 | 410.35 |
| 431 | +++ | 98 | 407.35 | 408.35 |
| 432 | +++ | 98 | 393.33 | 394.33 |
| 433 | ++ | 99 | 448.34 | 449.34 |
| 434 | ++ | 98 | 382.29 | 383.29 |
| 435 | ++ | 99 | 380.29 | 381.29 |
| 436 | ++ | 99 | 446.44 | 447.44 |
| 437 | ++ | 95 | 394.31 | 395.31 |
| 438 | +++ | 95 | 394.31 | 395.31 |
| 439 | +++ | 98 | 408.34 | 409.34 |
| 440 | +++ | 95 | 423.40 | 424.40 |
| 441 | +++ | 99 | 435.41 | 436.41 |
| 442 | +++ | 95 | 421.38 | 422.38 |
| 443 | +++ | 95 | 423.40 | 424.40 |
| 444 | +++ | 95 | 399.43 | 400.43 |
| 445 | +++ | 95 | 366.38 | 367.38 |
| 446 | +++ | 98 | 357.34 | 358.34 |
| 447 | ++ | 98 | 410.34 | 411.34 |

"+" represents 10 µM > EC50 > 3 µM
"++" represents 3 µM > EC50 > 0.5 µM
"+++" represents EC50 < 0.5 µM

Example 7

Preparation of 4,4,4-Trifluoro-3,3-dimethyl-butyric acid (v)

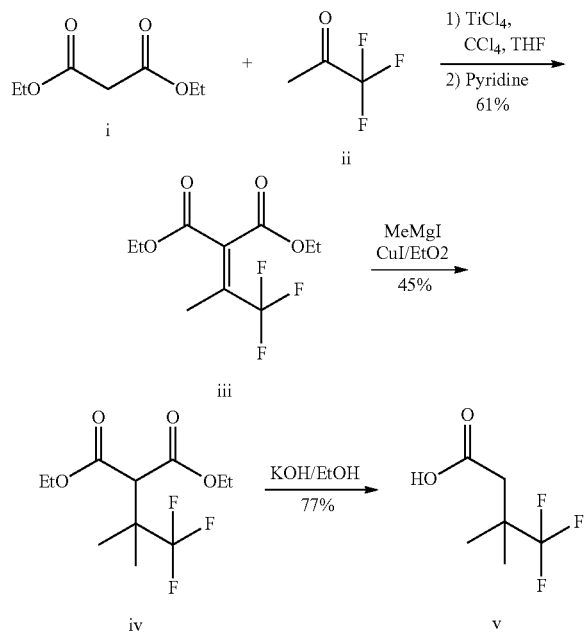

Synthesis of diethyl 2-(1,1,1-triflouorpropan-2-ylideine)malonate (iii)

To a solution of TiCl$_4$ (1M CH$_2$Cl$_2$, 300 mL, 300 mmol) was added THF (475 mL, 5860 mmol) and CCl$_4$ (85 mL, 880 mmol). The mixture was cooled to 0° C. and 1,1,1-trifluoroacetone (i, 14 mL, 160 mmol) was followed by ethyl malonate (ii, 24 mL, 160 mmol). The mixture was stirred for 1.5 hr and then pyridine (50 mL, 620 mmol) was added and stirring continued for 18 h. At the end of that time the previous black solution is yellow and a white precipitate is present. Water is added followed by Et$_2$0. The Et$_2$0 layer is collected and the aqueous layer is extracted with Et$_2$0 (2×). The organic layers were combined, dried over MgSO$_4$, filtered and concentrated. The residue is purified by column chromatography (2×, SiO$_2$, 0-10% EtOAc/hexanes) to provide the title compound as a yellow liquid (24.5 g, 61%).

Synthesis of diethyl 2-(1,1,1-triflouoro-2-methylpropan-2-yl)malonate (iv)

A mixture of MeMgI (18 mL 3.0 M in Et$_2$0, 54 mmol) and CuCl (207 mg, 2.09 mmol) were cooled to −10° C. To this was added diethyl 2-(1,1,1-triflouorpropan-2ylideine)malonate (iii, 6.8 g, 27 mmol) in Et$_2$0 (100 mL, 1000 mmol) over 1 hr. The reaction was stirred at −10° C. for 2 hours and then allowed to warm to rt overnight. The reaction was poured into ice water and Et$_2$0 was added (100 mL) followed by H$_2$S0$_4$ (2 N, 20 mL). The layers were separated and the aqueous layer extracted with ether (2×). The organic layers were combined and dried over MgSO$_4$, filtered and concentrated. The resulting residue was chromographed (SiO$_2$, 0-40% EtOAc/hexanes) to provide the title compound as a light purple liquid (19.5 g, 45%).

Synthesis of 4,4,4-Trifluoro-3,3-dimethyl-butyric acid (v)

A solution of diethyl 2-(1,1,1-trifluoro-2-methylpropan-2-yl)malonate (iv, 20.93 g, 77.45 mmol) and KOH (17.23 g, 307.1 mmol) in EtOH (200 mL, 3000 mmol) was heated at 80° C. for 16 h. The reaction was concentrated and partitioned between water and Et$_2$O. The aqueous layer was acidified with 6 N HCl and then extracted with Et$_2$O (2×). The organic layers were combined, dried over MgSO$_4$, filtered and concentrated to provide and orange oil. A low pressure distillation gave the product as a light pink liquid (10.17 g, 77%).

Example 8

Materials and Methods

SH-SY5Y cells, a mouse neuroblastoma, rat glioma hybrid cell line, functionally express M-currents (Robbins et al., *J. Physiol.* 451: 159-85 (1992). SH-SY5Y M-currents are likely comprised, at least in part, of KCNQ2, KCNQ3 and KCNQ5, since these genes are reportedly robustly expressed in differentiated SH-SY5Y cells (Selyanko et al., *J. Neurosci.* 19(18): 7742-56 (1999); Schroeder et al., *J. Biol. Chem.* 275(31): 24089-95 (2000)) and KCNQ3 dominant-negative constructs reduce M-current density in these cells (Selyanko et al., *J. Neurosci.* 22(5): RC212 (2002).

SH-SY5Y were maintained in DMEM (high glucose) supplemented with 10% fetal bovine serum, 0.05 mM pyridoxine, 0.1 mM hypoxanthine, 400 nM aminopterin, 16 mM thymidine, 50 µgml$^{-1}$ gentamycin and 10 mM HEPES, in an incubator at 37° C. with a humidified atmosphere of 5% CO$_2$. Cells were plated in 96 well plates differentiated by addition of 10 µM PGE1 and 50 µM isomethylbutylxanthine to the growth media prior to study.

Differentiated SH-SY5Y cells were loaded with voltage-sensitive dye by incubation in Earls Balanced Salt Solution (EBSS) containing 5 mM DiBAC for 1 h. Following loading, drug solution containing 5 mM DiBAC was added to each well. Changes in fluorescence were measured every 30 s for 25 min. The maximum change in fluorescence was measured and expressed as a percentage of the maximum response obtained in the presence of a positive control agent.

Example 9

In Vivo Rat Assay for Anti-Convulsant Activity

Male Wistar rats were housed 4 per cage on a regular light/dark cycle (lights on 0600-1800) for one week prior to anti-convulsant testing. The apparatus used to induce electroshock seizure was obtained from Walhquist Instrument Co., Salt Lake City, Utah. The shock level was set at 150 mA and the duration at 0.2 seconds. A drop of 1% proparacaine solution was placed in each eye of a rat, the electrodes were placed over the eyes, and the shock was administered. Latency to hind limb extension was measured to the nearest 0.1 second. If extension did not occur within 6 seconds, the rat was scored as protected and a value of 6 seconds was recorded.

The KCNQ opener was homogenized in either 0.5% carboxymethylcellulose in water or 0.5% methylcellulose in water) and administered orally through a steel 18-gauge rat gavage tube in a volume of 2 mL/kg of body weight. In the single dose screening assay, latency to seizure for the vehicle group and the KCNQ opener group were compared using t-test. Typically a dose of 10 mg/kg of the opener is used. However, openers can be run n a dose-response experiment where doses of 1, 3, 10 and 30 mg/Kg are used.

In the single dose screening assay, latency to seizure for the vehicle and the 10 mg/kg groups were compared using t-test. Latencies to seizure in the dose response studies were submitted to analysis of variance and all dose groups were compared to vehicle using Dunnett's method (JMP© ver 5.1, SAS). In all cases an effect was considered significant if p≤0.05. Tables 7 and 8 provide examples of the screening and dose-response data.

TABLE 7

| Examples | Rat MES activity |
|---|---|
| 128 | +++ |
| 153 | +++ |
| 353 | +++ |
| 180 | ++ |
| 198 | +++ |
| 360 | + |
| 19 | +++ |
| 20 | + |
| 225 | ++ |
| 363 | ++ |
| 23 | + |
| 24 | + |
| 271 | ++ |
| 32 | + |
| 38 | ++ |
| 51 | ++ |
| 371 | ++ |
| 308 | +++ |
| 316 | ++ |
| 68 | +++ |
| 89 | +++ |
| 428 | +++ |
| 429 | +++ |
| 430 | ++ |
| 431 | +++ |
| 434 | ++ |
| 435 | +++ |
| 437 | +++ |
| 438 | +++ |
| 439 | +++ |
| 446 | +++ |

+ 2-3 animals protected
++ 4-6 animals protected
+++ 7-8 animals protected

TABLE 8

| Examples | ED50 (mpk) |
|---|---|
| 19 | 2.3 |
| 371 | 3.6 |
| 153 | 0.5 |
| 19 | <1 |
| 308 | 1.6 |
| 89 | 5.8 |
| 428 | 1.1 |
| 429 | 3.4 |
| 430 | 2.3 |
| 431 | 5.2 |
| 433 | 3.9 |
| 436 | 0.7 |
| 439 | 0.47 |

In Vivo Rat Assay for Neuropathic Pain

A neuropathic pain condition is induced in rats using a nerve injury model similar to the method described by Kim and Chung (Kim, S. H. & Chung, J. M. (1992) *Pain* 50:355-363). Rats (Male Sprague-Dawley, Charles River, Wilmington, Mass.) weighing 200-300 grams were utilized. Food and water was available ad libitum except during testing) are anesthetized with halothane and the L5 spinal nerve is exposed, carefully isolated, and tightly ligated with 4.0 silk suture distal to the dorsal root ganglia. The wounds are sutured and the animals are allowed to recover in individual cages. To test the effect of a KCNQ opener on tactile allodynia following L5 nerve ligation, Von Frey tactile withdrawal thresholds are determined. Test animals are placed in a box separated by walls with a wire mesh floor allowing access to the plantar surface of the paw. Tactile testing is conducted using set of calibrated nylon fibers (Von Frey hairs), each approximately 3 cm long and sequentially increasing in diameter and stiffness, mounted on handles. Beginning with a medium hair, the tip of the fiber is placed on the plantar surface of the rat paw and applied with a pressure to make it slightly bend. If the rat responds by lifting its paw the next descending hair is tested. Failure to lift the hind paw after 4 seconds is scored as a negative response and the next ascending hair is applied. Dixon's Up-Down Method is applied for a total of 6 responses following and including the first change in response to determine 50% paw withdrawal thresholds. Data analysis was conducted using analysis of variance and appropriate post-hoc comparisons (P<0.05) as previously described. $ED_{50}$ values were estimated using least squares linear regression.

Baseline measurements of allodynia are performed immediately prior to subject selection and compound administration. Only rats found to be allodynic (mean 50% gram withdrawal thresholds <5) are selected as subjects for each days study. Sample sizes vary with number of available allodynic animals, generally 5-8 per treatment group. The KCNQ opener was homogenized in either 0.5% carboxymethylcellulose in water or 0.5% methylcellulose in water) and administered orally through a steel 18-gauge rat gavage tube in a volume of 2 mL/kg of body weight. The doses range from 1-100 mg/kg with a typical experiment using 1, 3, 10 and 30 mg/kg to generate and $ED_{50}$ value. The openers are typically given 30 minutes to 2 hours prior to testing. Additional paw withdrawal thresholds are measured at various time intervals after compound administration. Examples 153 and 19 were evaluated in this assay. Example 153 has an $ED_{50}$ value of 1.9 mg/kg and Example 19 has an $ED_{50}$ of 10 mg/kg.

In Vivo Rat Model for Inflammatory Pain

In this model of acute inflammation, carrageenan is injected into the paw resulting in a local inflammation and thermal hyperalgesia, which is demonstrated by a reduction in the escape latency of the inflamed paw when presented with a thermal stimulus. Compounds with anti-hyperalgesic activity will increase (or lengthen) the escape latency of the inflamed paw.

To induce a local inflammation, 50 μL of a 1% solution of λ-carrageenan in sterile water is injected subcutaneously into the plantar surface of the right hind paw of the rat (Sprague Dawley rats, sample size=8 per treatment group). The KCNQ openers typically at doses ranging from 1-100 mg/kg were homogenized in either 0.5% carboxymethylcellulose in water or 0.5% methylcellulose in water and administered orally through a steel 18-gauge rat gavage tube in a volume of 2 mL/kg of body weight 30 minutes prior to carrageenan injection. After carrageenan injection behavioral testing is conducted at the appropriate time following opener or vehicle administration (generally $T_{max}$, the time of maximum plasma levels of the compound being tested). To assess the thermally evoked paw withdrawal response, a commercially available Hargreaves Box was used (UCSD Department of Anesthesiology, San Diego; La Jolla, Calif., stimulus intensity 5.25 amps). Rats were placed on a thin glass surface in individual chambers made of clear plastic. A small high intensity projection bulb, mounted on a moveable arm under the glass with a mirrored base that can be positioned under the paw, served as the thermal stimulus. The time to withdrawal response is measured in seconds and assigned as the response latency. Both right and left hind paws (inflamed and uninflamed paws) were tested in each animal and the data reported as the mean of three measurements taken within a 5 minute time period. Example 153 had an $ED_{50}$ of 0.5-1 mg/kg.

Metabolic Stability and In Vivo Properties

Compounds 65 and 366, when administered orally to rats (10 mg/kg) undergo metabolism at the terminal carbon of the t-butyl group as determined by mass spectrometry. Metabolite 14% of parent for compound 65 and metabolite 35% of parent for compound 366 were observed. Compounds such as 431 and 433 containing the 4,4,4-trifluoro-3,3-dimethylbutanoic acid show little or no metabolism in rats.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A compound of Formula (IXb):

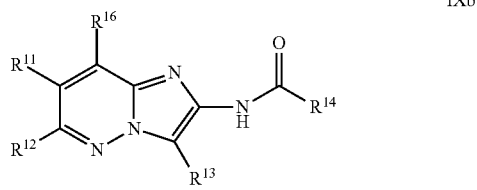

IXb or a pharmaceutically acceptable salt thereof, wherein,
$R^{11}$ and $R^{12}$ are each independently selected from the group consisting of —H, halogen, $C_{1-8}$haloalkyl, —CN, $C_{1-8}$alkyl, $C_{1-8}$alkoxy, aryloxy and aryl-$C_{1-8}$alkoxy;
$R^{13}$ is selected from the group consisting of $C_{1-8}$alkyl, $C_{2-8}$alkenyl, aryl, $C_{3-8}$cycloalkyl, aryl-$C_{1-6}$alkyl, $C_{3-8}$cycloalkyl-$C_{1-8}$alkyl, heteroaryl and heteroaryl-$C_{1-6}$alkyl, wherein the aromatic portion of the $R^{13}$ group is optionally substituted with from 1-3 $R^a$ substituents, each $R^a$ is independently selected from the group consisting of halogen, $C_{1-8}$haloalkoxy, $C_{1-8}$alkoxy, $C_{1-8}$haloalkyl, —CN and $R^b$, wherein $R^b$ is $C_{1-8}$alkyl optionally substituted with from 1-2 substituents selected from halogen, —CN, —OH, $C_{1-8}$haloalkoxy or $C_{1-8}$alkoxy; or any two adjacent $R^a$ substituents together with the atoms to which they are attached form a 5- or 6-membered carbocyclic ring, optionally substituted with a $C_{1-8}$alkyl;
$R^{14}$ is selected from the group consisting of $C_{1-8}$alkyl, $C_{1-8}$haloalkyl, $C_{3-8}$cycloalkyl, $C_{3-8}$cycloalkyl-$C_{1-8}$alkyl, aryl, aryl-$C_{1-8}$alkyl, $C_{1-8}$alkoxy, aryl-$C_{1-8}$alkoxy, $C_{4-5}$heterocycloalkyl, $C_{4-5}$heterocycloalkyl-$C_{1-8}$alkyl, $R^c$, —NHR$^d$ and —N(R$^d$)$_2$, wherein $R^c$ is $C_{1-8}$alkyl substituted with from 1-2 members selected from —OH, —OC(O) $C_{1-8}$alkyl, —CH$_2$N(R$^d$)$_2$, —OC(O)aryl, $C_{1-8}$alkoxy or aryloxy, and $R^d$ is $C_{1-8}$alkyl or aryl-$C_{1-8}$alkyl, wherein the aromatic portion of the $R^{14}$ group is optionally substituted with from 1-3 $R^e$ substituents independently selected from the group consisting of halogen, $C_{1-8}$haloalkyl, $C_{1-8}$alkyl, $C_{1-8}$alkoxy, —CN, haloalkoxy, —OH, —OC(O)O—R$^f$, —OC(O)R$^f$, —OC(O)NHR$^f$, —OC(O)N(R$^f$)$_2$, —S(O)R$^f$, —S(O)$_2$R$^f$, —SO$_2$NH$_2$, —S(O)$_2$NHR$^f$, —S(O)$_2$N(R$^f$)$_2$, —NHS(O)$_2$R$^f$, —NR$^f$S(O)$_2$R$^f$, —C(O)NH$_2$, —C(O)NHR$^f$, —C(O)N(R$^f$)$_2$, —C(O)R$^f$, and —C(O)H, wherein each R$^f$ is independently a $C_{1-8}$alkyl;

and the cycloalkyl portion of the $R^{14}$ group is optionally substituted with from 1-3 substituents selected from halogen, or $C_{1-8}$alkyl; or optionally fused with a 5- or 6 membered aromatic ring having from 0-2 heteroatoms as ring members selected from N, O or S; and $R^{16}$ is selected from the group consisting of —H, $C_{1-8}$alkyl, halogen, —CN, $C_{1-8}$haloalkoxy, —OR$^g$ and —N(R$^g$)$_2$, wherein $R^g$ is independently —H, $C_{1-8}$alkyl or aryl-$C_{1-8}$alkyl.

2. The compound of claim 1, or a pharmaceutically acceptable salt thereof, represented by a Formula selected from:

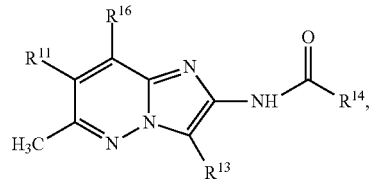

IXb-1

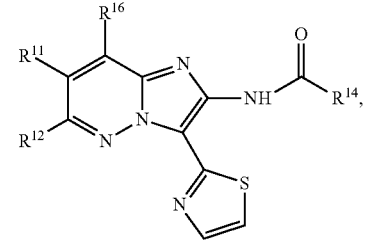

IXb-2

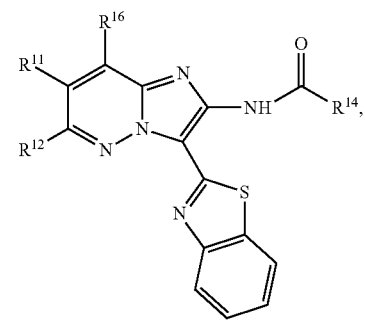

IXb-3

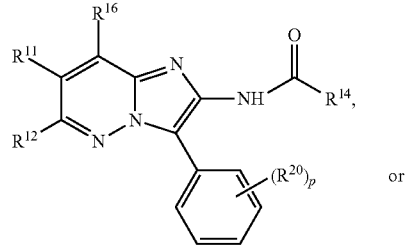

IXb-4 or

-continued

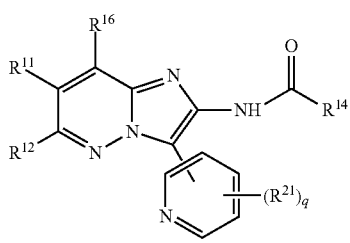

IXb-5 wherein the subscripts p and q are each independently an integer of 0-3; and $R^{20}$ and $R^{21}$ are each independently selected from the group consisting of halogen, $C_{1-8}$haloalkoxy, $C_{1-8}$alkoxy, —CN and Rb.

3. The compound of claim 1, or a pharmaceutically acceptable salt thereof, represented by the Formula:

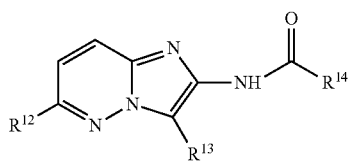

IXd-2 or a pharmaceutically acceptable salt thereof.

4. The compound of claim 3, or a pharmaceutically acceptable salt thereof, wherein $R^{12}$ is F or $CF_3$.

5. The compound of claim 4, or a pharmaceutically acceptable salt thereof, wherein $R^{13}$ is cyclopropyl, cyclobutyl, cyclopentyl, cyclohexyl, 1-methylcyclopentyl, 1-methylcyclopentylmethyl, cyclohexylmethyl, 4-trifluoromethyl-2-pyridyl, 2,2-dimethylpropyl or 3-methyl-1-butyl.

6. The compound of claim 4, or a pharmaceutically acceptable salt thereof, wherein $R^{14}$ is $CF_3(CH_3)_2CCH_2$—, $CF_3(CH_3)_2C$—, 3,4-difluorophenyl or 1-methyl-cyclopentylmethyl.

7. A pharmaceutical composition comprising a compound of claim 1, or a pharmaceutically acceptable salt thereof, and a pharmaceutically acceptable excipient.

8. A compound represented by the Formula:

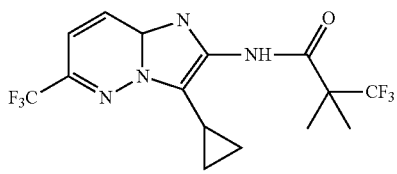 [SMILES: CC(C)(C(=O)NC1=C(C2CC2)N2N=C(C(F)(F)F)C=CC2N1)C(F)(F)F]

or a pharmaceutically acceptable salt thereof.

9. A pharmaceutical composition, comprising a compound represented by the Formula:

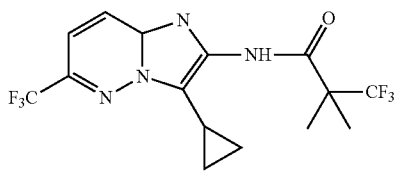 [SMILES: CC(C)(C(=O)NC1=C(C2CC2)N2N=C(C(F)(F)F)C=CC2N1)C(F)(F)F]

or a pharmaceutically acceptable salt thereof, and a pharmaceutically acceptable excipient.

* * * * *